United States Patent
Obrecht et al.

(10) Patent No.: US 7,417,024 B2
(45) Date of Patent: Aug. 26, 2008

(54) TEMPLATE-FIXED PEPTIDOMIMETICS AS INHIBITORS OF SERINE PROTEASES

(75) Inventors: Daniel Obrecht, Bättwil (CH); John Anthony Robinson, Wermatswil (CH); Anne Descours, Zürich (CH)

(73) Assignees: Polyphor Ltd., Allschwil (CH); Universität Zürich, Zürich (CH)

( * ) Notice: Subject to any disclaimer, the term of this patent is extended or adjusted under 35 U.S.C. 154(b) by 247 days.

(21) Appl. No.: 10/498,468

(22) PCT Filed: Dec. 11, 2001

(86) PCT No.: PCT/EP01/14528

§ 371 (c)(1),
(2), (4) Date: Jan. 7, 2005

(87) PCT Pub. No.: WO03/054000

PCT Pub. Date: Jul. 3, 2003

(65) Prior Publication Data

US 2005/0187145 A1    Aug. 25, 2005

(51) Int. Cl.
*A61K 38/08* (2006.01)
*A61K 38/10* (2006.01)
*C07K 7/06* (2006.01)
*C07K 7/08* (2006.01)
*C07K 7/64* (2006.01)

(52) U.S. Cl. ......................................... 514/11; 530/321
(58) Field of Classification Search ........................ None
See application file for complete search history.

(56) References Cited

FOREIGN PATENT DOCUMENTS

WO    WO 01/16161    3/2001

OTHER PUBLICATIONS

Spath et al. Stabilization of a beta-Hairpin in a Cyclic Peptide . . . Helvetica Chimica Acta. 1998, vol. 81, pp. 1726-1738.*

Hollosi et al. Ion Binding Properties In Acetonitrile of Cyclopeptides Built Up From Proline And Glycine Residues. International Journal of Peptide and Protein Reserch. 1977, vol. 10, pp. 329-341.*

Obrecht et al.; Novel Peptide Mimetic Buliding Blocks and Strategies for Effcient Lead Finding; Advances in Medicinal Chemistry, JAI Press, U.S.; Apr. 1999, pp. 1-68.

Robinson; The Design, Synthesis and Conformation of Some New beta-Hairpin Mimetics: Novel Reagents for Drug and Vaccine Discolvery; Synlett, vol. 1999, No. 4, Apr. 2000, pp. 429-441.

Jiang, et la., Combinatorial Biomimetic Chemistry: Parallel Syntheis of a Small Library of beta-Hairpin Mimetics Based on Loop III from Human Platelet-Derived Growth Factor B; Helvetica Chimica Acta; vol. 83, No. 12, Dec. 2000; pp. 3097-3112.

Pfeifer et al.; Stabilization of beta-hairpin conformations in a protein surface mimetic using a bicycle template derived from (2S,3R, 4R)-diaminoproline; Chem. Commun.; Cmabridge; 1998, vol. 18, pp. 1977-1978.

Spath et al.; Stabilization of a β-Hairpin Comformation in a Cyclic Peptide Using the Templating Effect of a Heterochiral Diproline Unit; Helvetica Chimica Acta, vol. 81, 1998, pp. 1726-1738.

Descours et al.; A New Family of β-Hairpin Mimetics Based on a Tyrpsin Inhibitor fomr Sunflower Seeds; ChemBioChem 2002, 3, pp. 318-323.

* cited by examiner

*Primary Examiner*—Jeffrey Edwin Russel
(74) *Attorney, Agent, or Firm*—Hoffmann & Baron, LLP

(57) ABSTRACT

Template-fixed β-hairpin peptidomimetics of the general formulae (I), wherein Z is a template-fixed chain of 7 to 11 α-amino acid residues which, depending on their positions in the chain (counted starting from the N-terminal amino acid) are Gly, or Pro, or of certain types which, as the remaining symbols in the above formulae, are defined in the description and the claims, and salts thereof, have the property to inhibit proteases, in particular serine proteases. These β-hairpin peptidomimetics can be manufactured by a process which is based on a mixed solid- and solution phase synthetic strategy.

4 Claims, No Drawings

SEQUENCE LISTING

<160> NUMBER OF SEQ ID NOS: 15

<210> SEQ ID NO 1
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

```
<400> SEQUENCE: 1

Thr Lys Ser Ile Pro Pro Ile Pro Pro
1               5

<210> SEQ ID NO 2
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 2

Ala Lys Ser Ile Pro Pro Ile Pro Pro
1               5

<210> SEQ ID NO 3
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 3

Thr Ala Ser Ile Pro Pro Ile Pro Pro
1               5

<210> SEQ ID NO 4
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 4

Thr Lys Ala Ile Pro Pro Ile Pro Pro
1               5

<210> SEQ ID NO 5
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 5

Thr Lys Ser Ala Pro Pro Ile Pro Pro
```

-continued

```
<210> SEQ ID NO 6
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 6

Thr Lys Ser Ile Ala Pro Ile Pro Pro
1               5

<210> SEQ ID NO 7
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 7

Thr Lys Ser Ile Pro Ala Ile Pro Pro
1               5

<210> SEQ ID NO 8
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 8

Thr Lys Ser Ile Pro Pro Ala Pro Pro
1               5

<210> SEQ ID NO 9
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 9

Thr Tyr Ser Ile Pro Pro Ile Pro Pro
1               5

<210> SEQ ID NO 10
<211> LENGTH: 9
<212> TYPE: PRT
<213> ORGANISM: Artificial sequence
```

```
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 10

Thr Trp Ser Ile Pro Pro Ile Pro Pro
1               5

<210> SEQ ID NO 11
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro

<400> SEQUENCE: 11

Thr Phe Ser Ile Pro Pro Ile Pro Pro
1               5

<210> SEQ ID NO 12
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro
<220> FEATURE:
<221> NAME/KEY: MISC_FEATURE
<222> LOCATION: (9)..(9)
<223> OTHER INFORMATION: Xaa is 4-(allyloxycarbonylamino)-Pro

<400> SEQUENCE: 12

Thr Lys Ser Ile Pro Pro Ile Pro Xaa
1               5

<210> SEQ ID NO 13
<211> LENGTH: 9
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (8)..(8)
<223> OTHER INFORMATION: Pro in position 8 is D-Pro
<220> FEATURE:
<221> NAME/KEY: MISC_FEATURE
<222> LOCATION: (9)..(9)
<223> OTHER INFORMATION: Xaa is 4-(n-hexylcarbonylamino)-Pro

<400> SEQUENCE: 13

Thr Lys Ser Ile Pro Pro Ile Pro Xaa
1               5

<210> SEQ ID NO 14
<211> LENGTH: 8
<212> TYPE: PRT
```

```
<213> ORGANISM: Artificial sequence
<220> FEATURE:
<223> OTHER INFORMATION: Template-fixed peptidomimetic incorporating
      chain of 7 amino acid residues
<220> FEATURE:
<221> NAME/KEY: MISC_FEATURE
<222> LOCATION: (8)..(8)
<223> OTHER INFORMATION: Xaa is divalent radical of 5-aminomethyl-9,
      9-dimethyl-3, 6-dimethoxyxanthene-4-acetic acid

<400> SEQUENCE: 14

Thr Lys Ser Ile Pro Pro Ile Xaa
1               5

<210> SEQ ID NO 15
<211> LENGTH: 13
<212> TYPE: PRT
<213> ORGANISM: Artificial sequence
<220> FEATURE:
<223> OTHER INFORMATION: Inhibitor of protease enzymes based on
      sunflower trypsin inhibitor SFT-1 cyclic peptide
<220> FEATURE:
<221> NAME/KEY: MISC_FEATURE
<222> LOCATION: (12)..(12)
<223> OTHER INFORMATION: Pro in position 12 is D-Pro

<400> SEQUENCE: 15

Arg Cys Thr Lys Ser Ile Pro Pro Ile Cys Phe Pro Pro
1               5                   10
```

TEMPLATE-FIXED PEPTIDOMIMETICS AS INHIBITORS OF SERINE PROTEASES

CROSS-REFERENCE TO RELATED APPLICATIONS

This application is the National Stage of International Application No. PCT/EP01/14528, filed Dec. 11, 2001.

FIELD OF THE INVENTION

The present invention provides template-fixed β-hairpin peptidomimetics incorporating a template-fixed chain of 7 or 11 α-amino acid residues which, depending on their position in the chain, are Gly, or Pro, or of certain types, as defined hereinbelow. These template-fixed β-hairpin peptidomimetics are useful as inhibitors of protease enzymes. They are especially valuable as inhibitors of various serine proteases such as trypsin, human cathepsin G, and thrombin. In addition the present invention provides an efficient process by which these compounds can, if desired, be made in library-format. This library-approach constitutes an efficient novel tool to identify specific serine protease inhibitors.

BACKGROUND OF THE INVENTION

Inhibitors of proteases are emerging with promising therapeutic uses in the treatment of diseases such as cancers (P. Beckett, A. Davidson, A. H. Drummond, M. Whittaker, *Drug Disc. Today* 1996, 1, 16-26; L. L. Johnson, R. Dyer, D. J. Hupe, *Curr. Opin. Chem. Biol.* 1998, 2, 466-71; D. Leung, G. Abbenante, and D. P. Fairlie, *J. Med. Chem.* 2000, 43, 305-341), parasitic, fungal, and viral infections (e.g. schistosomiasis (M. M. Becker, S. A. Harrop, J. P. Dalton, B. H. Kalinna, D. P. McManus, D. P. Brindley, *J. Biol. Chem.* 1995, 270, 24496-501); malaria (A. M. Silva, A. Y. Lee, S. V. Gulnik, P. Maier, J. Collins, T. N. Bhat, P. J. Collins, R. E. Cachau, K. E. Luker, I. Y. Gluzman, S. E. Francis, A. Oksman, D. E. Goldberg, J. W. Erikson, *Proc. Natl. Acad. Sci. U.S.A* 1996, 93, 10034-9), *C. albicans* (C. Abad-Zapetero, R. Goldman, S. W. Muchmore, C. Hutchins, K. Stewart, J. Navaza, C. D. Payne, T. L. Ray, *Protein Sci.* 1996, 5, 640-52), HIV (A. Wlodawer, J. W. Erickson, *Annu. Rev. Biochem.* 1993, 62, 543-85; P. L. Darke, J. R. Huff, *Adv. Pharmacol.* 1994, 5, 399-454), hepatitis (J. L. Kim, K. A Morgenstern, C. Lin, T. Fox, M. D. Dwyer, J. A. Landro, S. P. Chambers, W. Markland, C. A. Lepre, E. T. O'Malley, S. L. Harbeson, C. M. Rice, M. A. Mureko, P. R. Caron, J. A. Thomson, *Cell,* 1996, 87, 343-55; R. A. Love, H. E. Parge, J. A. Wickersham, Z. Hostomsky, N. Habuka, E. W. Moomaw, T. Adachi, Z. Hostomska, *Cell,* 1996, 87, 331-342), herpes (W. Gibson, M. R. Hall, Drug. Des. Discov. 1997, 15, 39-47)], and inflammatory, immunological, respiratory (P. R. Bernstein, P. D. Edwards, J. C. Williams, *Prog. Med. Chem.* 1994, 31, 59-120; T. E. Hugli, Trends Biotechnol. 1996, 14, 409-12), cardiovascular (M. T. Stubbs, W. A. Bode, *Thromb. Res.* 1993, 69, 1-58), and neurodegenerative defects including Alzheimer's disease (R. Vassar, B. D. Bennett, S. Babu-Kahn, S. Kahn, E. A. Mendiaz, *Science,* 1999, 286, 735-41).

As most proteases bind their substrates in extended or ρ-stand conformations, good inhibitors must thus be able to mimick such a conformation. β-Hairpin mimetics are thus ideally suited to lock peptide sequences in an extended conformation.

Among proteases, serine proteases constitute important therapeutic targets. Serine proteases are classified by their substrate specificity, particularly by the type of residue found at P1, as either trypsin-like (positively charged residues Lys/Arg preferred at P1), elastase-like (small hydrophobic residues Ala/Val at P1), or chymotrypsin-like (large hydrophobic residues Phe/Tyr/Leu at P1). Serine proteases for which protease-inhibitor X-ray crystal data is available on the PDB data base (PDB: www.rcsb.org/pdb) include trypsin, α-chymotrypsin, γ-chymotrypsin, human neutrophil elastase, thrombin, subtilisin, human cytomegalovirus, proteinase A, achromobacter, human cathepsin G, glutamic acid-specific protease, carbopeptidase D, blood coagulation factor VIIa, porcine factor 1XA, mesentericopeptidase, HCV protease, and thermitase. Other serine proteases which are of therapeutic interest include tryptase, complement convertase, hepatitis C-NS3 protease. Inhibitors of thrombin (e.g. J. L. Metha, L. Y. Chen, W. W. Nichols, C. Mattsson, D. Gustaffson, T. G. P. Saldeen, *J. Cardiovasc. Pharmacol.* 1998, 31, 345-51; C. Lila, P. Gloanec, L. Cadet, Y. Herve, J. Fournier, F. Leborgne, T. J. Verbeuren, G. DeNanteuil, *Synth. Comm.* 1998, 28, 4419-29) and factor Xa (e.g. J. P. Vacca, *Annu. Rep. Med. Chem.* 1998, 33, 81-90) are in clinical evaluation as antithrombotics, inhibitors of elastase (J. R. Williams, R. C. Falcone, C. Knee, R. L. Stein, A. M. Strimpler, B. Reaves, R. E. Giles, R. D. Krell, *Am. Rev. Respir. Dis.* 1991, 144, 875-83) are in clinical trials for emphysema and other pulmonary diseases whereas tryptase inhibitors are currently in phase II clinical trials for asthma (C. Seife, *Science* 1997, 277, 1602-3). Finally, cathepsin G and elastase are intimately involved in the modulation of activities of cytokines and their receptors. Particularly at sites of inflammation, high concentration of cathepsin G, elastase and proteinase 3 are released from infiltrating polymorphonuclear cells in close temporal correlation to elevated levels of inflammatory cytokines, strongly indicating that these proteases are involved in the control of cytokine bioactivity and availability (U. Bank S. Ansorge, *J. Leukoc. Biol.* 2001, 69, 177-90). Thus inhibitors of thrombin and cathepsin G constitute valuable targets for novel drug candidates.

Of the many occurring proteinaceous serine protease inhibitors, one is a 14 amino acid cyclic peptide from sunflower seeds, termed sunflower trypsin inhibitor (SFTI-1) (S. Luckett, R. Santiago Garcia, J. J. Barker, A. V. Konarev, P. R. Shewry, A. R. Clarke, R. L. Brady, *J. Mol. Biol.* 1999, 290, 525-533; Y. -Q. Long, S. -L. Lee, C. -Y. Lin, I. J. Enyedy, S. Wang, P. Li, R. B. Dickson, P. P. Roller, *Biorg. & Med. Chem. Lett.* 2001, 11, 2515-2519), which shows both sequence and conformational similarity with the trypsin-reactive loop of the Bowman-Birk family of serine protease inhibitors. The inhibitor adopts a β-hairpin conformation when bound to the active site of bovine β-trypsin. SFTI-1 inhibited β-trypsin ($K_i$<0.1 nM), cathepsin G, elastase ($K_i$~105 µM), chymotrypsin ($K_i$~7.4 µM) and thrombin ($K_i$~136 mM).

We illustrate here an approach to inhibitor design which involves transplanting the β-hairpin loop from the naturally occurring peptide onto a hairpin-inducing template. Based on the well defined 3D-structure of the β-hairpin mimetics libraries of compounds can be designed which ultimately can lead to novel inhibitors showing different specificity profiles towards several classes of proteases.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), but such molecules have not previously been evaluated for development of peptides which inhibit proteases and constitute mimetics of extended peptide conformations. However, the ability to generate β-hairpin peptidomimetics using combinatorial and parallel synthesis methods has now been established (L. Jiang, K. Moehle, B.

Dhanapal, D. Obrecht, J. A. Robinson, *Helv. Chim. Acta.* 2000, 83, 3097-3112). This technology allows to rapidly synthesise libraries of protease inhibitors and to explore key residues which determine the specificity for a given serine protease.

SUMMARY OF THE INVENTION

The β-hairpin peptidomimetics of the present invention are compounds of the general formula

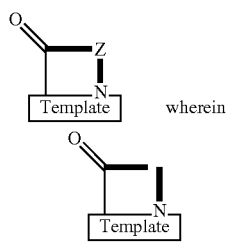

(I)

wherein

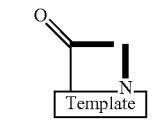

is a group of one of the formulae

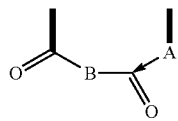

(a1)

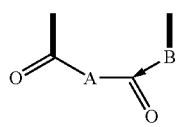

(a2)

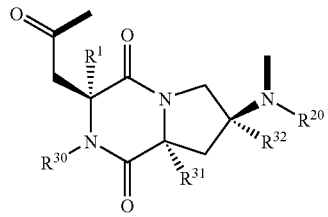

(b1)

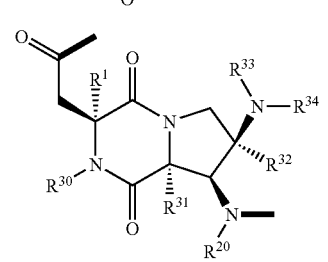

(b2)

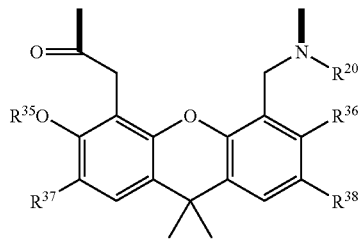

c1)

-continued

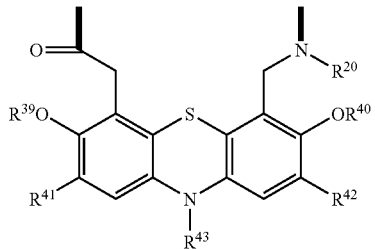

(c2)

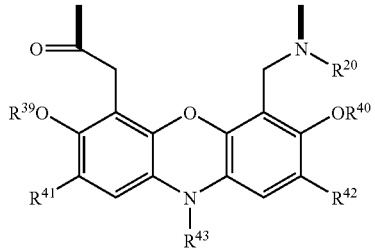

(c3)

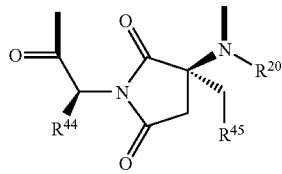

(d)

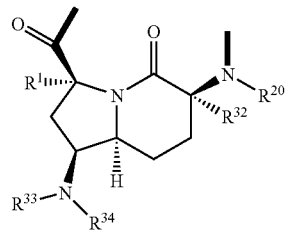

(e1)

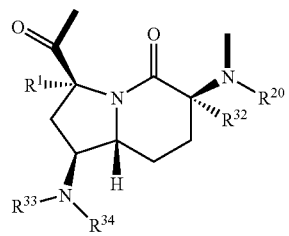

(e2)

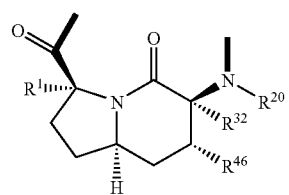

(e3)

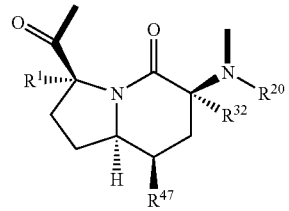

(e4)

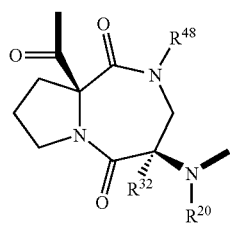
(f)
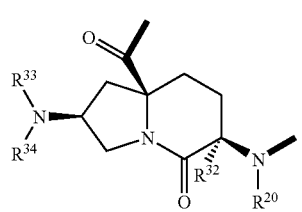
(g)
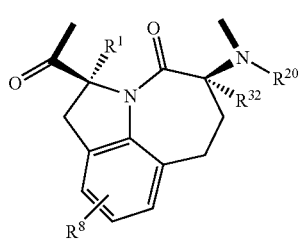
(h)
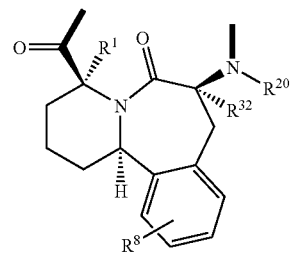
(i1)
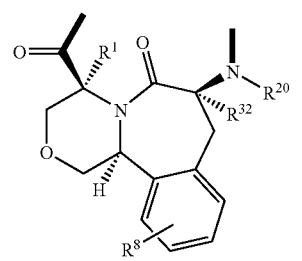
(i2)
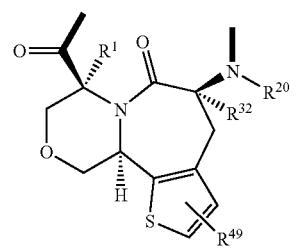
(i3)
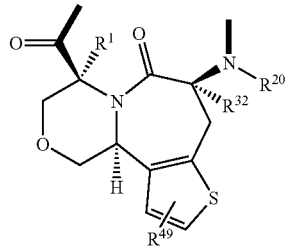
(i4)
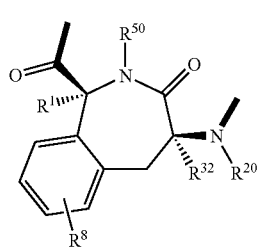
(j)
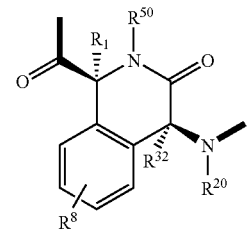
(k)
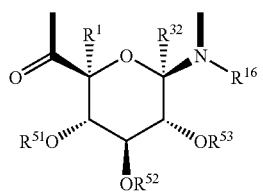
(l)
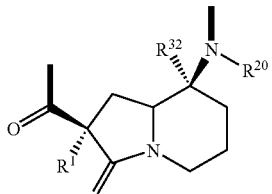
(m)
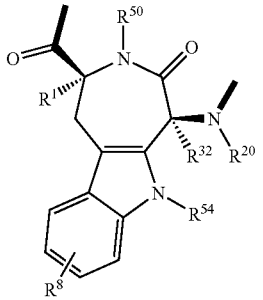
(n)

-continued
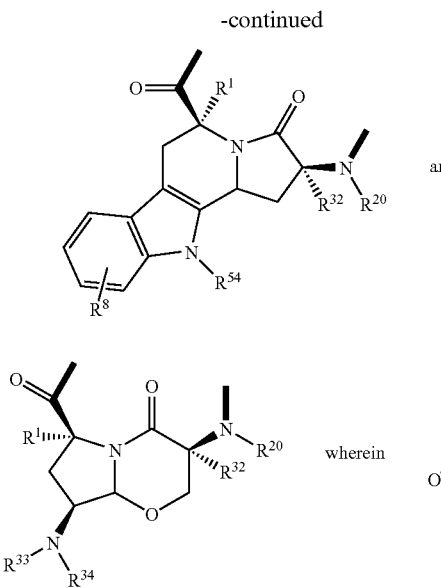
(o)
and
(p)
wherein
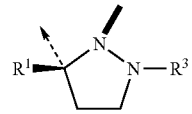
is the residue of an L-α-amino acid with B being a residue of formula —NR$^{20}$CH(R$^{71}$)— or the enantiomer of one of the groups A1 to A69 as defined hereinafter;
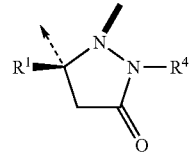
is a group of one of the formulae
A1
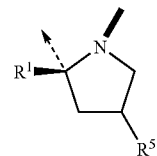
A2
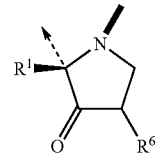
A3
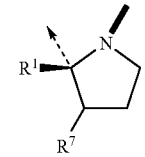
A4
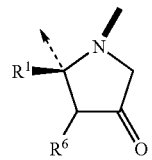
A5
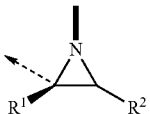
-continued
A6
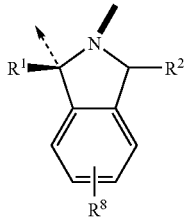
A7
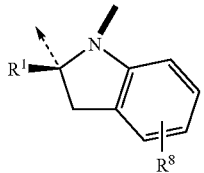
A8
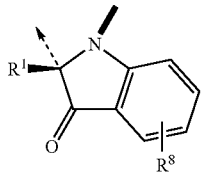
A9
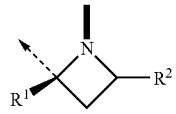
A10
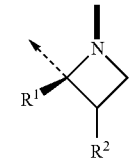
A11
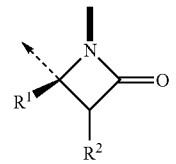
A12
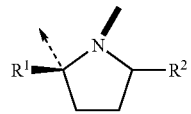
A13
A14

-continued
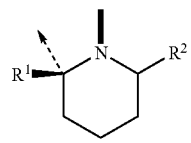 A15
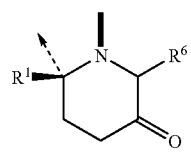 A16
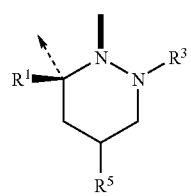 A17
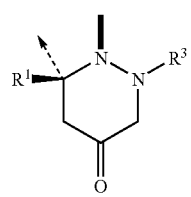 A18
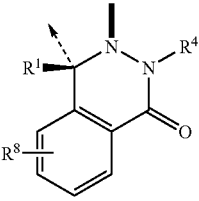 A19
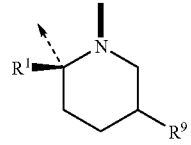 A20
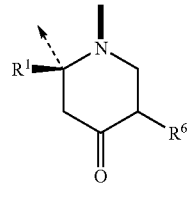 A21
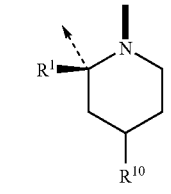 A22
-continued
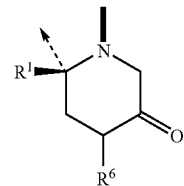 A23
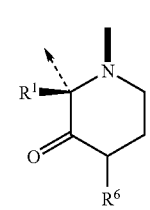 A24
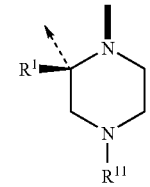 A25
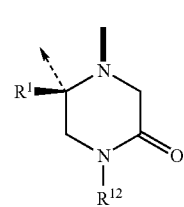 A26
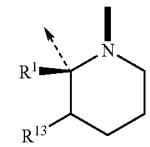 A27
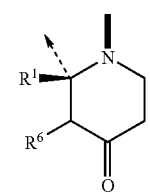 A28
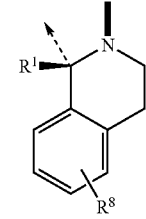 A29

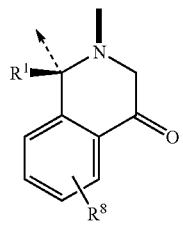 A30
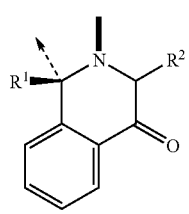 A31
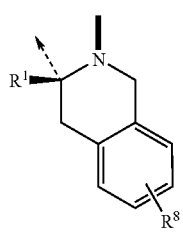 A32
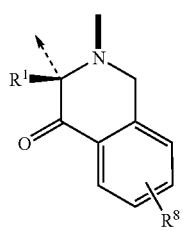 A33
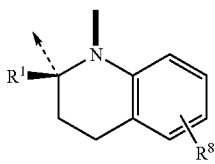 A34
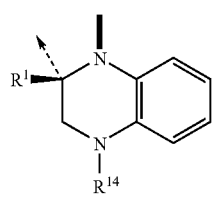 A35
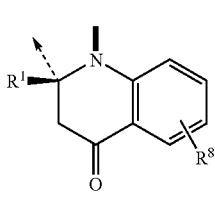 A36
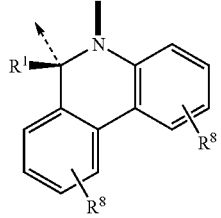 A37
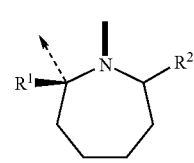 A38
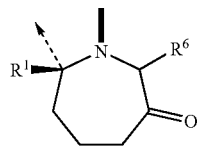 A39
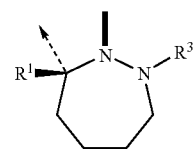 A40
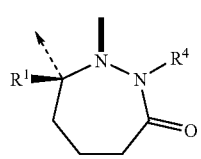 A41
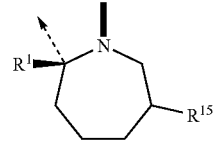 A42
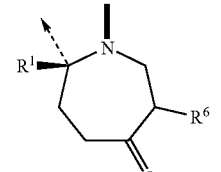 A43
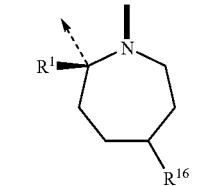 A44

-continued
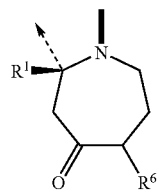 A45
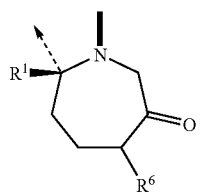 A46
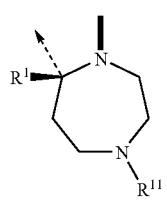 A47
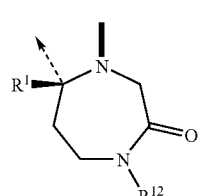 A48
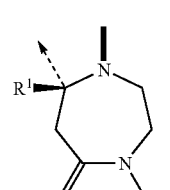 A49
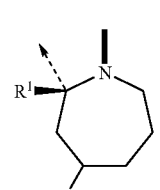 A50
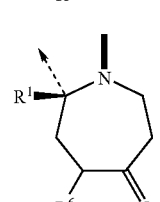 A51
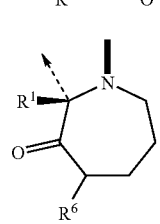 A52
-continued
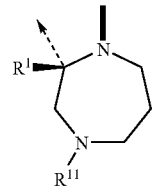 A53
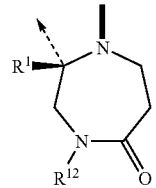 A54
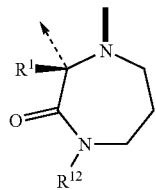 A55
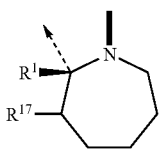 A56
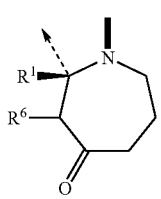 A57
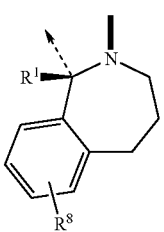 A58
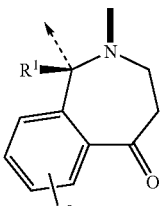 A59
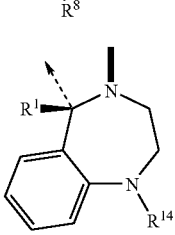 A60

-continued

A61, A62, A63, A64, A65, A66, A67, A68, A69, A70, A71, A72, A73, A74, A75

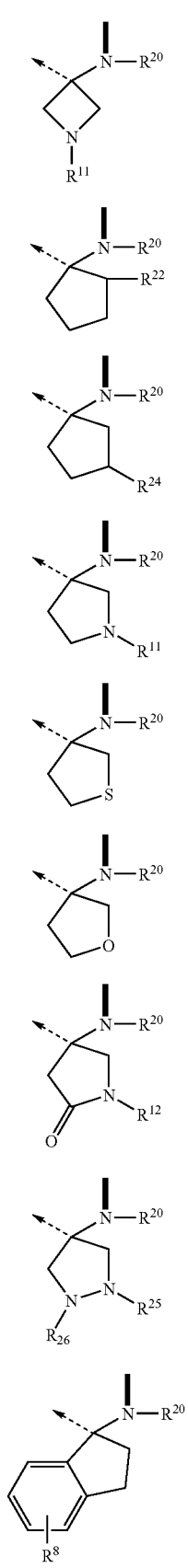

-continued

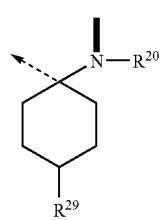 A93

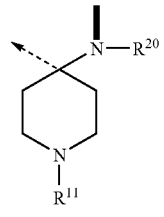 A94

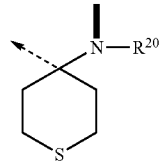 A95

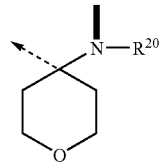 A96

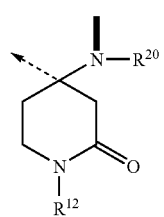 A97

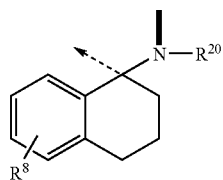 A98

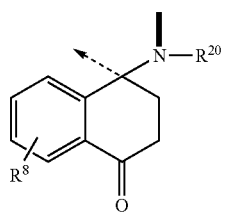 A99

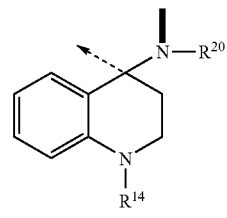 A100

-continued

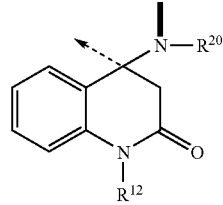 A101

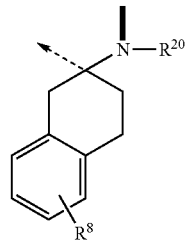 A102

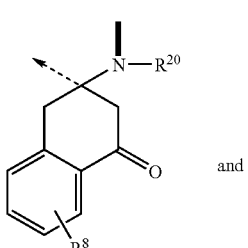 A103 and

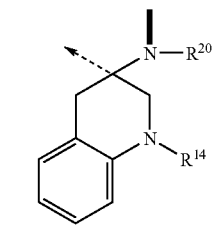 A104

$R^1$ is H; lower alkyl; or aryl-lower alkyl;

$R^2$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{78}$; —$(CH_2)_m(CHR^{61})_sNR^{20}CONR^{33}R^{78}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^3$ is H; alkyl; alkenyl; —$(CH_2)_m(CHR^{61})_sOR^{55}$; —$(CH_2)_m(CHR^{61})_sSR^{56}$; —$(CH_2)_mCHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_m(CHR^{61})_sC_6H_4R^8$;

$R^4$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_m(CHR^{61})_sOCONR^{33}R^{78}$; —$(CH_2)_m(CHR^{61})_sNR^2CONR^{33}R^{78}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^7$ is alkyl; alkenyl; —$(CH_2)_q(CHR^{61})_sOR^{55}$; —$(CH_2)_q(CHR^{61})_sNR^{33}R^{34}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_rCHR^{61})_sC_6H_4R^8$;

$R^8$ is H; Cl; F; $CF_3$; $NO_2$; lower alkyl; lower alkenyl; aryl; aryl-lower alkyl; —$(CH_2)_o(CHR^{61})_sOR^{55}$; —$(CH_2)_o(CHR^{61})_sSR^{56}$; —$(CH_2)_o(CHR^{61})NR^{33}R^{34}$; —$(CH_2)_o(CHR^{61})_sOCONR^{33}R^{78}$; —$(CH_2)_o(CHR^{61})_sNR^{20}CONR^{33}R^{78}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sCOR^{64}$;

$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{10}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{11}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_mCHR^{61})_sOCONR^{33}R^{78}$; —$(CH_2)_m(CHR^{61})_sNR^{20}CONR^{33}R^{78}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})$; —$(CH_2)_o(CHR^{61})_sSO_2R^{62}$; or —$(CH_2)_m(CHR^{61})_sC_6H_4R^8$;

$R^{12}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_q(CHR^{61})_sC_6H_4R^8$;

$R^{13}$ is alkyl; alkenyl; —$(CH_2)_q(CHR^{61})_sOR^{55}$; —$(CH_2)_q(CHR^{61})_sSR^{56}$; —$(CH_2)_q(CHR^{61})_sNR^{33}R^{34}$; —$(CH_2)_q(CHR^{61})_sCOOR^{57}$; —$(CH_2)_q(CHR^{61})_sCONR^{58}R^{59}$; —$(CH_2)_q(CHR^{61})_sPO(OR^{60})_2$; —$(CH_2)_q(CHR^{61})_sSO_2R^{62}$; or —$(CH_2)_q(CHR^{61})_sC_6H_4R^8$;

$R^{14}$ is H; alkyl; alkenyl; —$(CH_2)_m(CHR^{61})_sOR^{55}$; —$(CH_2)_m(CHR^{61})_sNR^{33}R^{34}$; —$(CH_2)_q(CHR^{61})_sCOOR^{57}$; —$(CH_2)_q(CHR^{61})_sCONR^{58}R^{59}$; —$(CH_2)_q(CHR^{61})_sPO(OR^{60})_2$; —$(CH_2)_q(CHR^{61})_sSOR^{62}$; or —$(CH_2)_q(CHR^{61})_sC_6H_4R^8$;

$R^{15}$ is allyl; alkenyl; —$(CH_2)_o(CHR^{61})_sOR^{55}$; —$(CH_2)_o(CHR^{61})_sR^{56}$; —$(CH_2)_q(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{16}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{17}$ is alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_q(CHR^{61})_sCOOR^{57}$; —$(CH_2)_q(CHR^{61})_sCONR^{58}R^{59}$; —$(CH_2)_q(CHR^{61})_sPO(OR^{60})_2$; —$(CH_2)_q(CHR^{61})_sSO_2R^{62}$; or —$(CH_2)_q(CHR^{61})_sC_6H_4R^8$;

$R^{18}$ is alkyl; alkenyl; —$(CH_2)_p(CHR^{61})_sOR^{55}$; —$(CH_2)_p(CHR^{61})_sSR^{56}$; —$(CH_2)_p(CHR^{61})_sR^{33}R^{34}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{19}$ is lower alkyl; —$(CH_2)_p(CHR^{61})_sOR^{55}$; —$(CH_2)_p(CHR^{61})_sSR^{56}$; —$(CH_2)_p(CHR^{61})_sNR^{33}R^{34}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{64}$; or —$(CH_2)_o(CHR^{61})_sC_6H_4R^8$; or $R^{18}$ and $R^{19}$ taken together can form: —$(CH_2)_{2-6}$—; —$(CH_2)_2O(CH_2)_2$—; —$(CH_2)_2S(CH_2)_2$—; or —$(CH_2)_2NR^{34}(CH_2)_2$—;

$R^{20}$ is H; alkyl; alkenyl; or aryl-lower alkyl;

$R^{21}$ is H; alkyl; alkenyl; —$(CH_2)_o(CHR^{61})_sOR^{55}$; —$(CH_2)_q(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{22}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{23}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{24}$ is alkyl; alkenyl; —$(CH_2)_o(CHR^{61})_sOR^{55}$; —$(CH_2)_o(CHR^{61})_sR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{25}$ is H; alkyl; alkenyl; —$(CH_2)_m(CHR^{61})_sOR^{55}$; —$(CH_2)_o(CHR^{61})_sSR^{56}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{26}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$; or $R^{25}$ and $R^{26}$ taken together can form: —$(CH_2)_{2-6}$—; —$(CH_2)_rO(CH_2)_r$—; —$(CH_2)_rS(CH_2)_r$—; or —$(CH_2)_rNR^{34}(CH_2)_r$—;

$R^{27}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{28}$ is alkyl; alkenyl; —$(CH_2)_o(CHR^{61})_s$—$OR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{29}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{30}$ is H; alkyl; alkenyl; or aryl-lower alkyl;

$R^{31}$ is alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{32}$ is H; lower alkyl; or aryl-lower alkyl;

$R^{33}$ is H; alkyl, alkenyl; —$(CH_2)_m(CHR^{61})_sOR^{55}$; —$(CH_2)_o(CHR^{61})_sSR^{56}$; —$(CH_2)_m(CHR^{61})_sNR^{33}R^{63}$; —$(CH_2)_m(CHR^{61})_sOCONR^{34}R^{78}$; —$(CH_2)_m(CHR^{61})_sNR^{20}CONR^{34}R^{78}$; —$(CH_2)_o(CHR^{61})_sCOR^{64}$; —$(CH_2)_o(CHR^{61})$—$CONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{34}$ is H; lower alkyl; aryl, or aryl-lower allyl;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl, alkenyl; —$(CH_2)_o(CHR^{61})_sOR^{55}$; —$(CH_2)_p(CHR^{61})_sNR^{33}R^{34}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{37}$ is H; F; Br; Cl; $NO_2$; $CF_3$; lower alkyl; —$(CH_2)_p(CHR^{61})_sOR^{55}$; —$(CH_2)_p(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60}(_2$; —$(CH_2)_o(CHR^{61})_sSO_2R^{62}$; or —$(CH_2)_o(CHR^{61})_sC_6H_4R^8$;

$R^{38}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{42}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{43}$ is H; alkyl; alkenyl; —$(CH_2)_m(CHR^{61})_sOR^{55}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{44}$ is alkyl; alkenyl; —$(CH_2)_r(CHR^{61})_sOR^{55}$; —$(CH_2)_r(CHR^{61})_sSR^{56}$; —$(CH_2)_r(CHR^{61})_sNR^{33}R^{34}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_r(CHR^{61})_sC_6H_4R^8$;

$R^{45}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_s(CHR^{61})_sSO_2R^{62}$; or —$(CH_2)_o(CHR^{61})_sC_6H_4R^8$;

$R^{46}$ is H; alkyl; alkenyl; or —$(CH_2)_o(CHR^{61})_pC_6H_4R^8$;

$R^{47}$ is H; alkyl; alkenyl; or —$(CH_2)_o(CHR^{61})_sOR^{55}$;

$R^{48}$ is H; lower alkyl; lower alkenyl; or aryl-lower alkyl;

$R^{49}$ is H; alkyl; alkenyl; —$(CHR^{61})_sCOOR^{57}$; $(CHR^{61})_sCONR^{58}R^{59}$; $(CHR^{61})_sPO(OR^{60})_2$; —$(CHR^{61})_sSOR^{62}$; or —$(CHR^{61})_sC_6H_4R^8$;

$R^{50}$ is H; lower alkyl; or aryl-lower alkyl;

$R^{51}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{52}$ is H; alkyl; alkenyl; —$(CH_2)_m(CHR^{61})_sOR^{55}$; —$(CH_2)_s(CHR^{61})_sSR^{56}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{53}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{54}$ is H; alkyl; alkenyl; —$(CH_2)_m(CHR^{61})_sOR^{55}$; —$(CH_2)_m(CHR^{61})_sNR^{33}R^{34}$; —$(CH_2)_o(CHR^{61})COOR^{57}$; —$(CH_2)_o(CHR^{61})_sCONR^{58}R^{59}$; or —$(CH_2)_o(CHR^{61})_sC_6H_4R^8$;

$R^{55}$ is H; lower alkyl; lower alkenyl; aryl-lower alkyl; —$(CH_2)_m(CHR^{61})_sOR^{57}$; —$(CH_2)_m(CHR^{61})_sNR^{34}R^{63}$; —$(CH_2)_o(CHR^{61})_s$—$COR^{64}$; —$(CH_2)_o(CHR^{61})COOR^{57}$; or —$(CH_2)_o(CHR^{61})_sCONR^{58}R^{59}$;

$R^{56}$ is H; lower alkyl; lower alkenyl; aryl-lower alkyl; —$(CH_2)_m(CHR^{61})_sOR^{57}$; —$(CH_2)_m(CHR^{61})_sNR^{34}R^{63}$; —$(CH_2)_o(CHR^{61})_s$—$COR^{64}$; or —$(CH_2)_o(CHR^{61})_sCONR^{58}R^{59}$;

$R^{57}$ is H; lower alkyl; lower alkenyl; aryl lower alkyl; or heteroaryl lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: —$(CH_2)_{2-6}$—; —$(CH_2)_2 O(CH_2)_2$—; —$(CH_2)_2S(CH_2)_2$—; or —$(CH_2)_2NR^{34}(CH_2)_2$—;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; —$(CH_2)_mOR^{55}$; —$(CH_2)_mNR^{33}R^{34}$; —$(CH_2)_oCOOR^{37}$; —$(CH_2)_oNR^{58}R^{59}$; or —$(CH_2)_oPO(COR^{60})_2$;

$R^{62}$ is lower alkyl; lower alkenyl; aryl, heteroaryl; or aryl-lower alkyl;

$R^{63}$ is H; lower alkyl; lower alkenyl; aryl, heteroaryl; aryl-lower alkyl; heteroaryl-lower alkyl; —$COR^{64}$; —$COOR^{57}$; —$CONR^{58}R^{59}$; —$SO_2R^{62}$; or —$PO(OR^{60})_2$;

$R^{64}$ is H; lower alkyl; lower alkenyl; aryl; heteroaryl; aryl-lower alkyl; heteroaryl-lower alkyl; —$(CH_2)_p(CHR^{61})_sOR^{65}$; —$(CH_2)_p(CHR^{61})_sSR^{66}$; or —$(CH_2)_p(CHR^{61})_sNR^{34}R^{63}$;

$R^{65}$ is H; lower alkyl; lower alkenyl; aryl, aryl-lower alkyl; heteroaryl-lower alkyl; —$COR^{57}$; —$COOR^{57}$; or —$CONR^{58}R^{59}$;

$R^{66}$ is H; lower alkyl; lower alkenyl; aryl; aryl-lower alkyl; heteroaryl-lower alkyl; or —$CONR^{58}R^{59}$;

m is 2-4; o is 0-4; p is 1-4; q is 0-2; r is 1 or 2; s is 0 or 1;

Z is a chain of n α-amino acid residues, n being the integer 7 or 11, the positions of said amino acid residues in said chain being counted starting from the N-terminal amino acid, whereby these amino acid residues are, depending on their position in the chains, Gly, or Pro, or of formula -A-CO—, or of one of the types

C: —$NR^{20}CH(R^{72})CO$—;

D: —$NR^{20}CH(R^{73})CO$—;

E: —$NR^{20}CH(R^{74})CO$—;

F: —$NR^{20}CH(R^{84})CO$—; and

H: —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(—(CH$_2$)$_p$NR$^{20}$CO(CH$_2$)$_p$—CH(CO—)—NR$^{20}$—; and —NR$^{20}$—CH(CO—)—(—(CH$_2$)$_p$NR$^{20}$CONR$^{20}$(CH$_2$)$_p$—CH(CO—)—NR$^{20}$—;

R$^{71}$ is H; lower alkyl; lower alkenyl; —(CH$_2$)$_p$(CHR$^{61}$)$_s$OR$^{75}$; —(CH$_2$)$_p$(CHR$^{61}$)$_s$SR$^{75}$; —(CH$_2$)$_p$NR$^{78}$R$^{79}$; —(CH$_2$)$_o$(CHR$^{61}$)$_s$COOR$^{75}$; —(CH$_2$)$_p$CONR$^{78}$R$^{79}$; —(CH$_2$)$_p$PO(OR$^{62}$)$_2$; —(CH$_2$)$_p$SO$_2$R$^{62}$; or —(CH$_2$)$_o$—C$_6$R$^{67}$R$^{68}$R$^{69}$R$^{70}$R$^{76}$;

R$^{72}$ is H; lower alkyl; lower alkenyl; —(CH$_2$)$_p$(CHR$^{61}$)$_s$OR$^{85}$; or —(CH$_2$)$_p$(CHR$^{61}$)$_s$SR$^{85}$;

R$^{73}$ is —(CH$_2$)$_o$R$^{77}$; —(CH$_2$)$_r$O(CH$_2$)$_o$R$^{77}$; —(CH$_2$)$_r$S(CH$_2$)$_o$R$^{77}$; or —(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$C(=NR$^{80}$)NR$^{78}$R$^{79}$; —(CH$_2$)$_p$C(=NOR$^{50}$)NR$^{78}$R$^{79}$; —(CH$_2$)$_p$C(=NNR$^{78}$R$^{79}$)NR$^{78}$R$^{79}$; —(CH$_2$)$_p$NR$^{80}$C(=NR$^{80}$)NR$^{78}$R$^{79}$; —(CH$_2$)$_p$C$_6$H$_4$NR$^{78}$R$^{79}$; —(CH$_2$)$_p$C$_6$H$_4$C(=NR$^{80}$)NR$^{78}$R$^{79}$; —(CH$_2$)$_p$C$_6$H$_4$C(=NOR$^{50}$)NR$^{78}$R$^{79}$; —(CH$_2$)$_p$C$_6$H$_4$C(=NRR$^{78}$R$^{79}$)NR$^{78}$R$^{79}$; —(CH$_2$)$_p$C$_6$H$_4$NR$^{80}$C(=NR$^{80}$)NR$^{78}$R$^{79}$; —(CH$_2$)$_r$O(CH$_2$)$_m$NR$^{78}$R$^{79}$; —(CH$_2$)$_r$O(CH$_2$)$_p$C(=NR$^{80}$)NR$^{78}$R$^{79}$; —(CH$_2$)$_r$O(CH$_2$)$_p$C(=NOR$^{50}$)NR$^{78}$R$^{79}$; —(CH$_2$)$_r$O(CH$_2$)$_p$C(=NNR$^{78}$R$^{79}$)NR$^{78}$R$^{79}$; —(CH$_2$)$_r$O(CH$_2$)$_m$NR$^{80}$C(=NR$^{80}$)NR$^{78}$R$^{79}$; —(CH$_2$)$_r$O(CH$_2$)$_p$C$_6$H$_4$CNR$^{78}$R$^{79}$; —(CH$_2$)$_r$O(CH$_2$)$_p$C$_6$H$_4$C(=NR$^{80}$)NR$^{78}$R$^{79}$; —(CH$_2$)$_r$O(CH$_2$)$_p$C$_6$H$_4$C(=NOR$^{50}$)NR$^{78}$R$^{79}$; —(CH$_2$)$_r$O(CH$_2$)$_p$C$_6$H$_4$C(=NNR$^{78}$R$^{79}$)NR$^{78}$R$^{79}$; —(CH$_2$)$_r$O(CH$_2$)$_p$C$_6$H$_4$NR$^{80}$C(=NR$^{80}$)NR$^{78}$R$^{79}$; —(CH$_2$)$_r$S(CH$_2$)$_m$NR$^{78}$R$^{79}$; —(CH$_2$)$_r$S(CH$_2$)$_p$C(=NR$^{80}$)NR$^{78}$R$^{79}$; —(CH$_2$)$_p$C(=NOR$^{50}$)NR$^{78}$R$^{79}$; —(CH$_2$)$_r$S(CH$_2$)$_p$C(=NNR$^{78}$R$^{79}$)NR$^{78}$R$^{79}$; —(CH$_2$)$_r$S(CH$_2$)$_m$NR$^{80}$C(=NR$^{80}$)NR$^{78}$R$^{79}$; —(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$NR$^{78}$R$^{79}$; —(CH$_2$)$_r$S(CH$_2$)$_p$C$_6$H$_4$C(=NOR$^{50}$)NR$^{78}$R$^{79}$; —(CH$_2$)$_r$S(CH$_2$)$_p$C$_6$H$_4$C(=NNR$^{78}$R$^{79}$)NR$^{78}$R$^{79}$; —(CH$_2$)$_r$S(CH$_2$)$_p$C$_6$H$_4$NR$^{80}$C—(=NR$^{80}$)NR$^{78}$R$^{79}$; —(CH$_2$)$_p$NR$^{80}$CONR$^{78}$R$^{79}$; or —(CH$_2$)$_p$C$_6$H$_4$NR$^{80}$CONR$^{78}$R$^{79}$;

R$^{75}$ is lower alkyl; lower alkenyl; or aryl-lower alkyl;

R$^{76}$ is H; lower alkyl; lower alkenyl; aryl-lower alkyl; —(CH$_2$)$_o$OR$^{72}$; —(CH$_2$)$_o$SR$^{72}$; —(CH$_2$)$_o$R$^{33}$R$^{34}$; —(CH$_2$)$_o$COOR$^{75}$; —(CH$_2$)$_o$CONR$^{58}$R$^{59}$; —(CH$_2$)$_o$PO(OR$^{60}$)$_2$; —(CH$_2$)$_p$SO$_2$R$^{62}$; or —(CH$_2$)$_o$COR$^{64}$;

R$^{77}$ is —C$_6$R$^{67}$R$^{68}$R$^{69}$R$^{70}$R$^{76}$; or a heteroaryl group of one of the formulae

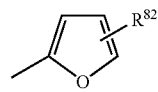 H1

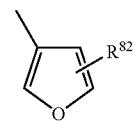 H2

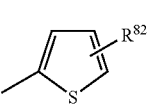 H3

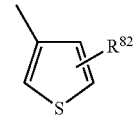 H4

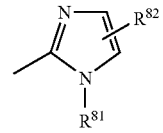 H5

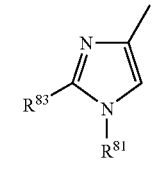 H6

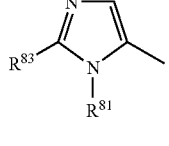 H7

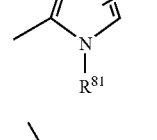 H8

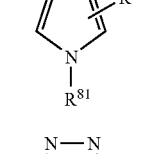 H9

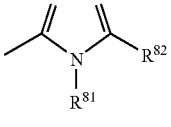 H10

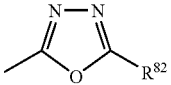 H11

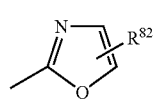 H12

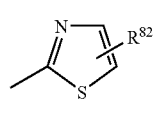 H13

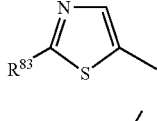 H14

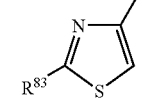 H15

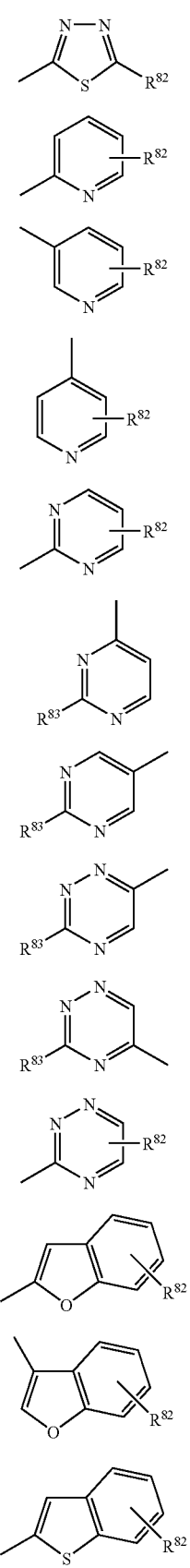
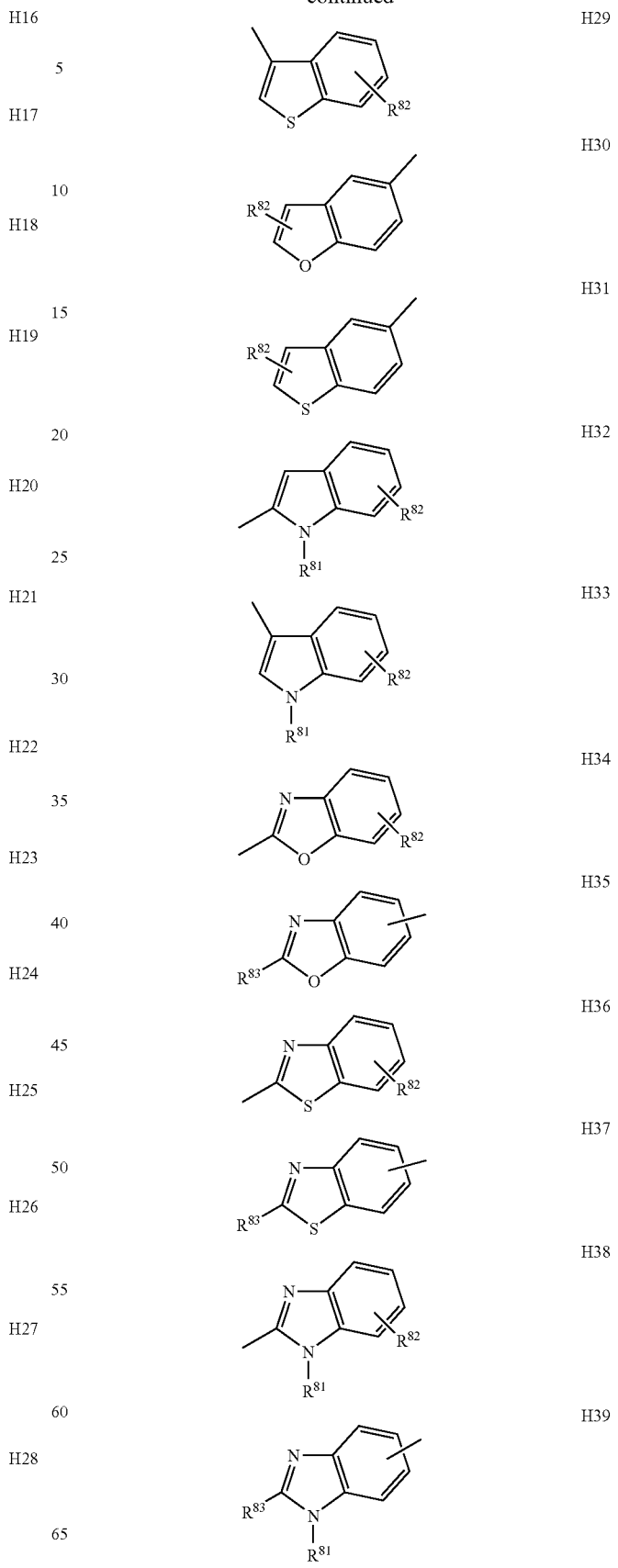

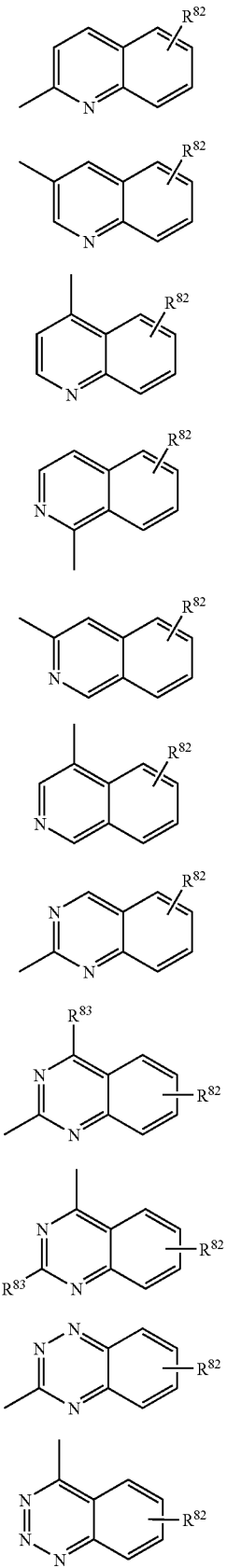

$R^{78}$ is H; lower alkyl; aryl; or aryl-lower alkyl;
$R^{79}$ is H; lower all; aryl; or aryl-lower alkyl; or
$R^{78}$ and $R^{79}$, taken together, can be —$(CH_2)_{2-7}$—; —$(CH_2)_2O(CH_2)_2$—, or —$(CH_2)_2NR^{33}(CH_2)_2$—;
$R^{80}$ is H; or lower alkyl;
$R^{81}$ is H; lower alkyl; or aryl-lower alkyl;
$R^{82}$ is H; lower alkyl; aryl; heteroaryl; or aryl-lower alkyl;
$R^{83}$ is H; lower alkyl; aryl; or —$NR^{78}R^{79}$;
$R^{84}$ is —$(CH_2)_m(CHR^{61})_sOH$; —$(CH_2)_pCONR^{78}R^{79}$; —$(CH_2)_pNR^{80}CONR^{78}R^{79}$; —$(CH_2)_pC_6H_4CONR^{78}R^{79}$; —$(CH^2)_pCOOR^{80}$ or —$(CH_2)_pC_6H_4NR^{80}CONR^{78}R^{79}$;
$R^{85}$ is lower alkyl; or lower alkenyl;

with the proviso that in said chain of n α-amino acid residues Z
  if n is 7, the amino acid residues in positions 1 to 7 are:
    P1: of type C or of type F or of type D;
    P2: of type E or of type C or of type D or of type F;
    P3: of type F or of type C, or the residue is Gly or Pro;
    P4: of type C or of type D or of type F, or the residue is Gly or Pro;
    P5: of type F or of formula -A-CO—, or the residue is Gly or Pro;
    P6: of type C or of type E or of formula -A-CO—, or the residue is Pro;
    P7: of type C or of type F or of type D;
  if n is 11, the amino acid residues in positions 1 to 11 are:
    P1: of type E or of type F or of type C;
    P2: of type C or of type F or of type E;
    P3: of type C or of type F;
    P4: of type E or of type C or of type D or of type F, or the residue is Gly or Pro;
    P5: of type F or of type C, or the residue is Gly or Pro;
    P6: of type C or of type D or of type F, or the residue is Gly or Pro;
    P7: of type F or of formula -A-CO—, or the residue is Gly or Pro;
    P8: of type C or of type E or of formula -A-CO—, or the residue is Gly or Pro;
    P9: of type C or of type F;
    P10: of type F or of type C;
    P11: of type D or of type or of type F or of type C; or
    P2 and P10, taken together, can form a group of type H;

and pharmaceutically acceptable salts thereof

In accordance with the present invention these β-hairpin peptidomimetics can be prepared by a process which comprises
(a) coupling an appropriately functionalized solid support with an appropriately N-protected derivative of that amino acid which in the desired end-product is in position n/2+½ or n/2−½, any functional group which may be present in said N-protected amino acid derivative being likewise appropriately protected;
(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating, if necessary, steps (c) and (d) until the N-terminal amino acid residue has been introduced;

(f) coupling the product thus obtained to a compound of the general formula

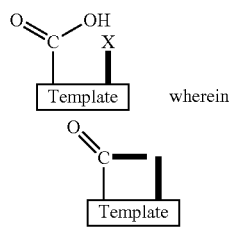  wherein is as defined above and X is an N-protecting group or, if

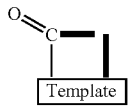

is to be group (a1) or (a2), above, alternatively (fa) coupling the product obtained in step (d) or (e) with an appropriately N-protected derivative of an ammo acid of the general formula

 HOOC-B-H    III or

 HOOC-A-H    IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, m, any functional group which may be present in said N-protected amino acid derivative being likewise appropriately protected;

(g) removing the N-protecting group from the product obtained in step (f) or (fc);

(h) coupling the product thus obtained to an appropriately N-protected derivative of that amino acid which in the desired end-product is in position n, any functional group which may be present in said N-protected amino acid derivative being likewise appropriately protected;

(i) removing the N-protecting group from the product thus obtained;

(j) coupling the product thus obtained to an appropriately N-protected derivative of that amino acid which in the desired end-product is one position farther away from position n, any functional group which may be present in said N-protected amino acid derivative being likewise appropriately protected;

(k) removing the N-protecting group from the product thus obtained;

(l) repeating, if necessary, steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if desired, forming an interstrand linkage between side-chains of appropriate amino acid residues at opposite positions of the β-strand region;

(r) removing any protecting groups present on functional groups of any members of the chain of amino acid residues and, if desired, any protecting group(s) which may in addition be present in the molecule; and (r) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

DETAILED DESCRIPTION OF PREFERRED EMBODIMENTS

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element —A—CO— designates amino acid building blocks which in combination with the structural element —B—CO— form templates (a1) and (a2). Templates (a) through (p) constitute building blocks which have an N-terminus and a c-terminus oriented in space in such a way that the distance between those two groups may lie between 4.0-5.5A. A peptide chain is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5A the template will induce the H-bond network necessary for the formation of a β-hairpin conformation in the peptide chain Z. Thus template and peptide chain form a β-hairpin mimetic. The β-hairpin conformation is highly relevant for the protease inhibitory activities of the β-hairpin mimetics of the present invention. The β-hairpin stabilizing conformational properties of the templates (a) through (p) play a key role not only for protease inhibitory activity but also for the synthesis process defined hereinabove, as incorporation of the templates near the middle of the linear protected peptide precursors enhance significantly cyclization yields.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block -B-CO— of (L)-configuration. Preferred combinations for templates (a1) are -$^D$A1—CO—$^L$B—CO— to $^D$A69—CO—$^L$B—CO—. Thus, for example, $^D$Pro-$^L$Pro constitutes the prototype of templates (a1). Less preferred, but possible are combinations where templates (a2) are -$^L$A1—CO—$^D$B—CO— to $^L$A69—CO—$^D$B—CO—. Thus, for example, $^L$Pro-$^D$Pro constitutes a less preferred prototype of template (a2).

It will be appreciated that building blocks —A1—CO— to —A69CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1—A69 are shown in (D)-configuration which, for $R^1$ being H and methyl, corresponds to the (2)-configuration. Depending on the priority of other values for $R^1$ according to the Cahn, Ingold and Prelog-rules, this configuration may also have to be expressed as (S).

In addition to $R^1$ building blocks —A1—CO— to —A69—CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_mOR^{55}$ (where $R^{55}$: lower alkyl; or lower alkenyl); $(CH_2)_mSR^{56}$ (where $R^{56}$: H; or lower alkyl; or lower alkenyl); $(CH_2)_mNR^{33}R^{34}$ (where $R^{33}$: lower alkyl; or lower alkenyl; $R^{34}$: H; or lower alkyl); $(CH_2)_mOCONR^{33}R^{78}$ (where $R^{33}$: lower alkyl; or lower alkenyl; $R^{78}$: H; or lower alkyl); $(CH_2)_mNR^{20}CONR^{33}R^{78}$ (where $R^{20}$: H or lower alkyl; $R^{33}$: lower alkyl; or lower alkenyl; $R^{78}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_oCOOR^{57}$ (where $R^{57}$: lower; or lower alkenyl); $(CH_2)_oCONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; $(CH_2)_mOR^{55}$ (where $R^{55}$: lower alkyl; or lower alkenyl); $(CH_2)_mSR^{56}$ (where $R^{56}$: H; or lower alkyl; or lower alkenyl); $(CH_2)_mNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; $(CH_2)_mOR^{55}$ (where $R^{55}$: lower alkyl; or lower alkenyl); $(CH_2)_mSR^{56}$ (where $R^{56}$: H; or lower alkyl; or lower alkenyl); $(CH_2)_mNR^{33}R^{34}$ (where $R^{33}$: lower alkyl; or lower alkenyl; $R^{34}$: H or lower alkyl); $(CH_2)_mN(R^{20})R^{64}$ (where: $R^{20}$: H; or lower alkyl; $R^{64}$: lower alkyl; or lower alkenyl); $(CH_2)_mCOOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^5$: lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_mOCONR^{33}R^{78}$ (where $R^{33}$: lower alkyl; or lower alkenyl; $R^{78}$: H; or lower alkyl); $(CH_2)_mNR^{20}CONR^{33}R^{78}$ (where $R^{20}$: H or lower alkyl; $R^{33}$: lower alkyl; or lower alkenyl; $R^{78}$: H; or lower alkyl); $(CH_2)_oN(R^{20})COR^{64}$ (where: $R^{20}$: H; or lower alkyl; $R^{64}$: alkyl; alkenyl; aryl; and aryl-lower alkyl; heteroaryl-lower alkyl); $(CH_2)_oCOOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^7$: lower alkyl; lower alkenyl; $(CH_2)_qOR^{55}$ (where $R^{55}$: lower alkyl; or lower alkenyl); $(CH_2)_qSR^{56}$ (where $R^{56}$: H or lower alkyl; or lower alkenyl); $(CH_2)_qNR^{33}R^{34}$ (where $R^{33}$: lower alkyl; or lower alkenyl; $R^{34}$: H; or lower alkyl); $(CH_2)_qN(R^{20})COR^{64}$ (where: $R^{20}$: H; or lower alkyl; $R^{64}$: lower alkyl; or lower alkenyl); $(CH_2)_rCOOR^{57}$ (where $R^{57}$: lower alkyl; or lower alkenyl); $(CH_2)_qCONR^{58}R^{59}$ (where $R^{58}$: lower alkyl; or lower alkenyl; and $R^{59}$: H; or lower alkyl); $(CH_2)_rPO(OR^{60})_2$ (where $R^{60}$: lower alkyl; or lower alkenyl); $(CH_2)_rSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H or lower alkyl); $(CH_2)_oOCONR^{33}R^{78}$ (where $R^{33}$: lower alkyl; or lower alkenyl; $R^{78}$: H; or lower alkyl); $(CH_2)_oNR^{20}CONR^{33}R^{78}$ (where $R^{20}$: H or lower alkyl; $R^{33}$: lower alkyl; or lower alkenyl; $R^{78}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o$COOR$^{57}$ (where $R^{57}$: lower alkyl; or lower alkenyl); $(CH^2)_o$CONR$^{58}$R$^{59}$ (where $R^{58}$: lower alkyl; or lower alkenyl; and $R^{59}$: H; or lower alkyl); $(CH_2)_o$PO(OR$^{60}$)$_2$ (where $R^{60}$: lower alkyl; or lower alkenyl); $(CH_2)_o$SO$_2$R$^{62}$ (where $R^{62}$: lower alkyl; or lower alkenyl); or $(CH^2)_q$C$_6$H$_4$R$^8$ (where $R^8$: H; F; Cl; CF$_3$; lower alkyl; lower alkenyl; or lower alkoxy).

$R^9$: lower alkyl; lower alkenyl; $(CH_2)_o$OR$^{55}$ (where $R^{55}$: lower alkyl; or lower alkenyl); $(CH_2)_o$SR$^{56}$ (where $R^{56}$: H; or lower alkyl; or lower alkenyl); $(CH_2)_o$NR$^{33}$R$^{34}$ (where $R^{33}$: lower alkyl; or lower alkenyl; $R^{34}$: H; or lower alkyl); $(CH_2)_o$N(R$^{20}$)COR$^{64}$ (where: $R^{20}$: H; or lower alkyl; $R^{64}$: lower alkyl; or lower alkenyl); $(CH_2)_o$COOR$^{57}$ (where $R^{57}$: lower alkyl; or lower alkenyl); $(CH^2)_o$CONR$^{58}$R$^{59}$ (where $R^{58}$: lower alkyl; or lower alkenyl; and $R^{59}$: H; or lower alkyl); $(CH_2)_o$PO(OR$^{60}$)$_2$ (where $R^{60}$: lower alkyl; or lower alkenyl); $(CH_2)_o$SO$_2$R$^{62}$ (where $R^{62}$: lower alkyl; or lower alkenyl); or $(CH^2)_q$C$_6$H$_4$R$^8$ (where $R^8$: H; F; Cl; CF$_3$; lower alkyl; lower alkenyl; or lower alkoxy).

$R^{10}$: lower alkyl; lower alkenyl; $(CH_2)_o$OR$^{55}$ (where $R^{55}$: lower alkyl; or lower alkenyl); $(CH_2)_o$SR$^{56}$ (where $R^{56}$: H; or lower alkyl; or lower alkenyl); $(CH_2)_o$NR$^{33}$R$^{34}$ (where $R^{33}$: lower alkyl; or lower alkenyl; $R^{34}$: lower alkenyl); $(CH_2)_o$COOR$^{57}$ (where $R^{57}$: lower alkyl; or lower alkenyl); $(CH_2)_o$CONR$^{58}$R$^{59}$ (where $R^{58}$: lower alkyl; or lower alkenyl; and $R^{59}$: H; lower alkyl); $(CH_2)_o$PO(OR$^{60}$)$_2$ (where $R^{60}$: lower alkyl; or lower alkenyl); $(CH^2)_o$SO$_2$R$^{62}$ (where $R^{62}$: lower alkyl; or lower alkenyl); or $(CH_2)_q$C$_6$H$_4$R$^8$ (where $R^8$: H; F; Cl; CF$_3$; lower alkyl; lower alkenyl; or lower alkoxy).

$R^{11}$: H; lower alkyl; lower alkenyl; $(CH_2)_m$OR$^{55}$ (where $R^{55}$: lower alkyl; or lower alkenyl); $(CH_2)_m$SR$^{56}$ (where $R^{56}$: H; or lower alkyl; or lower alkenyl); $(CH_2)_m$NR$^{33}$R$^{34}$ (where $R^{33}$: lower alkyl; or lower alkenyl; $R^{34}$: H; or lower alkyl); $(CH_2)_m$OCONR$^{33}$R$^{78}$ (where $R^{33}$: lower alkyl; or lower alkenyl; $R^{78}$: H; or lower alkyl); $(CH^2)_m$NR$^{20}$CONR$^{33}$R$^{78}$ (where $R^{20}$: H; or lower alkyl; $R^{33}$: lower alkyl; or lower alkenyl; $R^{78}$: H; or lower alkyl); $(CH_2)_m$NR$^{20}$COR$^{64}$ (where: $R^{20}$: H; or lower alkyl; $R^{64}$: lower alkyl; or lower alkenyl); $(CH_2)_o$COOR$^{57}$ (where $R^{57}$: lower alkyl; or lower alkenyl); $(CH^2)_o$CONR$^{58}$R$^{59}$ (where $R^{58}$: lower alkyl; or lower alkenyl; and $R^{59}$: H; lower alkyl); $(CH_2)_o$PO(OR$^{60}$)$_2$ (where $R^{60}$: lower alkyl; or lower alkenyl); $(CH_2)_o$SO$_2$R$^{62}$ (where $R^{62}$: lower alkyl; or lower alkenyl); or $(CH^2)_q$C$_6$H$_4$R$^8$ (where $R^8$: H; F; Cl; CF$_3$; lower alkyl; lower alkenyl; or lower alkoxy).

$R^{12}$: H; lower alkyl; lower alkenyl; $(CH_2)_m$OR$^{55}$ (where $R^{55}$: lower alkyl; or lower alkenyl); $(CH_2)_m$SR$^{56}$ (where $R^{56}$: H; or lower alkyl; or lower alkenyl); $(CH_2)_m$NR$^{33}$R$^{34}$ (where $R^{33}$: lower alkyl; or lower alkenyl; $R^{34}$: H; or lower alkyl); $(CH_2)_m$N(R$^{20}$)COR$^{64}$ (where: $R^{20}$: H; or lower alkyl; $R^{64}$: lower alkyl; or lower alkenyl); $(CH^2)_r$COOR$^{57}$ (where $R^{57}$: lower alkyl; or lower alkenyl); $(CH_2)_r$CONR$^{58}$R$^{59}$ (where $R^{58}$: lower alkyl; or lower alkenyl; and $R^{59}$: H; or lower alkyl); $(CH_2)_r$PO(OR$^{60}$)$_2$ (where $R^{60}$: lower alkyl; or lower alkenyl); $(CH^2)_r$SO$_2$R$^{62}$ (where $R^{62}$: lower alkyl; or lower alkenyl); or $(CH_2)_q$C$_6$H$_4$R$^8$ (where $R^8$: H; F; Cl; CF$_3$; lower alkyl; lower alkenyl; or lower alkoxy).

$R^{13}$: lower alkyl; lower alkenyl; $(CH_2)_q$OR$^{55}$ (where $R^{55}$: lower alkyl; or lower alkenyl); $(CH_2)_q$SR$^{56}$ (where $R^{56}$: H; or lower alkyl; or lower alkenyl); $(CH_2)_q$NR$^{33}$R$^{34}$ (where $R^{33}$: lower alkyl; or lower alkenyl; $R^{34}$: H; or lower alkyl); $(CH_2)_q$N(R$^{20}$)COR$^{64}$ (where: $R^{20}$: H; or lower alkyl; $R^{64}$: lower alkyl; or lower alkenyl); $(CH_2)_r$COO$^{57}$ (where $R^{57}$: lower alkyl; or lower alkenyl); $(CH_2)_q$CONR$^{58}$R$^{59}$ (where $R^{58}$: lower alkyl; or lower alkenyl; and $R^{59}$: H; or lower alkyl); $(CH_2)_r$PO(OR$^{60}$)$_2$ (where $R^{60}$: lower alkyl; or lower alkenyl); $(CH_2)_r$SO$_2$R$^{62}$ (where $R^{62}$: lower alkyl; or lower alkenyl); or $(CH_2)_q$ C$_6$H$_4$R$^8$ (where $R^8$H; F; Cl; CF$_3$; lower alkyl; lower alkenyl; or lower alkoxy).

$R^{14}$: H; lower alkyl; lower alkenyl; $(CH_2)_m$OR$^{55}$ (where $R^{55}$: lower alkyl; or lower alkenyl); $(CH_2)_m$SR$^{56}$ (where $R^{56}$: H; or lower alkyl; or lower alkenyl); $(CH_2)_m$NR$^{33}$R$^{34}$ (where $R^{33}$: lower alkyl; or lower alkenyl; $R^{34}$: H; or lower alkyl); $(CH_2)_m$N(R$^{20}$)COR$^{64}$ (where: $R^{20}$: H; lower alkyl; $R^{64}$: lower alkyl; or lower alkenyl); $(CH^2)_o$COOR$^{57}$ (where $R^{57}$: lower alkyl; or lower alkenyl); $(CH_2)_o$CONR$^{58}$R$^{59}$ (where $R^{58}$: lower alkyl; or lower alkenyl; and $R^{59}$: H; or lower alkyl); $(CH_2)_o$PO(OR$^{60}$)$_2$ (where $R^{60}$: lower alkyl; or lower alkenyl); $(CH^2)_o$SO$_2$R$^{62}$ (where $R^{62}$: lower alkyl; or lower alkenyl); $(CH_2)_q$C$_6$H$_4$R$^8$ (where $R^8$: H; F; Cl; CF$_3$; lower alkyl; lower alkenyl; or lower alkoxy).

$R^{15}$: lower alkyl; lower alkenyl; $(CH_2)_o$OR$^{55}$ (where $R^{55}$: lower alkyl; or lower alkenyl); $(CH_2)_o$SR$^{56}$ (where $R^{56}$: H; or lower alkyl; or lower alkenyl); $(CH_2)_o$NR$^{33}$R$^{34}$ (where $R^{33}$: lower alkyl; or lower alkenyl; $R^{34}$: H; or lower alkyl); $(CH_2)_o$N(R$^{20}$)COR$^{64}$ (where: $R^{20}$: H; or lower alkyl; $R^{64}$: lower alkyl; or lower alkenyl); particularly favoured are NR$^{20}$CO lower alkyl (R$^{20}$=H; or lower alkyl); $(CH_2)_o$COOR$^{57}$ (where $R^{57}$: lower alkyl; or lower alkenyl); $(CH_2)_o$CONR$^{58}$R$^{59}$ (where $R^{58}$: lower alkyl, or lower alkenyl; and $R^{59}$: H; lower alkyl); $(CH_2)_o$PO(OR$^{60}$)$_2$ (where $R^{60}$: lower alkyl; or lower alkenyl); $(CH_2)_o$SO$_2$R$^{62}$ (where $R^{62}$: lower alkyl; or lower alkenyl); or $(CH_2)_q$C$_6$H$_4$R$^8$ (where $R^8$: H; F; Cl; CF$_3$; lower alkyl; lower alkenyl; or lower alkoxy).

$R^{16}$: lower alkyl; lower alkenyl; $(CH_2)_o$OR$^{55}$ (where $R^{55}$: lower alkyl; or lower alkenyl); $(CH_2)_o$SR$^{56}$ (where $R^{56}$: H; or lower alkyl; or lower alkenyl); $(CH_2)_o$NR$^{33}$R$^{34}$ (where $R^{33}$: lower alkyl; or lower alkenyl; $R^{34}$: H; or lower alkyl); $(CH_2)_o$N(R$^{20}$)COR$^{64}$ (where: $R^{20}$: H; or lower alkyl; $R^{64}$: lower alkyl; or lower alkenyl); $(CH_2)_o$COOR$^{57}$ (where $R^{57}$: lower alkyl; or lower alkenyl); $(CH^2)_o$CONR$^{58}$R$^{59}$ (where $R^{58}$: lower alkyl; or lower alkenyl; and $R^{59}$: H; or lower alkyl); $(CH_2)_o$PO(OR$^{60}$)$_2$ (where $R^{60}$: lower alkyl; or lower alkenyl); $(CH_2)_o$SO$_2$R$^{62}$ (where $R^{62}$: lower alkyl; or lower alkenyl); or $(CH^2)_q$C$_6$H$_4$R$^8$ (where $R^8$: H; F; Cl; CF$_3$; lower alkyl; lower alkenyl; or lower alkoxy).

$R^{17}$: lower alkyl; lower alkenyl; $(CH_2)_q$OR$^{55}$ (where $R^{55}$: lower alkyl; or lower alkenyl); $(CH_2)_q$SR$^{56}$ (where $R^{56}$: H; or lower alkyl; or lower alkenyl); $(CH_2)_q$NR$^{33}$R$^{34}$ (where $R^{33}$: lower alkyl; or lower alkenyl; $R^{34}$: H; or lower alkyl); $(CH_2)_q$N(R$^{20}$)COR$^{64}$ (where: $R^{20}$: H; or lower alkyl; $R^{64}$: lower alkyl; or lower alkenyl); $(CH_2)_r$COOR$^{57}$ (where $R^{57}$: lower alkyl; or lower alkenyl); $(CH^2)_q$CONR$^{58}$R$^{59}$ (where $R^{58}$: lower alkyl; or lower alkenyl; and $R^{59}$: H; or lower alkyl); $(CH_2)_r$PO(OR$^{60}$)$_2$ (where $R^{60}$: lower alkyl; or lower alkenyl); $(CH_2)_r$SO$_2$R$^{62}$ (where $R^{62}$: lower alkyl; or lower alkenyl); or $(CH^2)_q$C$_6$H$_4$R$^8$ (where $R^8$: H; F; Cl; CF$_3$; lower alkyl; lower alkenyl; or lower alkoxy).

Among the building blocks A1 to A69 the following are preferred: A5 with $R^2$ being H, A8, A22, A25, A38 with $R^2$ being H, A42, A47, and A50. Most preferred are building blocks of type A8' and A8":

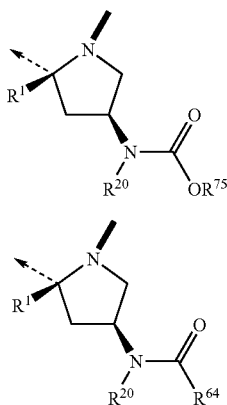

wherein $R^{20}$ is H or lower alkyl; and $R^{64}$ is alkyl; alkenyl; aryl; aryl-lower alkyl; or heteroaryl-lower alkyl; and $R^{75}$ is lower alkyl; lower alkenyl; or aryl-lower alkyl; especially those wherein $R^{75}$ is allyl (A8'-1) and $R^{64}$ is n-hexyl (A8"-1).

Building block A70 belongs to the class of open-chained α-substituted α-amino acids, building blocks A71 and A72 to the corresponding β-amino acid analogues and building blocks A73—A104 to the cyclic analogues of A70. Such amino acid derivatives have been shown to constrain small peptides in well defined reverse turn or U-shaped conformations (C. M. Venkatachalam, *Biopolymers*, 1968, 6, 1425-1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks —A70—CO— to A104CO— in combination with a building block -B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) can also consist of —A70—CO— to A104—CO— where building block A70 to A104 is of either (D)- or (L)-configuration, in combination with a building block -B—CO— of (L)-configuration.

Preferred values for $R^{20}$ in A70 to A104 are H or lower alkyl with methyl being most preferred. Preferred values for $R^{18}$, $R^{19}$ and $R^{21}$-$R^{29}$ in building blocks A70 to A104 are the following:

$R^{18}$: lower alkyl $R^{19}$: lower alkyl; lower alkenyl; $(CH_2)_pOR^{55}$ (where $R^{55}$: lower alkyl; or lower alkenyl); $(C_2)_pSR^{56}$ (where $R^{56}$: H; or lower alkyl; or lower alkenyl); $(CH_2)_pNR^{33}R^{34}$ (where $R^{33}$: lower alkyl; or lower alkenyl; $R^{34}$: H; or lower alkyl); $(CH_2)_pN(R^2COR^{64}$ (where: $R^{20}$: H; or lower alkyl; $R^{64}$: lower alkyl; or lower alkenyl); $(CH_2)_p COOR^{57}$ (where $R^{57}$: lower alkyl; or lower alkenyl); $(CH^2)CONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_p SO^2R^{62}$ (where $R^{62}$: lower alkyl; or lower alkenyl); or $(CH^2)_oC_6H_4R^8$ (where $R^8$: H; F; Cl; $CF_3$; lower alkyl; lower alkenyl; or lower alkoxy).

$R^{21}$: H; lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)NR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o SO^2R^{62}$ (where $R^{62}$: lower alkyl; or lower alkenyl); or $(CH^2)_qC_6H_4R^8$ (where $R^8$: H; F; Cl; $CF_3$; lower alkyl; lower alkenyl; or lower alkoxy).

$R^{22}$: lower alkyl; lower alkenyl; $(CH_2)_oR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o SO^2R^{62}$ (where $R^{62}$: lower alkyl; or lower alkenyl); or $(CH^2)_qC_6H_4R^8$ (where $R^8$: H; F; Cl; CF; lower alkyl; lower alkenyl; or lower alkoxy).

$R^{23}$: H; lower alkyl; lower alkenyl; $(CH_2)_oR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); $(CH_2)_oCOOR^{57}$ (where $R^{57}$: lower alkyl; or lower alkenyl); $(CH_2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{24}$: lower alkyl; lower alkenyl; $(CH_2)_oR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); $(CH_2)_oCOOR^{57}$ (where $R^{57}$: lower alkyl; or lower alkenyl); $(CH_2)_oCONR^{58}R^{59}$ (where $R^{58}$:

lower alkyl, or lower alkenyl; and $R_{59}$: H; lower alkyl); $(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{25}$: H; lower alkyl; lower alkenyl; $(CH_2)_mOR^{55}$ (where $R^{55}$: lower alkyl; or lower alkenyl); $(CH_2)NR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl; or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH^2)_qC_6H_4R^8$ (where $R^8$: H; F; Cl; $CF_3$; lower alkyl; lower alkenyl; or lower alkoxy).

$R^{26}$: H; lower alkyl; lower alkenyl; $(CH_2)_mOR^{55}$ (where $R^{55}$: lower alkyl; or lower alkenyl); $(CH_2)_mNR^{33}R^{34}$ (where $R^{33}$: lower alkyl; or lower alkenyl; $R^{34}$: H; or lower alkyl); $(CH_2)_mN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH^2)_qC_6H_4R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{34}(CH_2)_2$—;

$R^{27}$: H; lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)NR^{33}R^{34}$ (where $R^{33}$: lower alkyl; or lower alkenyl; $R^{34}$: H; or lower alkyl); $(CH_2)_oN^2(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH^2)_qC_6H_4R^8$ (where $R^8$: H; F; Cl; $CF_3$; lower alkyl; lower alkenyl; or lower alkoxy).

$R^{29}$: lower alkyl; lower alkenyl; $(CH_2)_oOR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H; or lower alkyl); $(CH_2)_oN(R^{20})COR^{64}$ (where: $R^{20}$: H; or lower alkyl; $R^{64}$: lower alkyl; or lower alkenyl); particularly favoured are $NR^{20}CO$lower-alkyl ($R^{20}$=H; or lower alkyl); $(CH_2)_oCOOR^{57}$ (where $R^{57}$: lower alkyl; or lower alkenyl); $(CH_2)_oCONR^{58}R^{59}$ (where $R^{58}$: lower alkyl, or lower alkenyl; and $R^{59}$: H; lower alkyl); $(CH_2)_oPO(OR^{60})$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

For templates (b) to (p), such as (b1) and (c1), the preferred values for the various symbols are the following:

$R^8$: H; F; Cl; $CF_3$; lower alkyl; lower alkenyl; $(CH_2)_oR^{55}$ (where $R^{55}$: lower alkyl; or lower alkenyl); $(CH_2)_oSR^{56}$ (where $R^{56}$: H; or lower alkyl; or lower alkenyl); $(CH_2)_oNR^{33}R^{34}$ (where $R^{33}$: lower alkyl; or lower alkenyl; $R^{34}$: H or lower alkyl); $(CH_2)_oN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; or lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{20}$: H; or lower alkyl $R^{30}$: H, methyl $R^{31}$: H; lower alkyl; lower alkenyl; $(CH_2)_pOR^{55}$ (where $R^{55}$: lower alkyl; or lower alkenyl); $(CH_2)_pNR^{33}R^{34}$ (where $R^{33}$: lower alkyl; or lower alkenyl; $R^{34}$: H; or lower alkyl); $(CH_2)_pN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o SO_2R^{62}$ (where $R^{62}$: lower alkyl; or lower alkenyl); or $(CH^2)_rC_6H_4R^8$ (where $R^8$: H; F; Cl; $CF_3$; lower alkyl; lower alkenyl; or lower alkoxy); most preferred are $CH^2CONR^{58}R^{59}$ ($R^{58}$: H; or lower alkyl; $R^{59}$: lower alkyl; or lower alkenyl).

$R^{32}$: H, methyl $R^{33}$: lower alkyl; lower alkenyl; $(CH_2)_mOR^{55}$ (where $R^{55}$: lower alkyl; or lower alkenyl); $(CH_2)_mSR^{56}$ (where $R^{56}$: H; or lower alkyl; or lower alkenyl); $(CH_2)_mNR^{33}R^{34}$ (where $R^{33}$: lower alkyl; or lower alkenyl; $R^{34}$: H; or lower alkyl); $(CH_2)_mOCONR^{33}R^{78}$ (where $R^{33}$: lower alkyl; or lower alkenyl; $R^{78}$: H; or lower alkyl); $(CH_2)_mNR^{20}CONR^{33}R^{78}$ (where $R^{20}$: H or lower alkyl; $R^{33}$: lower alkyl; or lower alkenyl; $R^{78}$: H; or lower alkyl); $(CH^2)_oN(R^{20})COR^{64}$ (where: $R^{20}$: H; or lower alkyl; $R^{64}$: lower alkyl; or lower alkenyl); $(CH_2)_oCOOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; lower alkyl).

$R^{34}$: H; or lower alkyl.

$R^{35}$: H; lower alkyl; lower alkenyl; $(CH_2)_mOR^{55}$ (where $R^{55}$: lower alkyl; or lower alkenyl); $(CH^2)_mN(R^{20})COR^{64}$ (where: $R^{20}$: H; or lower alkyl; $R^{64}$: lower alkyl; or lower alkenyl); $(CH_2)_oCOOR^{57}$ (where $R^{57}$: lower alkyl; or lower alkenyl); $(CH_2)_oCONR^{58}R^{59}$ (where $R^{58}$: lower alkyl; or lower alkenyl; and $R^{59}$: H; lower alkyl).

$R^{36}$: lower alkyl; lower alkenyl; or aryl-lower alkyl.

$R^{37}$: H; lower alkyl; lower alkenyl; $(CH_2)_pOR^{55}$ (where $R^{55}$: lower alkyl; or lower alkenyl); $(CH_2)_pNR^{33}R^{34}$ (where $R^{33}$: lower alkyl; or lower alkenyl; $R^{34}$: H; or lower alkyl); $(CH_2)_pN(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH^2)_oCONR^{58}R^{59}$ (where $R^{58}$: lower alkyl, or lower alkenyl; and $R^{59}$: H; lower alkyl); $(CH_2)_oPO(OR^{60})_2$ (where $R^{60}$: lower alkyl; or lower alkenyl); $(CH_2)_o$ $SO_2R^{62}$ (where $R^{62}$: lower alkyl; or lower alkenyl); or $(CH_2)_q C_6H_4R^8$ (where $R^8$: H; F; Cl; $CF_3$; lower alkyl; lower alkenyl; or lower alkoxy).

$R^{38}$: H; lower alkyl; lower alkenyl; $(CH_2)_p OR^{55}$ (where $R^{55}$: lower alkyl; or lower alkenyl); $(CH_2)_p NR^{33}R^{34}$ (where $R^{33}$: lower alkyl; or lower alkenyl; $R^{34}$: H; or lower alkyl); $(CH_2)_p N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl, or lower alkenyl; and $R^{59}$: H; lower alkyl); $(CH_2)_o PO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_q C_6H_4R^8$ (where $R^8$: H; F; Cl; $CF_3$; lower alkyl; lower alkenyl; or lower alkoxy).

$R^{39}$: H; lower alkyl; lower alkenyl; $(CH_2)_m OR^{55}$ (where $R^{55}$: lower alkyl; or lower alkenyl); $(CH_2)_m N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl; or lower alkenyl; and $R^{59}$: H; lower alkyl).

$R^{40}$: lower alkyl; lower alkenyl; or aryl-lower alkyl.

$R^{41}$: H; lower alkyl; lower alkenyl; $(CH_2)_p OR^{55}$ (where $R^{55}$: lower alkyl; or lower alkenyl; $(CH_2)_p NR^{33}R^{34}$ (where $R^{33}$: lower alkyl; or lower alkenyl; $R^{34}$: H; or lower alkyl); $(CH_2)_p N(R^{20})COR^{64}$ (where: $R^{20}$: H; or lower alkyl; Re: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl, or lower alkenyl; and $R^{59}$: H; lower alkyl); $(CH_2)_o PO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_q C_6H_4R^8$ (where $R^8$: H; F; Cl; $CF_3$; lower alkyl; lower alkenyl; or lower alkoxy).

$R^{42}$: H; lower alkyl; lower alkenyl; $(CH_2)_p OR^{55}$ (where $R^{55}$: lower alkyl; or lower alkenyl); $(CH_2)_p NR^{33}R^{34}$ (where $R^{33}$: lower alkyl; or lower alkenyl; $R^{34}$: H; or lower alkyl); $(CH_2)_p N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl, or lower alkenyl; and $R^{59}$: H; lower allyl); $(CH_2)_o PO(OR^{60})$ (where $R^{60}$: lower alkyl; or lower alkenyl); $(CH_2)_o SO_2R^{62}$ (where $R^{62}$: lower alkyl; or lower alkenyl); or $(CH_2)_q C_6H_4R^8$ (where $R^8$: H; F; Cl; $CF_3$; lower alkyl; lower alkenyl; or lower alkoxy).

$R_{43}$: H; lower alkyl; lower alkenyl; $(CH_2)_m OR^{55}$ (where $R^{55}$: lower alkyl; or lower alkenyl); $(CH_2)_m SR^{56}$ (where $R^{56}$: lower alkyl; or lower alkenyl); $(CH_2)_m NR^{33}R^{34}$ (where $R^{33}$: lower alkyl; or lower alkenyl; $R^{34}$: H; or lower alkyl); $(CH_2)_m N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl; or lower alkenyl; and $R^{59}$: H; lower alkyl); $(CH_2)_o PO(OR^{60})_2$ (where $R^{60}$: lower alkyl; or lower alkenyl); $(CH_2)_o SO_2R^{62}$ (where $R^{62}$: lower alkyl; or lower alkenyl); or $(CH_2)_q C_6H_4R^8$ (where $R^8$: H; F; Cl; $CF_3$; lower alkyl; lower alkenyl; or lower alkoxy).

$R^{44}$: lower alkyl; lower alkenyl; $(CH_2)_p OR^{55}$ (where $R^{55}$: lower alkyl; or lower alkenyl); $(CH_2)_p SR^{56}$ (where $R^{56}$: H; or lower alkyl; or lower alkenyl); $(CH_2)_p NR^{33}R^{34}$ (where $R^{33}$: lower alkyl; or lower alkenyl; $R^{34}$: H; or lower alkyl); $(CH_2)_p N(R^{20})COR^{64}$ (where: $R^{20}$: H; or lower alkyl; $R^{64}$: lower alkyl; or lower alkenyl); $(CH_2)_p COOR^{57}$ (where $R^{57}$: lower alkyl; or lower alkenyl); $(CH_2)_p CONR^{58}R^{59}$ (where $R^{58}$: lower alkyl; or lower alkenyl; and $R^{59}$: H; lower alkyl); or $(CH_2)_o C_6H_4R^8$ (where $R^8$: H; F; Cl; $CF_3$; lower alkyl; lower alkenyl; or lower alkoxy).

$R^{45}$: H; lower alkyl; lower alkenyl; $(CH_2)_s OR^{55}$ (where $R^{55}$: lower alkyl; or lower alkenyl); $(CH_2)_s SR^{56}$ (where $R^{56}$: H; or lower alkyl; or lower alkenyl); $(CH_2)_s N^{33}R^{34}$ (where $R^{33}$: lower alkyl; or lower alkenyl; $R^{34}$: H; or lower alkyl); $(CH_2)_o N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl; or lower alkenyl; and $R^{59}$: H; lower alkyl); or $(CH_2)_s C_6H_4R^3$ (where $R^8$: H; F; Cl; $CF_3$; lower alkyl; lower alkenyl; or lower alkoxy).

$R^{46}$: H; lower alkyl; lower alkenyl; $(CH_2)_s OR^{55}$ (where $R^{55}$: lower alkyl; or lower alkenyl); $(CH_2)_s SR^{56}$ (where $R^{56}$: H; or lower alkyl; or lower alkenyl); $(CH_2)NR^{33}R^{34}$ (where $R^{33}$: lower alkyl; or lower alkenyl; $R^{34}$: H; or lower alkyl); $(CH_2)_o N(R^{20})COR^{64}$ (where: $R^{20}$: H; or lower alkyl; $R^{64}$: lower alkyl; or lower alkenyl); $(CH_2)_o COOR^{57}$ (where $R^{57}$: lower alkyl; or lower alkenyl); $(CH_2)_o CONR^{58}R^{59}$ (where $R^{58}$: lower alkyl; or lower alkenyl; and $R^{59}$: H; lower alkyl); or $(CH_2)_s C_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; $(CH_2)_o COOR^{57}$ (where $R^{57}$: lower alkyl; or lower alkenyl); $(CH_2)_o CONR^{58}R^{59}$ (where $R^{58}$: lower alkyl; or lower alkenyl; and $R^{59}$: H; lower alkyl); or $(CH_2)_s C_6H_4R^8$ (where $R^8$: H; F; Cl; $CF_3$; lower allyl; lower alkenyl; or lower alkoxy).

$R^{50}$: H; methyl $R^{51}$: H; lower alkyl; lower alkenyl; $(CH_2)_m OR^{55}$ (where $R^{55}$: lower alkyl; or lower alkenyl); $(CH_2)_m NR^{33}R^{34}$ (where $R^{33}$: lower alkyl; or lower alkenyl; $R^{34}$: H; or lower alkyl); $(CH_2)_m N(R^{20})COR^{64}$ (where: $R^{20}$: H; or lower alkyl; $R^{64}$: lower alkyl; or lower alkenyl); $(CH_2)_p COOR^{57}$ (where $R^{57}$: lower alkyl; or lower alkenyl); $(CH_2)_p CONR^{58}R^{59}$ (where $R^{58}$: lower alkyl; or lower alkenyl; and $R^{59}$: H; lower alkyl); or $(CH_2)_r C_6H_4R^8$ (where $R^8$: H; F; Cl; $CF_3$; lower alkyl; lower alkenyl; or lower alkoxy).

$R^{52}$: H; lower alkyl; lower alkenyl; $(CH_2)_m OR^{55}$ (where $R^{55}$: lower alkyl; or lower alkenyl); $(CH_2)_m NR^{33}R^{34}$ (where $R^{33}$: lower alkyl; or lower alkenyl; $R^{34}$: H; or lower alkyl); $(CH_2)_m N(R^{20})COR^{64}$ (where: $R^{20}$: H; or lower alkyl; $R^{64}$: lower alkyl; or lower alkenyl); $(CH_2)_p COOR^{57}$ (where $R^{57}$: lower alkyl; or lower alkenyl); $(CH_2)_p CONR^{58}R^{59}$ (where $R^{58}$: lower alkyl; or lower alkenyl; and $R^{59}$: H; lower alkyl), or $(CH_2)_r C_6H_4R^8$ (where $R^8$: H; F; Cl; $CF_3$; lower alkyl; lower alkenyl; or lower alkoxy).

$R^{53}$: H; lower alkyl; lower alkenyl; $(CH_2)_m OR^{55}$ (where $R^{55}$: lower alkyl; or lower alkenyl); $(CH_2)_m R^{33}R^{34}$ (where $R^{33}$: lower alkyl; or lower alkenyl; $R^{34}$: H; or lower alkyl); $(CH_2)_m N(R^{20})COR^{64}$ (where: $R^{20}$: H; or lower alkyl; $R^{64}$: lower alkyl; or lower alkenyl); $(CH_2)_p COOR^{57}$ (where $R^{57}$: lower alkyl; or lower alkenyl); $(CH_2)_p CONR^{58}R^{59}$ (where $R^{58}$: lower alkyl; or lower alkenyl; and $R^{59}$: H; lower alkyl); or $(CH_2)_r C_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block -B—CO— within template (a1) and (a2) designates an L-amino acid residue. Preferred values for B are: —$NR^{20}CH(R^{71})$— and enantiomers of groups A5 with $R^2$ being H, A8, A22, A25, A38 with $R^2$ being H, A42, A47, and A50. Most preferred are Ala L-Alanine
Arg L-Arginine
Asn L-Asparagine
Cys L-Cysteine
Gln L-Glutamine
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert.-Butylglycine
4AmPhe L-para-Aminophenylalanine
3AmPhe L-meta-Aminophenylalanine
2AmPhe L-ortho-Aminophenylalanine
Phe(mC($NH_2$)=NH) L-meta-Amidinophenylalanine
Phe(pC($NH_2$)=NH) L-para-Amidinophenylalanine
Phe(mNHC($NH_2$)=NH) L-meta-Guanidinophenylalanine
Phe(pNHC($NH_2$)=NH) L-para-Guanidinophenylalanine
Phg L-Phenylglycine
Cha L-Cyclohexylalanine
$C_4$al L-3-Cyclobutylalanine
$C_5$al L 3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2Chlorophenylalanine
3,4$Cl_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine
Dpr L-2,3-Diaminopropionic acid
$A_2$Bu L-2,4-Diaminobutyric acid
Dbu (S)-2,3-Diaminobutyric acid
Abu γ—Aminobutyric acid (GABA)
Aha ε—Aminohexanoic acid
Aib α—Aminoisobutyric acid
Y(Bzl) L-O-Benzyltyrosine
Bip L-Biphenylalanine
S(Bzl) L-O-Benzylserine
T(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L Benzoylphenylalanine
Pip L-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methvaline
MeLeu L-N-Methylleucine In addition, the most preferred values for B also include groups of type A8''' of (L)-configuration:

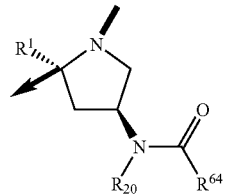

A8''' wherein $R^{20}$ is H or lower alkyl and $R^{64}$ is alkyl; alkenyl; aryl; aryl-lower alkyl; or heteroaryl-lower alkyl; especially those wherein $R^{64}$ is n-hexyl (A8'''-1).

The peptidic chains Z of the β-hairpin mimetics described herein is generally defined in terms of amino acid residues belonging to one of the following groups:

Group C —$NR^{20}CH(R^{72})CO$—; <<hydrophobic: small to medium-sized>>

Group D —$NR^{20}CH(R^{73})CO$—; <<hydrophobic: large aromatic or heteroaromatic>>

Group E —$NR^{20}CH(R^{74})CO$—; "polar-cationic" and "urea-derived"

Group F —$NR^{20}CH(R^{84})CO$—; "polar-non-charged" and "anionic"

Group H —$NR^{20}$—CH(CO—)—$(CH_2)_{4-7}$—CH(CO—)—$NR^{20}$—; —$NR^{20}$—CH(CO—)—$(CH_2)_p$SS$(CH_2)_p$—CH(CO—)—$NR^{20}$—; —$NR^{20}$—CH(CO—)—(—$(CH_2)_p$CO$(CH_2)_p$—CH(CO—)—$NR^{20}$—; and —$NR^{20}$—CH(CO—)—(—$(CH_2)_p$NR^{20}$CONR^{20}(CH_2)_p$—CH(CO—)—$NR^{20}$—, "inter-strand linkage"

Furthermore, the amino acid residues in chain Z can also be of formula —A—CO— wherein A is as defined above.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates -and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates -and phosphates or tertiary amines. Genetically encoded heteroaromatic amino acids include tryptophan and histidine.

Group E comprises amino acids containing side chains with polar-cationic and urea-derived residues according to the general definition for substituen $R^{74}$. Polar-cationic refers to a basic side chain which is protonated at physiological pH. Genetically encoded polar-cationic amino acids include arginine, lysine and histidine. Citrulline is an example for an amino acid containing a urea-derived residue.

Group F comprises amino acids containing side chains with polar-non-charged or anionic residues according to the general definition for substituent $R^{84}$. A polar-non-charged or anionic residue refers to a hydrophilic side chain that is uncharged and, respectively, anionic at physiological pH (carboxylic acids are included), but that is not repelled by aqueous solutions. Such side chains typically contain hydrogen bond donor groups such as (but not limited to) primary and secondary amides, carboxylic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates -and phosphates or tertiary amines. Genetically encoded polar-non-charged and anionic amino acids include asparagine, cysteine, glutamine, serine and threonine but also aspartic acid and glutamic acid.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, Ill., 1984; Ahmed et al. J. Biol. Chem. 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared as described hereinafter in the pertinent Examples (procedure 3), using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, positions for interstrand linkages are the following:

if n=11: Positions P2 and P10 taken together.

Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviation corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^{D}$Pro | D-Proline | $^{D}$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:
Cit L-Citrulline
Orn L-Ornithine
tBuA L-t-Butylalanine
Sar Sarcosine
Pen L-Penicillamine
t-BuG L-tert.-Butylglycine
4AmPhe L-para-Aminophenylalanine
3AmPhe L-meta-Aminophenylalanine
2AmPhe L-ortho-Aminophenylalanine
Phe(mC($NH_2$)=NH L-meta-Amidinophenylalanine
Phe(pC($NH_2$)=NW L-para-Amidinophenylalanine
Phe(mNHC($NH_2$)=NH) L-meta-Guanidinophenylalanine
Phe(pNHC($NH_2$)=NH) L-para-Guanidinophenylalanine
Phg L-Phenylglycine
Cha L-Cyclohexylalanine
$C_4$al L-3-Cyclobutylalanine C₅al L-3Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl₂-Phe L-3,4-Dichlorophenylalanine
4F-Phe L-4-Fluorophenylalanine
3F-Phe L-3-Fluorophenylalanine
2F-Phe L-2-Fluorophenylalanine
Tic 1,2,3,4-Tetrahydroisoquinoline-3-carboxylic acid
Thi L-β-2-Thienylalanine
Tza L-2-Thiazolylalanine
Mso L-Methionine sulfoxide
AcLys N-Acetyllysine
Dpr 2,3-Diaminopropionic acid
A₂Bu 2,4-Diaminobutyric acid
Dbu (S)-2,3-Diaminobutyric acid
Abu γ—Aminobutyric acid (GABA)
Aha ε—Aminohexanoic acid
Aib α—Aminoisobutyric acid
Y(Bzl) L-O-Benzyltyrosine
Bip L-(4-phenyl)phenylalanine
S(Bzl) L-O-Benzylserine
T(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L-4-Benzoylphenylalanine
4—AmPyrr1 (2S,4S)-4—Amino-pyrrolidine-L-carboxylic acid
4—AmPyrr2 (2S,4R)-4—Amino-pyrrolidine-L-carboxylic acid
4-PhePyrr1 (2S,5R)-4-Phenyl-pyrrolidine-L-carboxylic acid
4-PhePyrr2 (2S,5S)-4-Phenyl-pyrrolidine-L-carboxylic acid
5-PhePyrr1 (2S,5R)-5-Phenyl-pyrrolidine-carboxylic acid
5-PhePyrr2 (2S,5S)-5-Phenyl-pyrrolidine-L-carboxylic acid
Pro(4-OH)1 (4S)-L-Hydroxyproline
Pro(4-OH)2 (4R)-L-Hydroxyproline
Pip L-Pipecolic acid
ᴰPip D-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methylvaline
MeLeu L-N-Methylleucine
Particularly preferred residues for group C are:
Ala L-Alanine
Ile L-Isoleucine
Leu L-Leucine
Met L-Methionine
Val L-Valine
tBuA L-t-Butylalanine
t-BuG L-tert.-Butylglycine
Cha L-Cyclohexylalanine
C₄al L-3-C-Cyclobutylalanine
C₅al L-3-Cyclopentylalanine
Nle L-Norleucine
hCha L-Homo-cyclohexylalanine
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methylvaline
MeLeu L-N-Methylleucine
Particularly preferred residues for group D are:
His L-Histidine
Phe L-Phenylalanine
Trp L-Tryptophan
Tyr L-Tyrosine
Phg L-Phenylglycine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2Chlorophenylalanine
3,4Cl₂-Phe L-3,4-Dichlorophenylalanine
4F-Phe L-4-Fluorophenylalanine
3F-Phe L-3-Fluorophenylalanine
2F-Phe L-2-Fluorophenylalanine
Thi L-4-β-2-Thienylalanine
Tza L-2-Thiazolylalanine
Y(Bzl) L-O-Benzyltyrosine
Bip L-Biphenyalanine
S(Bzl) L-Benzylserine
T(Bzl) L-O-Benzylthreonine
hPhe L-Homo-phenylalanine
Bpa L-4-Benzoylphenylalanine
Particularly preferred residues for group E are
Arg L-Arginine
Lys L-Lysine
Orn L-Ornithine
Dpr L-2,3-Diaminopropionic acid
A₂Bu L-2,4-Diaminobutyric acid
Dbu (S)-2,3-Diaminobutyric acid
Phe(pNH₂) L-para-Aminophenylalanine
Phe(mNH₂) L-meta-Aminophenylalanine
Phe(oNH₂) L-ortho-Aminophenylalanine
hArg L-Homo-arginine
Phe(mC(NH₂)=NH) L-meta-Amidinophenylalanine
Phe(pC(NH₂)=NH) L-para-Amidinophenylalanine
Phe(mNHC(NH₂)=NH) L-meta-Guanidinophenylalanine
Phe(pNHC(NH₂)=NH) L-para-Guanidinophenylalanine
Cit L-Citrulline
Particularly preferred residues for group F are
Asp L-Aspartic acid
Asn L-Asparagine
Cys L-Cysteine
Glu L-Glutamic acid
Gln L-Glutamine
Ser L-Serine
Thr L-Threonine
Cit L-Citrulline
Pen L-Penicillamine
AcLys L-Nᶜ—Acetyllysine
hCys L-Homo-cysteine
hSer L-Homo-serine Generally, the peptidic chain Z within the β-hairpin mimetics of the invention comprises 7 or 11 amino acid residues (n=7 or 11). The positions $P^1$ to $P''$ of each amino acid residue in the chain Z are unequivocally defined as follows: $P^1$ represents the first amino acid in the chain Z that is coupled with its N-terminus to the C-terminus of the templates (b)-(p) or of group -B—CO— in template (a1), or of Group —A—CO— in template (A2) and P" represents the last amino acid in the chain Z that is coupled with its C-terminus to the N-terminus of the templates (b)-(p) or of group -A—CO— in template (a1) or of group -B—CO— in template (A2). Each of the positions $P^1$ to $P''$ will preferably contain an amino acid residue belonging to one or two or three of above types C to F, or being Pro, as follows:

if n is 7, the amino acid residues in position 1-7 are preferably:
  P1: of type C or of type F;
  P2: of type E or of type D or of type C;
  P3: of type F or of type C;
  P4: of type C or type F or of type D;
  P5: of type F, or the residue is Pro;
  P6: of type C or of type E, or the residue is Pro;
  P7: of type C or of type F;
if n is II, the amino acid residues in position 1-11 are preferably:
  P1: of type E or of type F;
  P2: of type C or of type F;
  P3: of type C;
  P4: of type E or of type D or of type C;
  P5: of type F or of type C;
  P6: of type C, or of type D;
  P7: of type F, or the residue is Pro;
  P8: of type C or of type E, or the residue is Pro;
  P9: of type C or of type F;
  P10: of type F or of type C;
  P11: of type D or of type E; or
  P2 and P10, taken together can form a group of type H;

Particularly preferred β-peptidomimetics of the invention include those described in Examples 1, 4, 7, 8 and 15.

The process of the invention can advantageously be carried out as parallel array synthesis to yield libraries of template-fixed β-hairpin peptidomimetics of the above general formula I. Such parallel synthesis allows one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J. -M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably 1-5%, divinylbenzene and functionalized by means of the 2-chlorotrityl linker.

When carried out as a parallel array synthesis the process of the invention can be advantageously carried out as described hereinbelow but it will be immediately apparent to those skilled in the art how this procedure will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH) trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)
  Cbz benzyloxycarbonyl
  Boc tert.-butyloxycarbonyl
  Fmoc 9-fluorenylmethoxycarbonyl
  Alloc allyloxycarbonyl
  Teoc trimethylsilylethoxycarbonyl
  Tcc trichloroethoxycarbonyl Nps o-nitrophenylsulfonyl;
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph phenyl
Pac Phenacyl
Allyl
Tse trimethylsilylethyl
Tce trichloroethyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl
for the hydroxy group (as is present e.g. in the sidechain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea is insoluble and, respectively, diisopropylurea is soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP) (Castro et al., *Tetrahedron Lett.* 1975, 14, 1219-1222; *Synthesis,* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 3542).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for S to 300 minutes, preferably 15 minutes, and drained by gravity followed by gas pressure applied through the manifold inlet (while closing the outlet) to expel the solvent;
2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide is prepared.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such a protecting group for amino which can be selectively removed, e.g. by means of Pd$^o$ and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 24 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Before removing the protecting groups from the fully protected cyclic peptide, it is possible, if desired, to form an interstrand linkage between side-chains of appropriate amino acid residues at opposite positions of the β-strand region. Interstrand linkages and their formation have been discussed above, in connection with the explanations made regarding groups of the type H which can, for example, be disulfide bridges formed by cysteines and homocysteines at opposite positions of the β-strand, or glutamic and aspartic acid residues linking ornithines and, respectively, lysines located at opposite β-strand positions by amide bond formation. The formation of such interstrand linkages can be effected by methods well known in the art.

Finally, the fully protected peptide derivative of type I is treated with 95% TFA, 2.5% $H_2O$, 2.5% TIS or another combination of scavengers for effecting the cleavage of the protecting groups. The cleavage reaction time is commonly 30 minutes to 12 hours, preferably about 2 hours. Thereafter most of the TFA is evaporated and the product is precipitated with ether/hexane (1:1) or other solvents which are suitable therefor. After careful removal of the solvent, the cyclic peptide derivative obtained as end-product can be isolated. Depending on ist purity, this peptide derivative can be used directly for biological assays, or it has to be further purified, for example by preparative HPLC.

As mentioned earlier, it is thereafter possible, if desired, to convert a fully deprotected product thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The starting materials used in the process of the invention, pre-starting materials therefor, and the preparation of these starting and pre-starting materials will now be discussed in detail.

Building blocks of type A can be synthesized according to the literature methods described below. The corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron (Report)* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

A1: See D. Ben-Ishai, *Tetrahedron* 1977, 33, 881-883; K. Sato, A. P. Kozikowski, *Tetrahedron Lett.* 1989, 30, 4073-4076; J. E. Baldwin, C. N. Farthing, A. T. Russell, C. J. Schofield, A. C. Spirey, *Tetrahedron Lett.* 1996, 37, 3761-3767; J. E. Baldwin, R. M. Adlington, N. G. Robinson, *J. Chem. Soc. Chem. Commun.* 1987, 153-157; P. Wipf, Y. Uto, *Tetrahedron Lett.* 1999, 40, 5165-5170; J. E. Baldwin, R. M. Adlington, A. O'Neil, A. C. Spirey, J. B. Sweeney, *J. Chem. Soc. Chem. Commun.* 1989, 1852-1854 (for $R^1$=H, $R^2$=H); T. Hiyana, *Bull. Chem. Soc. Jpn.* 1974, 47, 2909-2910; T. Wakamiya, K. Shimbo, T. Shiba, K. Nakajima, M. Neya, K. Okawa, *Bull Chem. Soc. Jpn.* 1982, 55, 3878-3881; L Shima, N. Shimazaki, K. Imai, K. Hemmi, M. Hashimoto, *Chem. Pharm. Bull.* 1990, 38, 564-566; H. Han, J. Yoon, K. D. Janda, *J. Org. Chem.* 1998, 63, 2045-2048 ($R^1$=H, $R^2$=Me); J. Legters, G. H. Willems, L. Thijs, B. Zwannenburg, *Recl. Trav. Chim. Pays-Bas* 1992, 111, 59-68 ($R^1$=H, $R^2$=hexyl); J. Legters, L. Thijs, B. Zwannenburg, *Recl. Trav. Chim. Pays-Bas* 1992, 111, 16-21; G. A. Molander, P. J. Stengel, *J. Org. Chem.* 1995, 21, 6660-6661 ($R^1$=H, $R^2$=Ph); I. Funaki, L. Thijs, B. Zwannenburg, *Tetrahedron* 1996, 52, 9909-9924 ($R^1$=H, $R^2$=Bn); A. S. Pepito, D. C. Dittmer, *J. Org. Chem.* 1997, 62, 7920-7925; ($R^1$=H, $R^2$=$CH_2OH$); M. Egli, A. S. Dreiding, *Helv. Chim. Acta* 1986, 69, 1442-1460 ($R^2$=CH(OH)$CH_2OH$); M. Carduccu, S. Fioravanti, M. A. Loreto, L.

Pellacani, P. A. Tardella, *Tetrahedron Lett.* 1996, 37, 3777-3778; F. J. Lakner, L. P. Hager, *Tetrahedron: Asymmetry* 1997, 21, 3547-3550 ($R^1$=Me, $R^2$=H, Me); G. A. Molander, P. J. Stengel, *Tetrahedron* 1997, 26, 8887-8912; M. A. Loreto, F. Pompei, P. A. Tardella, D. Tofani, *Tetrahedron* 1997, 53, 15853-15858 ($R^1$=Me, $R^2$=CH$_2$SiMe$_3$); H. Shao, J. K. Rueter, M. Goodman, *J. Org. Chem.* 1998, 63, 5240-5244 ($R^1$=Me, $R^2$=Me).

A2: See A. Rao, M. K. Gurjär, V. Vivarr, *Tetrahedron: Asymmetry* 1992, 3, 859-862; R. L. Johnson, G. Rayakumar, K. -L. Yu, R. K. Misra, *J. Med. Chem.* 1986, 29, 2104-2107 ($R^1$=H, $R^2$=H); J. E. Baldwin, R. M. Adlington, R. H. Jones, C. J. Schofield, C. Zarcostas, *J. Chem. Soc. Chem. Commun.* 1985, 194-196; J. E. Baldwin, R. M. Adlington, R. H. Jones, C. J. Schofield, C. Zarcostas, *Tetrahedron* 1986, 42, 4879-4888 ($R_1$=H, $R^2$=CH$_2$OH, CH$_2$CHO, CH$_2$CH$_2$COOH, CH$_2$CH$_2$OH); A. P. Kozikowski, W. Tueckmantel, I. J. Reynolds, J. T. Wroblewski, *J. Med. Chem.* 1990, 33, 1561-1571; A. P. Kozikowski, W. Tueckmantel, Y. Liao, H. Manev, S. Ikonomovic J. T. Wroblenski, *J. Med. Chem.* 1993, 36, 2706-2708 ($R^1$=H, $R^2$=CH$_2$OH, CHCONH$_2$, CONHCH$_2$COOH, COOtBu); D. Seebach, T. Vettiger, H. -M. Müller, D. Plattner, W. Petter, *Liebigs Ann. Chem.* 1990, 687-695 ($R^1$=ArylCH(OH), $R^2$=H); D. Seebach, E. Dziadulewicz, L. Behrendt, S. Cantoreggi, R. Fitzi, *Liebigs Ann. Chem.* 1989, 1215-1232 ($R^1$=Me, Et, $R^2$=H).

A3: See A. P. Kozikowski, Y. Liao, W. Tueckmantel, S. Wang, S. Pshsenichlin, *Bioorg. Med. Chem. Lett.* 1996, 6, 2559-2564 ($R^1$=H; $R^2$=CHCHO, CH$_2$OH, CH$_2$CH$_2$OH, CH$_2$COOH, COOH); Isono, *J. Am. Chem. Soc,* 1969, 91, 7490 ($R^1$=H; $R^2$=Et); P. J. Blythin, M. J. Green, M. J. Mary, H. Shue, *J. Org. Chem.* 1994, 59, 6098-6100; S. Hanessian, N. Bernstein, R. -Y. Yang, R. Maquire, *Bioorg. Chem. Lett.* 1994, 9, 1437-1442 ($R^1$=H; $R^2$=Ph).

A4: See G. Emmer, *Tetrahedron* 1992, 48, 7165-7172; M. P. Meyer, P. L. Feldman, H. Rapoport, *J. Org. Chem.* 1985, 50, 5223-5230 ($R^1$=H; $R^2$=H); A. J. Bose, M. S. Manhas, J. E. Vincent, I. F. Fernandez, *J. Org. Chem.* 1982, 47, 4075-4081 ($R^1$=H; $R^2$=NHCOCH$_2$OPh); D. L. Boger, J. B. Meyers, *J. Org. Chem.* 1991, 56, 5385-5390 ($R^1$=H; $R^2$=NHCOCH$_2$Ph); K. -D. Kampe, *Tetrahedron Lett.* 1969, 117-120 ($R^1$=CH$_2$OH; $R^2$=Ph); M. D. Andrews, M. G. Maloney, K. L. Owen, *J. Chem Soc. Perkin Trans.* 1, 1996, 227-228 ($R^1$=CH$_2$OH; $R^2$=H).

A5: See C. Bisang, C. Weber, J. Inglis, C. A. Schiffer, W. F. van Gunsteren, J. A. Robinson *J. Am. Chem. Soc.* 1995, 117, 7904 ($R^1$=CH$_3$; $R^2$=H); S. Takano, M. Morija, Y. Iwabuki, K. Ogasawara, *Tetrahedron Lett.* 1989, 30, 3805-3806 ($R^1$=H; $R^2$=COOH); M. D. Bachi, R. Breiman, H. Meshular, *J. Org. Chem.* 1983, 48, 1439-1444 ($R^1$=H; $R^2$=CH(Et)COOH); D. S. Kemp, T. P. Curran, *Tetrahedron Lett.* 1988, 29, 4931-4934; D. S. Kemp, T. P. Curran, W. M. Davies, *J. Org. Chem.* 1991, 56, 6672-6682 ($R^1$=H; $R^2$=CH$_2$OH); F. Manfre, J. -M. Kern, J. -F. Biellmann, *J. Org. Chem.* 1992, 57, 2060-2065 ($R^1$=H; $R^2$=H, CH=CH$_2$, CCH); B. W. Bycroft, S. R. Chabra, *J. Chem. Soc. Chem. Commun.* 1989, 423-425 ($R^1$=H; $R^2$=CH$_2$COOtBu; Y. Xu, J. Choi, M. I. Calaza, S. Turner, H. Rapoport, *J. Org. Chem.* 1999, 64, 4069-4078 ($R^1$=H; $R^2$=3-pyridyl); E. M. Khalil, W. J. Ojala, A. Pradham, V. D. Nair, W. B. Gleason, *J. Med. Chem.* 1999, 42, 628-637; E. M. Khalil, N. L. Subasinghe, R. L. Johnson, *Tetrahedron Lett.* 1996, 37, 3441-3444 ($R^1$=allyl; $R^2$=H); A. DeNicola, J. -L. Luche, *Tetrahedron Lett.* 1992, 33, 6461-6464; S. Thaisrivongs, D. T. Pals, J. A. Lawson, S. Turner, D. W. Harris, *J. Med. Chem.* 1987, 30, 536-541; E. M. Khalil, N. L. Subasinghe, R. L. Johnson, *Tetrahedron Lett.* 1996, 37, 3441-3444; A. Lewis, J. Wilkie, T. J. Rutherford, D. Gani, *J. Chem. Soc. Perkin Trans.* 1, 1998, 3777-3794 ($R^1$=Me; $R^2$=H); A. Lewis, J. Wilkie, T. J. Rutherford, D. Gani, *J. Chem. Soc. Perkin Trans.* 1, 1998, 3777-3794 ($R^1$=CH$_2$COOMe; $R^2$=H); N. L. Subasinghe, E. M. Khalil, R. L. Johnson, *Tetrahedron Lett.* 1997, 38, 1317-1320 ($R^1$=CH$_2$CHO; $R^2$=H); D. J. Witter, S. J. Famiglietti, J. C. Gambier, A. L. Castelhano, *Bioorg. Med. Chem. Lett.* 1998, 8, 3137-3142; E. H. Khalii, W. H. Ojada, A. Pradhar, V. D. Nair, W. B. Gleason, *J. Med. Chem.* 1999, 42, 628-637 ($R^1$=CH$_2$CH$_2$CHO; $R^2$=H).

A6: See DeNardo, *Farnaco Ed. Sci.* 1977, 32, 522-529 ($R^1$=H; $R^3$=H); P. J. T. Floris, N. Terhuis, H. Hiemstra, N. W. Speckamp, *Tetrahedron,* 1993, 49, 8605-8628; S. Kanemasa, N. Tomoshige, O. Tsuge, *Bull. Chem. Soc. Jpn.* 1989, 62, 3944-3949 ($R^1$=H; $R^3$=H); Sucrow, *Chem. Ber.* 1979, 112, 1719.

A7: See Fichter, *J. Prakt. Chem.* 1906, 74, 310 ($R^1$=Me; $R^3$=Ph).

A8: See L. Lapantsanis, G. Milias, K. Froussios, M. Kolovos, *Synthesis* 1983, 641-673; H. Nedev, H. Naharisoa, *Tetrahedron Lett.* 1993, 34, 4201-4204; D. Y. Jackson, C. Quan, D. R Artis, T. Rawson, B. Blackburn, *J. Med. Chem.* 1997, 40, 3359-3368; D. Konopinska, H. Bartosz-Bechowski, G. Rosinski, W. Sobotka, *Bull. Pol. Acad. Sci. Chem.* 1993, 41, 2740; J. Hondrelis, G. Lonergan, S. Voliotis, J. Matsukas, *Tetrahedron* 1990, 46, 565-576; T. Nakamura, H. Matsuyama, H. Kanigata, M. Iyoda, *J. Org. Chem.* 1992, 57, 3783-3789; C. E. O'Connell, K. Ackermann, C. A. Rowell, A. Garcia, M. D. Lewis, C. E. Schwartz, *Bioorg. Med. Chem. Lett.* 1999, 9, 2095-2100; G. Lowe, T. Vilaivan, *J. Chem. Soc. Perkin Trans.* 1997, 547-554; B. Bellier, L. McCourt-Tranchepain, B. Ducos, S. Danascimenta, H. Mundal, *J. Med. Chem.* 1997, 40, 3947-3956; M. Peterson, R. Vince *J. Med. Chem.* 1991, 34, 2787-2797; E. M. Smith, G. F. Swiss, B. R. Neustadt, E. H. Gold, J. A. Sommer, *J. Med. Chem.* 1988, 31, 875-885; E. Rubini, C. Gilon, Z. Selinger, M. Chorev, *Tetrahedron* 1986, 42, 6039-6045 ($R^1$=H; $R^5$=OH); C. R. Noe, M. Knollmueller, H. Voellenkle, M. Noe-Letschnig, A. Weigand, J. Mühl, *Pharmazie,* 1996, 51, 800-804 ($R^1$=CH$_3$; $R^5$=OH); J. Kitchin, R. C. Berthell, N. Cammack, S. Dolan, D. N. Evans, *J. Med. Chem.* 1994, 37, 3703-3716; D. Y. Jackson, C. Quan, D. R. Artis, T. Rawson, B. Blackburn, *J. Med. Chem.* 1997, 40, 3359-3368 ($R^1$=H; $R^5$=OBn); J. E. Baldwin, A. R. Field, C. C. Lawrence, K. D. Merritt, C. J. Schofield, *Tetrahedron Lett.* 1993, 34, 7489-7492; K. Hashimoto, Y. Shima, H. Shirahama, *Heterocycles* 1996, 42, 489-492 ($R^1$=H; $R^5$=OTs); T. R. Webb, C. Eigenbrot, *J. Org. Chem.* 1991, 56, 3009-3016; D. C. Cafferty, C. A. Slate, B. M. Nakhle, H. D. Graham, T. L. Anstell, *Tetrahedron* 1995, 51, 9859-9872 ($R^1$=H; $R^5$=NH$_2$); T. R. Webb, C. Eigenbrot, *J. Org. Chem.* 1991, 56, 3009-3016 ($R^1$=H; $R^5$=CH$_2$NH$_2$); J. K. Thottathil, J. L. Moniot, *Tetrahedron Lett.* 1986, 27, 151-154 ($R^1$=H; $R^5$=Ph); K. Plucinska, T. Kataoka, M. Yodo, W. Cody, *J. Med. Chem.* 1993, 36, 1902-1913 ($R^1$=H; $R^5$=SBn); J. Krapcho, C. Turk, D. W. Cushman, J. R. Powell, *J. Med. Chem.* 1988, 31, 1148-1160 ($R^1$=H; $R^5$=SPh); A. J. Verbiscar, B. Witkop, *J. Org. Chem.* 1970, 35, 1924-1927 ($R^1$=H; $R^5$=SCH$_2$(4-OMe)C$_6$H$_4$); S. L Klein, J. M. Denner, B. F. Molino, C. Gardner, R. D'Alisa, *Bioorg. Med. Chem. Lett.* 1996, 6, 2225-2230 ($R^1$=H; $R^5$=O(CH$_2$)$_3$Ph); R. Zhang, F. Brownewell, J. S. Madalengoita, *Tetrahedron Lett.* 1999, 40, 2707-2710 ($R^1$=H; $R^5$=CH$_2$COOBn).

A9: See Blake, *J. Am. Chem. Soc.* 1964, 86, 5293-5297; J. Cooper, R. T. Gallagher, D. T. Knight, *J. Chem. Soc. Chem. Perkin Trans.* 1, 1993, 1313-1318; D. W. Knight, A. W. Sibley, *J. Chem. Soc. Perkin Trans.* 1, 1997, 2179, 2188 ($R^1$=H; $R^6$=H); Blake, *J. Am. Chem. Soc.* 1964, 86, 5293-5297; Y.

Yamada, T. Ishii, M. Kimura, K. Hosaka, *Tetrahedron Lett.* 1981, 1353-1354 ($R^1$=H; $R^6$=OH); Y. Umio, *Yakugaku Zsshi*, 1958, 78, 727 ($R^1$=H; $R^6$=iPr); Miyamoto, *Yakugaku Zasshi*, 1957, 77, 580-584; Tanaka, *Proc. Jpn. Acad.* 1957, 33, 47-50 ($R^1$=H; $R^6$=CH(CH$_3$)CH$_2$N(CH$_3$)$_2$); L. E. Overman, B. N. Rodgers, J. E. Tellew, W. C. Trenkle, *J. Am. Chem. Soc.* 1997, 119, 7159-7160 ($R^1$=H; $R^6$=allyl); Ohki, *Chem. Pharm. Bull.* 1976, 24, 1362-1369 ($R^1$=CH$_3$; $R^6$=H).

A10: See J. Mulzer, A. Meier, J. Buschmann, P. Luger, *Synthesis* 1996, 123-132 ($R^1$=H; $R^7$=CH=CH$_2$); J. Cooper, P. T. Gallagher, D. W. Knight, *J. Chem. Soc. Chem. Commun.* 1988, 509-510; E. Gotschi, C. Jenny, P. Reindl, F. Ricklin, *Helv. Chim. Acta* 1996, 79, 2219-2234 ($R^1$=H; $R^7$=OH); N. A. Sasaki, R. Pauli, C. Fontaine, A. Chiaroni, C. Riche, P. Potier, *Tetrahedron Lett.* 1994, 35, 241-244 ($R^1$=H; $R^7$=COOH); R. Cotton, A. N. C. Johnstone, M. North, *Tetrahedron* 1995, 51, 8525-8544 ($R^1$=H; $R^7$=COOMe); J. S. Sabol, G. A. Flynn, D. Friedrich, E. W. Huber, *Tetrahedron Lett.* 1997, 38, 3687-3690 ($R^1$=H; $R^7$=CONH$_2$); P. P. Waid, G. A. Flynn, E. W. Huber, J. S. Sabol, *Tetrahedron Lett.* 1996, 37, 4091-4094 ($R^1$=H; $R^7$=(4-BnO)C$_6$H$_4$); N. A. Sasaki, R. Pauli, P. Potier, *Tetrahedron Lett.* 1994, 35, 237-240 ($R^1$=H; $R^7$=SO$_2$Ph); R. J. Heffner, J. Jiang, M. Jouillié, *J. Am. Chem. Soc.* 1992, 114, 10181-10189; U. Schmidt, H. Griesser, A. Lieberknecht, J. Häusler, *Angew. Chem.* 1981, 93, 272-273 ($R^1$=H; $R^7$=OAryl); H. Mosberg, A. L. Lomnize, C. Wang, H. Kroona, D. L. Heyl, *J. Med. Chem.* 1994, 37, 4371-4383 ($R^1$=H; $R^7$=4-OHC$_6$H$_4$); S. A. Kolodziej, G. V. Nikiforovich, R. Sceean, M. -F. Lignon, J. Martinez, G. R. Marshall, *J. Med. Chem.* 1995, 38, 137-149 ($R^1$=H; $R^7$=SCH$_2$(4-Me)C$_6$H$_4$).

A11: See Kuhn, Osswald, *Chem. Ber.* 1956, 89, 1423-1434; Patchett, Witkop, *J. Am. Chem. Soc.* 1957, 79, 185-189; Benz, *Helv. Chim. Acta* 1974, 57, 2459-2475; P. Wessig, *Synlet,* 1999, 9, 1465-1467; E. M. Smit, G. F. Swiss, B. R. Neustadt, E. H. Gold, J. A. Sommer, *J. Med. Chem.* 1988, 31, 875-885; J. Krapcho, C. Turk, D. W. Cushman, J. R. Powell, J. M. DeForrest, *J. Med. Chem.* 1988, 31, 1148 ($R^1$=H; $R^6$=H); D. BenIshai, S. Hirsh, *Tetrahedron* 1988, 44, 5441-5450 ($R^1$=H; $R^6$=CH$_3$); M. W. Holladay, C. W. Lin, C. S. Garvey, D. G. Witte, *J. Med. Chem.* 1991, 34, 455-457 ($R^1$=H; $R^6$=allyl); P. Barralough, P. Hudhomme, C. A. Spray, D. W. Young, *Tetrahedron* 1995, 51, 4195-4212 ($R^1$=H; $R^6$=Et); J. E. Baldwin, M. Rudolf, *Tetrahedron Lett.* 1994, 35, 6163-6166; J. E. Baldwin, S. J. Bamford, A. M. Fryer, M. Rudolf, M. E. Wood, *Tetrahedron* 1997, 53, 5233-5254 ($R^1$=H; $R^6$=CH$_2$COOtBu); P. Gill, W. D. Lubell, *J. Org. Chem.* 1995, 60, 2658-2659 ($R^1$=H; $R^6$=CH$_3$; Bn; allyl; CH$_2$COOMe); M. J. Blanco, F. J. Sardina, *J. Org. Chem.* 1998, 63, 3411-3466 ($R^1$=H; $R^6$=OCH$_2$OMe).

A12: See Ahmed, Cheeseman, *Tetrahedron* 1977, 33, 2255-2257; J. S. New, J. P. Yevich, *J. Heterocycl. Chem.* 1984, 21, 1355-1360; R. Kikumoto, Y. Tamao, K. Obkubo, T. Tezuka, S. Tonomura, *J. Med. Chem.* 1980, 23, 1293-1299; C. J. Blankley, J. S. Kaltenbronn, D. E. DeJohn, A. Werner, L. R. Bennett, *J. Med Chem.* 1987, 30, 992-998; S. Klutcho, C. J. Blankley, R. W. Fleming, J. M. Hinkley, R. E. Werner, *J. Med. Chem.* 1986, 29, 1953-1961 ($R^1$=H; $R^8$=H); L. J. Beeley, C. J. M. Rockwell, *Tetrahedron Lett.* 1990, 31, 417-420 ($R^1$=COOEt; $R^8$=H).

A13: See G. Flouret, W. Brieher, T. Majewski, K. Mahan, *J. Med. Chem.* 1991, 43, 2089-2094; G. Galiendo, P. Grieco, E. Perissuti, V. Santagada, *Farmaco,* 1996, 51, 197-202; D. F. McComsey, M. J. Hawlins, P. Andrade-Gordon, M. F. Addo, B. E. Maryanoff, *Bioorg. Med. Chem. Lett.* 1999, 9, 1423-1428; G. B. Jones, S. B. Heaton, B. J. Chapman, M. Guzel, *Tetrahedron: Asymmetry* 1997, 8, 3625-3636; M. Asami, H. Watanabe, K. Honda, S. Inoue, *Tetrahedron: Asymmetry* 1998, 9, 4165-4174; K. Gross, Y. M. Yun, P. Beak, *J. Org. Chem.* 1997, 62, 7679-7689 ($R^1$=H; $R^6$=H; $R^8$=H); R. Gross, Y. M. Yun, P. Beak, *J. Org. Chem.* 1997, 62, 7679-7689 ($R^1$=H; $R^6$=H; $R^8$=6-Cl); Ch. Noe, M. Knollmueller, C. Schoedl, M. L. Berger, *Sci. Pharm.* 1996, 64, 577-590; E. Reiman, W. Erdle, H. Unger, *Pharmazie,* 1994, 54, 418-421 ($R^1$=H; $R^6$=CH$_2$COOH; $R^8$=H); V. Collot, M. Schmitt, A. K. Marwah, B. Norberg, J. -J. Bourgignon, *Tetrahedron Lett.* 1997, 38, 8033-8036 ($R^1$=H; $R^6$=Ph; $R^8$=H); L. V. Dunkerton, H. Chen, B. P. McKillican, *Tetrahedron Lett.* 1988, 29, 2539-2542 ($R^1$=C(CH$_3$)$_2$CH=CH$_2$; $R^6$=H; $R^8$=H); E. J. Corey, *J. Am. Chem. Soc.* 1970, 92, 2476-2488; Neunhoeffer, Lehmann, *Chem. Ber.* 1961, 94, 2960-2963 ($R^1$=CH$_3$; $R^6$=H; $R^8$=H).

A14: Amino acids of type A14 can be made according to Scheme 1.

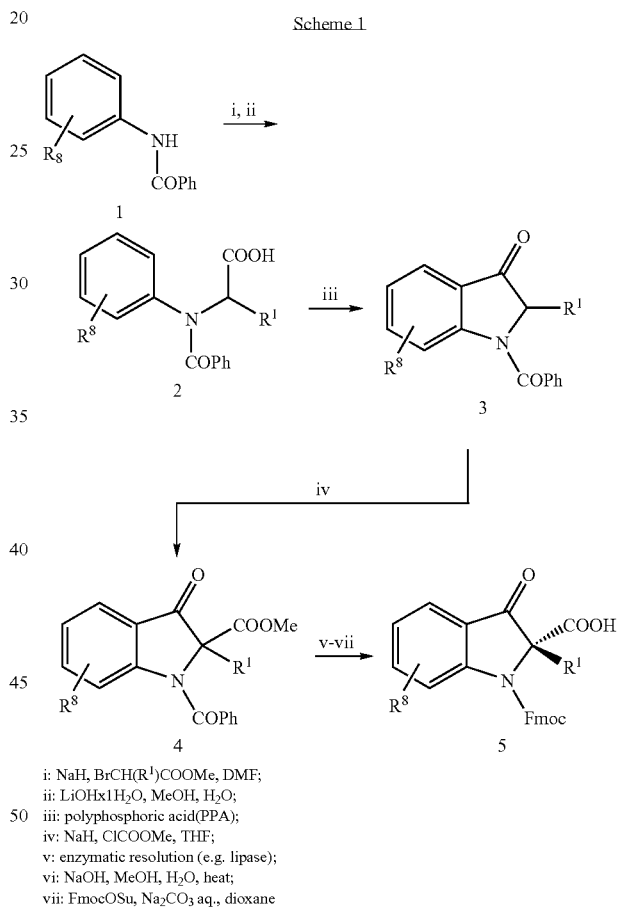

i: NaH, BrCH(R$^1$)COOMe, DMF;
ii: LiOHx1H$_2$O, MeOH, H$_2$O;
iii: polyphosphoric acid(PPA);
iv: NaH, ClCOOMe, THF;
v: enzymatic resolution (e.g. lipase);
vi: NaOH, MeOH, H$_2$O, heat;
vii: FmocOSu, Na$_2$CO$_3$ aq., dioxane A15: See D. S. Perlow, J. M. Erb, N. P. Gould, R. D. Tung, R. M. Freidinger, *J. Org. Chem.* 1992, 57, 4394-4400; D. Y. Jackson, C. Quan, D. R. Artis, T. Rawson, B. Blackburn, *J. Med. Chem.* 1997, 40, 3359-3368 ($R^1$=H; $R^2$=H); H. H. Wasserman, K. Rodrigues, K. Kucharczyk, *Tetrahedron Lett.* 1989, 30, 6077-6080 ($R^1$=H; $R^2$=COOH).

A16: See Beyerman, Boekee, *Recl. Trav. Chim. Pays-Bas,* 1959, 78, 648-653; M. E. Freed, A. R. Day, *J. Org. Chem.* 1960, 25, 2105-2107; D. R. Adams, P. D. Bailey, I. D. Collier, J. D. Heferman, S. Slokes, *J. Chem. Soc. Chem. Commun.* 1996, 349-350; J. E. Baldwin, R. M. Adlington, C. R. A. Godfrey, D. W. Collins, J. D. Vaughan, *J. Chem. Soc. Chem.*

Commun. 1993, 1434-1435; Y. Matsumura, Y. Takeshima, H. Ohita, *Bull. Chem. Soc. Jpn.* 1994, 67, 304-306 ($R^1$=H; $R^6$=H); C. Herdeis, W. Engel, *Arch. Pharm.* 1991, 324, 670 ($R^1$=COOMe; $R^6$=$CH_3$).

A17, A18: See C. R. Davies, J. S. Davies, *J. Chem. Soc. Perkin Trans* 1, 1976, 2390-2394; K. Bevan, *J. Chem. Soc.* C, 1971, 514-522; K. Umezawa, K. Nakazawa, Y. Ikeda, H. Naganawa, S. Kondo, *J. Org. Chem.* 1999, 64, 3034-3038 ($R^1$=$R^3$=H); P. D. Williams, M. G. Bock, R. D. Tung, V. M. Garsky, D. S. Parlow, *J. Med. Chem,* 1992, 35, 3905-3918; K. Tamaki, K. Tanzawa, S. Kurihara, T. Oikawa, S. Monma, *Chem. Pharm. Bull.* 1995, 43, 1883-1893 ($R^1$=$R^5$=H; $R^3$=COOBn); K. J. Hale, J. Cai, V. Delisser, S. Manaviazar, S. A. Peak, *Tetrahedron* 1996, 52, 1047-1068; M. H. Chen, O. P. Goel, J. -W. Hyun, J. Magano, J. R. Rubin, *Bioorg. Med. Chem. Lett.* 1999, 9, 1587-1592 ($R^1$=$R^5$=H; $R^3$=COOtBu), R. Baenteli, I. Brun, P. Hall, R. Metternich, *Tetrahedron Lett.* 1999, 40, 2109-2112 ($R^1$=$R^5$=H; $R^3$=COR); K. J. Hale, N. Jogiya, S. Manaviazar, *Tetrahedron* 1998, 39, 7163-7166 ($R^1$=H; $R^3$=COOBn; $R^5$=OBn); T. Kamenecka, S. J. Danishewsky, *Angew Chem. Int. Ed. Engl.* 1998, 37, 2995-2998 ($R^1$=H; $R^3$=COO$(CH_2)_2$ $SiMe_3$; $R^5$=$OSiMe_2tBu$.

A19: See Beilstein, Registry Number 648833 ($R_1$=$R^4$=$R^8$=H). Compounds of this type can be prepared according to Scheme 2.

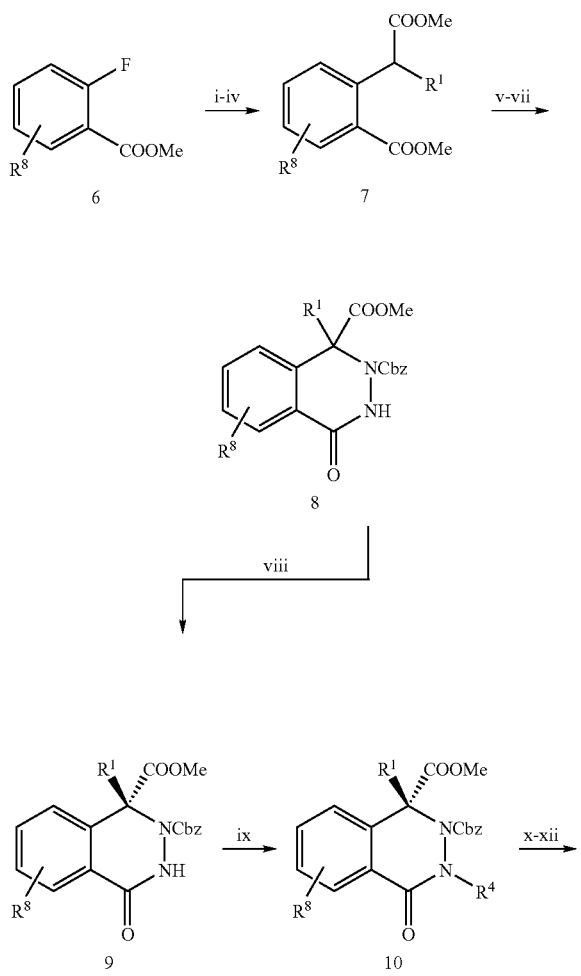

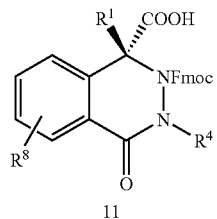

i: NaH, $CH_2(COOMe)_2$, DMSO;
ii: NaH, $R^1$—X, DMSO;
iii: NaOH aq., MeOH, 75°;
iv: DBU, MeI, DMF;
v: LDA, BocN=NBoc;
vi: TFA, $CH_2Cl_2$;
vii: CbzCl, $Na_2CO_3$ aq., dioxane;
viii: enzymatic resolution (e.g. lipase); then DBU, MeI, DMF;
ix: NaH, $R^4$—X, THF;
x: Pd/C, $H_2$, EtOH;
xi: LiOHx1$H_2O$, MeOH, $H_2O$;
xii: FmocOSu, $Na_2CO_3$ aq., dioxane A20: See D. Hagiwara, H Miyake, N. Igari, M. Karino, Y. Maeda, *J. Med. Chem.* 1994, 37, 2090-2099 ($R^1$=H; $R^9$=OH); Y. Arakawa, M. Yasuda, M. Ohnishi, S. Yoshifuji, *Chem. Pharm. Bull.* 1997, 45, 255-259 ($R^1$=H; $R^9$=COOH); P. J. Murray, I. D. Starkey, *Tetrahedron Lett.* 1996, 37, 1875-1878 ($R^1$=H; $R^9$=$(CH_2)_2NHCOCH_2Ph$); K. Clinch, A. Vasella, R. Schauer, *Tetrahedron Lett.* 1987, 28, 6425-6428 ($R^1$=H; $R^9$=NHAc).

A21: See A. Golubev, N. Sewald, K. Burger, *Tetrahedron Lett.* 1995, 36, 2037-2040; F. Machetti, F. M. Cordero, F. DeSario, A. Guarna, A. Brandi, *Tetrahedon Lett.* 1996, 37, 4205-4208; P. L. Ornstein, D. D. Schoepp, M. B. Arnold, J. D. Leander, D. Lodge, *J. Med. Chem.* 1991, 34, 90-97; $R^1$=$R^6$=H); P. D. Leeson, B. J. Williams, R. Baker, T. Ludduwahetty, K. W. Moore, M. Rowley, *J. Chem. Soc. Chem. Commun.* 1990, 1578-1580; D. I. C. Scopes, N. F. Hayes, D. E. Bays, D. Belton, J. Brain, *J. Med. Chem.* 1992, 35, 490-501; H. Kessler, M. Kuehn, T. Löschner, *Liebigs Ann. Chem.* 1986, 1-20 ($R^1$=$R^6$=H); C. Herdeis, W. Engel, *Arch. Pharm.* 1992, 7, 419-424 ($R^1$=$R^6$=Bn); C. Herdeis, W. Engel, *Arch. Pharm.* 1992, 411-418 ($R_1$=COOMe; $R^6$=H); C. Herdeis, W. Engel, *Arch Pharm.* 1992, 419-424 ($R^1$=COOMe; $R^6$=Bn).

A22: See P. D. Leeson, B. J. Williams, R. Baker, T. Ladduwahetty, K. W. Moore, M. Rowley, *J. Chem. Soc. Chem. Comm.* 1990, 1578-1580 ($R^1$=H; $R^{10}$=NHOBn).

A23: See Beyerman, Boekee, *Recl. Trav. Chim. Pays-Bas* 1959, 78, 648-653; D. R. Adams, P. D. Bailey, I. D. Collier, J. D. Heffernan, S. Stokes *J. Chem. Soc. Chem. Commun.* 1996, 349-350; J. E. Baldwin, R. M. Adlington, C. Godfrey, D. W. Collins, J. G. Vaughan, *J. Chem. Soc. Chem. Comm.* 1993, 1434-1435 ($R^1$=$R^6$=H); C. Herdeis, W. Engel, *Arch. Pharm.* 1993, 297-302 ($R^1$=COOMe; $R^6$=H).

A24: See Plieninger, Leonhäuser, *Chem. Ber.* 1959, 92, 1579-1584; D. W. Knight, N. Lewis, A. C. Share, D. Haigh, *J. Chem. Soc. Perkin Trans.* 1 1998, 22, 3673-3684; J. Drummond, G. Johnson, D. G. Nickell, D. F. Ortwine, R. F. Bruns, B. Welbaum, *J. Med. Chem.* 1989, 32, 2116-2128; M. P. Moyer, P. L. Feldman, H. Rapoport, *J. Org. Chem.* 1985, 50, 5223-5230 ($R^1=R^6=H$); McElvain, Laughton, *J. Am. Chem. Soc.* 1951, 73, 448-451 (R=H; $R^6$=Ph); McElvain, Laughton, *J. Am. Clem. Soc.* 1951, 73, 448-451 ($R^1$=Ph, $R^6$=H);

A25: See L.-Y. Hu, T. R. Ryder, S. S. Nikam, E. Millerman, B. G. Szoke, M. F. Rafferty, *Bioorg. Med. Chem. Lett.* 1999, 9, 1121-1126; W. C. Lumma, R. D. Hartman, W. S. Saari, E. L. Engelhardt, V. J. Lotti, C. A. Stone, *J. Med. Chem.* 1981, 24, 93-101; N. Hosten, M. J. O. Antenuis, *Bull. Soc. Chim. Belg.* 1988, 97, 48-50; C. F. Bigge, S. J. Hays, P. M. Novak, J. T. Drummond, G. Johnson, T. P. Bobovski, *Tetrahedron Lett.* 1989, 30, 5193-5191; B. Aebischer, P. Frey, H.-P. Haerter, P. L. Herrling, W. Müller, *Helv. Chim. Acta* 1989, 72, 1043-1051; W. J. Hoeckstra, B. E. Maryanoff, B. P. Damiano, P. Andrade-Gordon, J. H. Cohen, M. J. Constanzo, B. J. Haertlein, L. R. Hecker, B. L. Hulshizer, J. A. Kauffman, P. Keane, *J. Med. Chem.* 1999, 42, 5254-5265 ($R^1$=H; $R^{11}$=H); B. D. Dorsey, R. B. Levin, S. L. McDaniel, J. P. Vacca, J. P. Guare, *J. Med Chem.* 1994, 37, 3443-3451; M. Cheng, B. De, S. Pill, N. G. Almstaed, M. G. Natchus, M. V. Anastasio, S. J. McPhail, C. J. Snider, Y. O. Taiwo, L. Chen, C. M. Dunaway, *J. Med. Chem.* 2000, 43, 369-380; R. Kuwano, Y. Ito, *J. Org. Chem.* 1999, 64, 1232-1237 ($R^1$=H; $R^{11}$=COOtBu); J. Kitchin, R. C. Bethell, N. Cammack S. Dolan, D. N. Evans, *J. Med. Chem.* 1994, 37, 3707-3716 ($R^1$=H; $R^{11}$=COOPh); C. F. Bigge, S. J. Hays, P. M. Novak J. T. Drummond, G. Johnson, T. P. Bobovski, *J. Med. Chem.* 1990, 33, 2916-2924 ($R^1$=H; $R^1$=COOtBu; $(CH_2)_3COOEt$; $(CH_2)_3PO(Me)OH$; $CH_2PO(OH)_2$; $(CH_2)_2PO(OEt)_2$; $(CH_2)_2PO(OH)_2$).

Compounds of type A25 can also be prepared according to Scheme 3:

Scheme 3

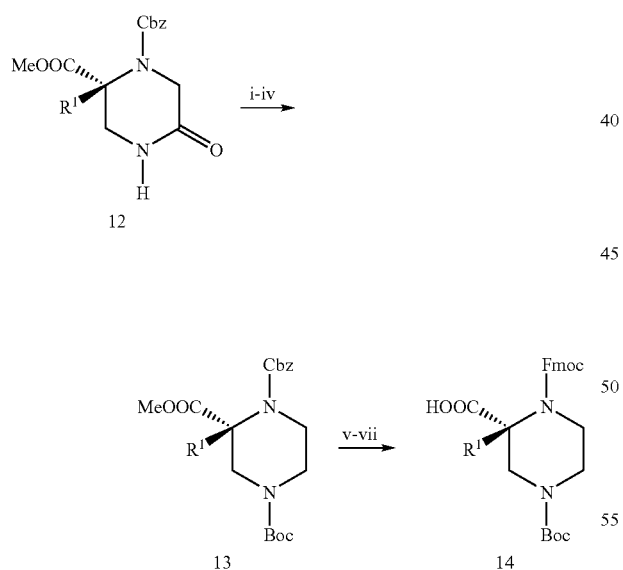

i: Lawesson reagent, toluene, 80°;
ii: DBU, MeI, DMF;
iii: $NaBH_4$ or $NaCNBH_3$, MeOH;
iv: $Boc_2O$, THF;
v: LiOH×$H_2O$, MeOH, $H_2O$;
vi: Pd/C, $H_2$, EtOH;
vii: FmocOSu, $Na_2CO_3$ aq., dioxane A26: See Koegel, *J. Biol. Chem.* 1953, 201, 547 ($R^1=R^{12}=H$).

A27: See G. Makara, G. R. Marshall, *Tetrahedron Lett.* 1997, 38, 5069-5072; R. N. Patel, A. Banerjee, R. L. Hanson, D. B. Brzozowski, L. W. Parker, L. J. Szarka, *Tetrahedron: Asymmetry* 1999, 10, 31-36 ($R^1$=H; $R^{13}$=OH, OtBu); J. E. Johanson, B. D. Christie, H. Rapoport, *J. Org. Chem.* 1981, 46, 4914-4920; N. Moss, J.-S. Duceppe, J.-M- Ferland, J. Gauthier, *J. Med. Chem.* 1996, 39, 2178-2187 ($R^1$=H; $R^{13}$=CONHMe); G. M. Makara, G. R. Marshall, *Tetrahedron Lett.* 1997, 38, 5069-5072 ($R^1$=H; $R^{13}$=$SCH_2$(4-MeO)$C_6H_4$).

A28: See A Golubev, N. Sewald, K. Burger, *Tetrahedron Lett.* 1995, 36, 2037-2040; P. L. Ornstein, D. D. Schoepp, M. B. Arnold, J. D. Leander, D. Lodge, *J. Med. Chem.* 1991, 34, 90-97 ($R^1=R^6H$=); P. D. Leeson, B. J. Williams, R. Baker, T. Ladduwahetty, K. W. Moore, M. Rowley, *J. Chem. Soc. Chem Commun.* 1990, 22, 1578-1580; C. Herdeis, W. Engel, *Arch Pharm.* 1991, 324, 670 ($R^1$=H; $R^6$=Me); C. Herdeis, W. Engel, *Arch. Pharm.* 1991, 324, 670 ($R^1$=COOMe; $R^6$=H, Me).

A29: See Kawase, Masami, *Chem. Pharm. Bull.* 1997, 45, 1248-1253; I. G. C. Coutts, J. A. Hadfield, P. R. Huddleston, *J. Chem. Res. Miniprint,* 1987, 9, 2472-2500; I. G. C. Coutts, J. A. Hadfield, P. R. Huddleston, *J. Chem. Res. Miniprint,* 1987, 9, 2472-2500; V. J. Hrubi, W. L. Cody, A M. Castrucci, M. E. Hadley, *Collect. Czech. Chem. Commun.* 1988, 53, 2549-2573; R. T. Shuman, R. B. Rothenberger, C. S. Campbell, G. F. Smith, D. S. Gifford-Moore, P. D. Gesellchen, *J. Med. Chem.* 1993, 36, 314-319; M. Kawase, Y. Okada, H. Miyamae, *Heterocycles,* 1998, 48, 285-294 ($R^1=R^3$=H); Kawase, Masami, *Chem. Pharm. Bull.* 1997, 45, 1248-1253 ($R^1$=H; $R^8$=6,7-(MeO$_2$); D. F. Ortwine, T. C. Malone, C. F. Bigge, J. T. Drummond, C. Humblet, *J. Med. Chem.* 1992, 35, 1345-1370 ($R^1$=H; $R^8$=7-$CH_2PO(OEt)_2$); E. J. Corey, D. Y. Gin, *Tetrahedron Lett.* 1996, 37, 7163-7166 ($R^1=CH_2SCOOtBu$); P. Dostert, M. Varasi, A. DellaTorre, C. Monti, V. Rizzo, *Eur. J. Med. Chim. Ther.* 1992, 27, 57-59 ($R^1$=Me; $R^8$=6,7-(OH)$_2$); Z. Czarnocki, D. Suh, D. B. McLean, P. G. Hultin, W. A. Szarek, *Can. J. Chem.* 1992, 70, 1555-1561; B. Schönenberger, A. Brossi, *Helv. Chim. Acta* 1986, 69, 1486-1497 ($R^1$=Me; $R^8$=6-OH; 7-MeO); Hahn, Stiel, *Chem. Ber.* 1936, 69, 2627; M. Chrzanowska, B. Schönenberger, A. Brossi, J. L. Flippen-Anderson, *Helv. Chim. Acta* 1987, 70, 1721-1731; T. Hudlicky, *J. Org Chem.* 1981, 46, 1738-1741 ($R^1$=Bn; $R^8$=6,7-(OH)$_2$); A. I. Meyers, M. A. Gonzalez, V. Struzka, A. Akahane, J. Guiles, J. S. Warmus, *Tetrahedron Lett.* 1991, 32, 5501-5504 ($R^1$=$CH_2$(3,4-methylenedioxy)$C_6H_3$; $R^8$=6,7-(OMe)$_2$).

A30 and A31 can be prepared according to Schemes 4 and 5.

Scheme 4

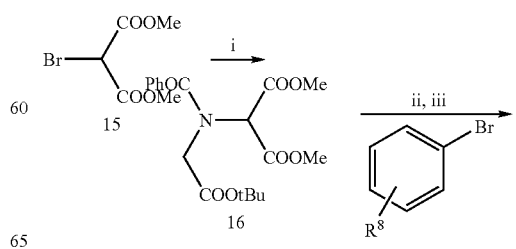

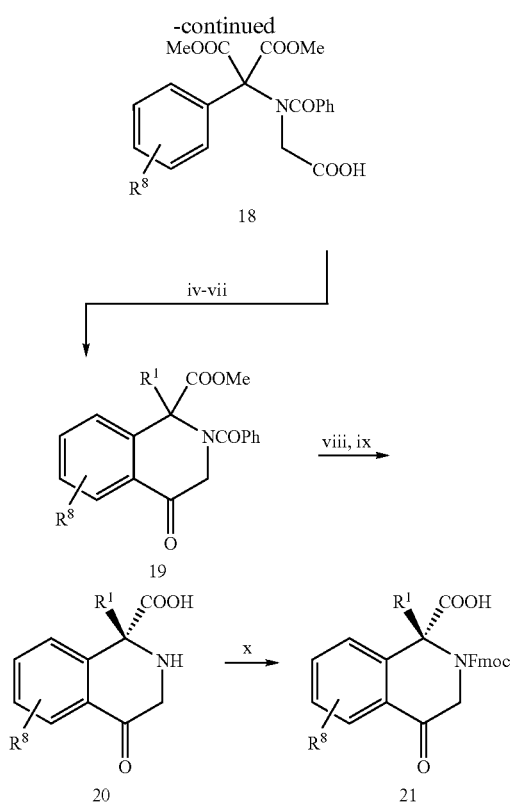

i: NaH, tert-butyl N-benzoyl glycinate, DMF;
ii: NaH, Pd(0), toluene;
iii: TFA, CH$_2$Cl$_2$;
iv: polyphosphoric acid;
v: NaOH aq., MeOH, 75°; then HCl aq.;
vi: DBU, MeI, DMF;
vii: lithium hexamethyl-disilazide, THF, chloro trimethylsilane, -78°; then R$^1$—X;
viii: enzymatic resolution (e.g. lipase); then isolation as methylester: DBU, MeI, DMF;
ix: NaOH aq., MeOH, heat;
x: FmocOSu, Na$_2$CO$_3$ aq., dioxane Scheme 5

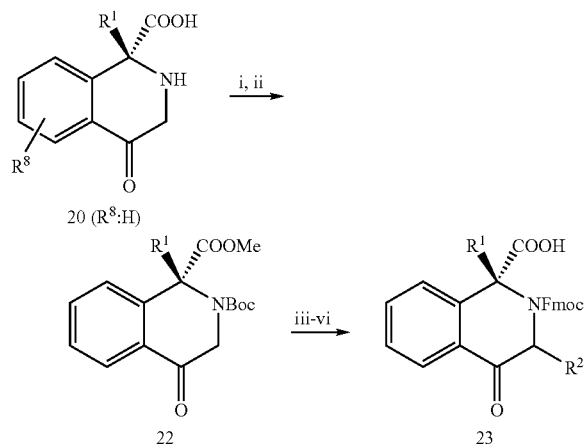

i: Boc$_2$O, Na$_2$CO$_3$ aq., dioxane;
ii: DBU, MeI, DMF;
iii: lithium hexamethyldisilazide, THF, chlorotrimethylsilane, -78°; then R$^2$—X;
iv: LiOH×1H$_2$O, MeOH, H$_2$O;
v: TFA, CH$_2$Cl$_2$;
vi: FmocOSu, Na$_2$CO$_3$ aq., dioxane A32 can be prepared according to P. W. Schiller, G. Weltrowska, T. M. -D. Nguyen, C. Lemieux, N. Nga, *J. Med. Chem.* 1991, 34, 3125-3132; V. S. Goodfellow, M. V. Marathe, K. G. Kuhlman, T. D. Fitzpatrick, D. Cuadrato, *J. Med. Chem.* 1996, 39, 1472-1484; G. Caliendo, F. Fiorino, P. Grieco, E. Perissutti, S. DeLuca, A. Guiliano, G. Santelli, D. Califano, B. Severino, V. Santagada, *Farmacao,* 1999, 54, 785-790; V. S. Goodfellow, M. V. Marathe, K. G. Kuhlman, T. D. Fitzpatrick, D. Cuadro, *J. Med. Chem.* 1996, 39, 1472-1484 (R$^1$=R$^8$=H); D. Tourwe, E. Mannekens, N. T. Trang, P. Verheyden, H. Jaspers, *J. Med. Chem.* 1998, 41, 5167-5176; A. -K Szardenings, M. Gordeev, D. V. Patel, *Tetrahedron Lett.* 1996, 37, 3635-3638; W. Wiczk, K. Stachowiak, P. Skurski, L. Lankiewicz, A. Michniewicz, A. Roy, *J. Am. Chem. Soc.* 1996, 118, 8300-8307; K. Verschuren, G. Toth, D. Tourwe, M. Lebl., G. van Binst, V. Hrubi, Synthesis 1992, 458-460 (R$^1$=H; R$^8$=6-OH); P. L. Ornstein, M. B. Arnold, N. K. Augenstein, J. W. Paschal, *J. Org. Chem.* 1991, 56, 4388-4392 (R$^1$=H; R$^5$=6-MeO); D. Ma, Z. Ma, A. P. Kozikowski, S. Pshenichkin, J. T. Wroblenski, *Bioorg. Med. Lett.* 1998, 8, 2447-2450 (R$^1$=H; R$^8$=6—COOH); U. Schöllkopf, R. Hinrichs, R. Lonsky, *Angew. Chem.* 1987, 99, 137-138 (R$^1$=Me; R$^8$=H); B. O. Kammermeier, U. Lerch, C. Sommer, *Synthesis* 1992, 1157-1160 (R$^1$=COOMe; R$^8$=H); T. Gees, W. B. Schweizer, D. Seebach, *Helv. Chim. Acta* 1993, 76, 2640-2653 (R$^1$=Me; R$^8$=6,7-(MeO)$_2$).

A33: See Hinton, Mann, *J. Chem. Soc.* 1959, 599-608.

A34: See G. P. Zecchini, M. P. Paradisi, *J. Heterocycl. Chem.* 1979, 16, 1589-1597; S. Cerrini, *J. Chem. Soc. Perkin Trans.* 1, 1979, 1013-1019; P. L. Ortstein, J. W. Paschal, P. D. Gesellchen, *J. Org. Chem.* 1990, 55, 738-741; G. M. Ksander, A. M. Yan, C. G. Diefenbacher, J. L. Stanton, *J. Med. Chem.* 1985, 28, 1606-1611; J. A. Robl, D. S. Karanewsky, M. M. Asaad, *Tetrahedron Lett.* 1995, 36, 1593-1596; S. Katayama, N. Ae, R. Nagata, *Tetrahedron: Asymmetry* 1998, 9, 4295-4300 (R$^1$=R$^8$=H); K. Hino, Y. Nagai, H. Uno, *Chem. Pharm. Bull.* 1988, 36, 2386-2400 (R$^1$=Me; R$^8$=H).

A35: See Beilstein Registry Numbers: 530775, 883013 (R$^1$=R$^8$=H).

A36: See R. W. Carling, P. D. Leeson, A. M. Moseley, R. Baker, A. C. Foster, *J. Med. Chem.* 1992, 35, 1942-1953; S. Kano, T. Ebata, S. Shibuya, *J. Chem. Soc. Perkin Trans.* 1, 1980, 2105-2111 (R$^1$=R$^8$=H); R. W. Carling, P. D. Leeson, A. M. Moseley, R. Baker, A. C. Foster, *J. Med. Chem.* 1992, 35, 1942-1953 (R$^1$=H; R$^8$=5-Cl; 7-Cl).

A37: See Nagarajan, *Indian J. Chem.* 1973, 11, 112 (R$^1$=CH$_2$COOMe; R$^8$=H).

A38: See R. Pauly, N. A. Sasaki, P. Potire, *Tetrahedron Lett.* 1994, 35, 237-240; J. Podlech, D. Seebach, *Liebigs Ann. Org. Bioorg. Chem.* 1995, 7, 1217-1228; K. C. Nicolaou, G. -Q. Shi, K. Namoto, F. Bernal, *J. Chem. Soc. Chem. Commun.* 1998, 1757-1758 (R$^1$=H; R$^2$=H).

A39: See Beilstein, Registry Number 782885.

A40: See F. P. J. C. Rutjes, N. M. Terhuis, H. Hiemstra, N. W. Speckamp, *Tetrahedron* 1993, 49, 8605-8628 (R$^1$=H; R$^3$=Bn); compounds of this type can be prepared according to Scheme 6.

Scheme 6

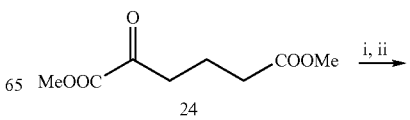

113, 9276-9286; J. F. Dellaria, B. D. Santarsiero, *Tetrahedron Lett.* 1988, 29, 6079-6082; J. F. Dellaria, B. D. Santarsiero, *J. Org. Chem.* 1989, 54, 3916-3926; J. E. Baldwin, V. Lee, C. J. Schofield, *Synlett* 1992, 249-251; J. E. Baldwin, V. Lee, C. J. Schofield, *Heterocycles* 1992, 34, 903-906.

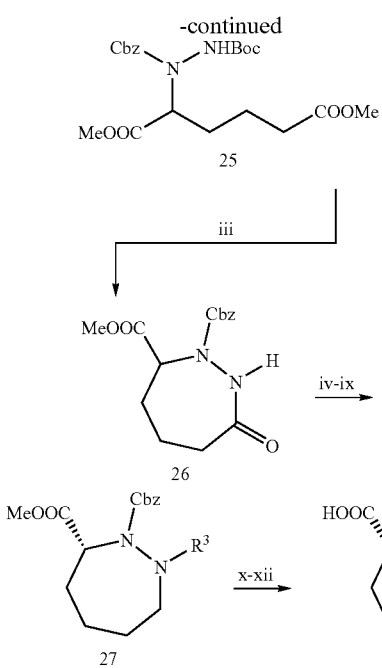

i: BocNHNH₂, NaCNBH₃, MeOH, AcOH;
ii: CbzCl, Et₃N, CH₂Cl₂;
iii: TFA, CH₂Cl₂; then pyridine, DMAP, heat;
iv: resolution (e.g. lipase);
v: DBU, MeI, DMF;
vi: Lawesson reagent, toluene, 75°;
vii: DBU, MeI, DMF;
viii: NaBH₄ or NaCNBH₃, MeOH;
ix: R³ introduced by reductive amination, alkylation or acylation;
x: LiOHx1H₂O, MeOH, H₂O;
xi: Pd/C, H₂, EtOH;
xii: FmocOSu, Na₂CO₃ aq., dioxane A41: Compounds of this type can be prepared according to Scheme 7.

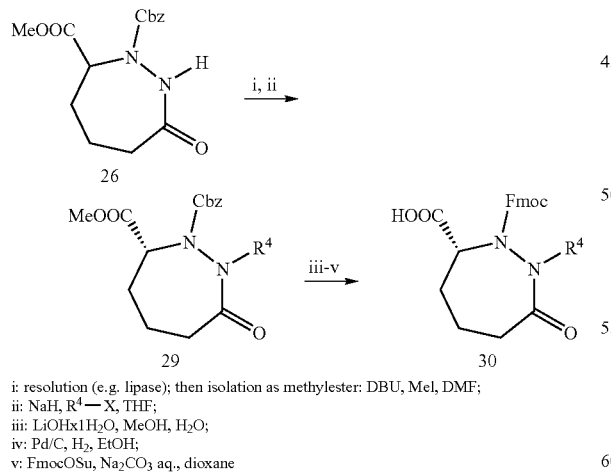

i: resolution (e.g. lipase); then isolation as methylester: DBU, MeI, DMF;
ii: NaH, R⁴—X, THF;
iii: LiOHx1H₂O, MeOH, H₂O;
iv: Pd/C, H₂, EtOH;
v: FmocOSu, Na₂CO₃ aq., dioxane A42 to A46: Compounds of this type can be prepared according to Scheme, 8 to 12. Key intermediate 34 and α-amino acid synthesis involving this building block include: R. M. Williams, M. -N. Im, *Tetrahedron Lett.* 1988, 29, 6079-6082; R. M. Williams, M. -N. Im, *J. Am. Chem. Soc.* 1991,

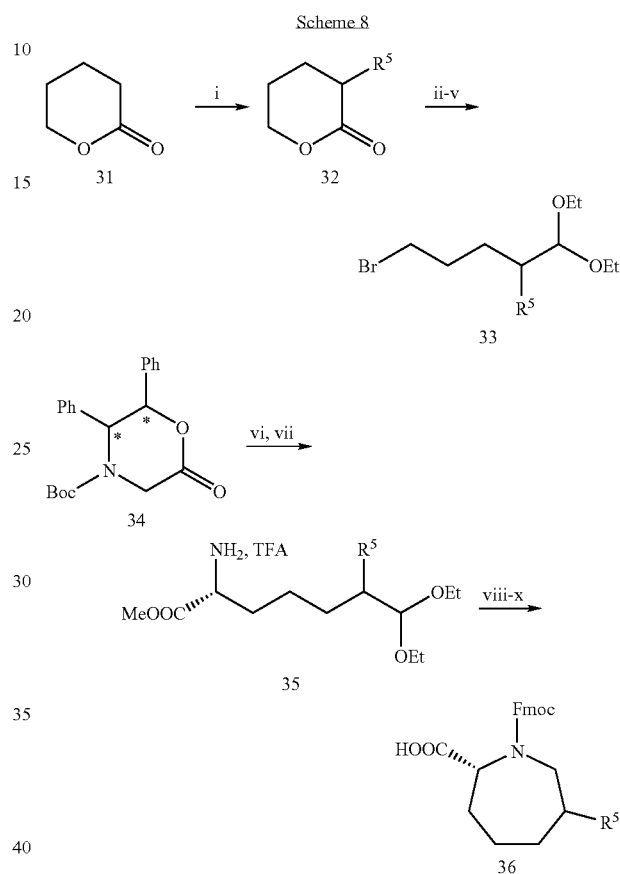

i: lithium hexamethyldisilazide, THF, chlorotrimethylsilane, -78°; then R⁵—X;
ii: HBr;
iii: DBU, MeI, DMF;
iv: DIBAL-H, THF;
v: EtOH, pyridinium p-toluenesulfonate, mol. sieves 4A;
vi: lithium hexamethyldisilazide, THF, -78°, 33;
vii: Pd/C, H₂, EtOH; then DBU, MeI, DMF; then TFA, CH₂Cl₂;
viii: HCl aq., THF; then Na(OAc)₃BH, AcOH, dichloroethane;
ix: LiOHx1H₂O, MeOH, H₂O;
x: FmocOSu, Na₂CO₃ aq., dioxane

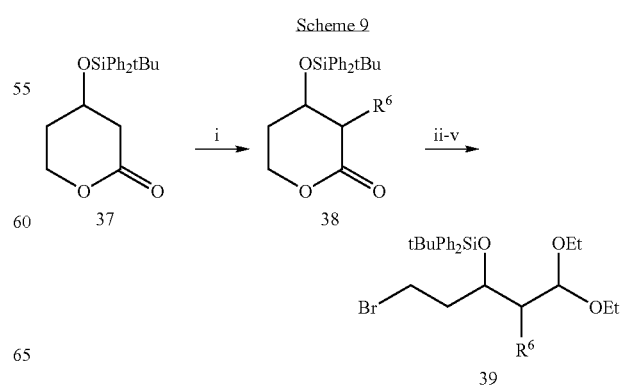

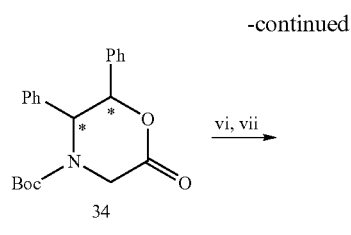

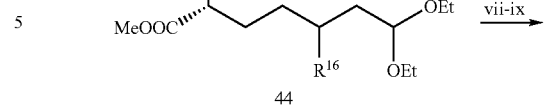

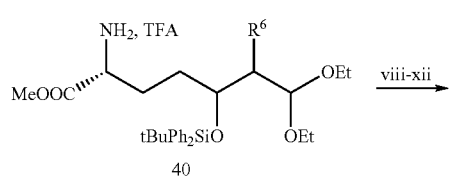

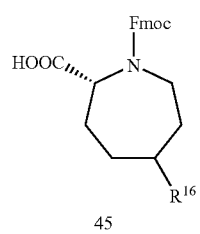

i: lithium hexamethyldisilazide, THF, chlorotrimethylsilane, -78°; then R$^6$—X;
ii: HBr;
iii: DBU, MeI, DMF;
iv: DIBAL-H, THF;
v: EtOH, pyridinium p-toluenesulfonate, mol. sieves 4A;
vi: lithium hexamethyldisilazide, THF, -78°, 39;
vii: Pd/C, H$_2$, EtOH; then DBU, MeI, DMF; then TFA, CH$_2$Cl$_2$;
viii: HCl aq., THF; then Na(OAc)$_3$BH, AcOH, dichloroethane;
viii: Boc$_2$O, Et$_3$N, CH$_2$Cl$_2$;
ix: Bu$_4$NF×10H$_2$O, THF;
ix: pyridinium chlorochromate;
x: LiOH×1H$_2$O, MeOH, H$_2$O;
xi: TFA, CH$_2$Cl$_2$;
xii: FmocOSu, Na$_2$CO$_3$ aq., dioxane i: HBr;
ii: DBU, MeI, DMF;
iii: DIBAL-H, THF;
iv: EtOH, pyridinium p-toluenesulfonate, mol. sieves 4A;
v: lithium hexamethyldisilazide, THF, -78°, 43;
vi: Pd/C, H$_2$, EtOH; then DBU, MeI, DMF; then TFA, CH$_2$Cl$_2$;
vii: HCl aq., THF; then Na(OAc)$_3$BH, AcOH, dichloroethane;
viii: LiOH×1H$_2$O, MeOH, H$_2$O;
ix: FmocOSu, Na$_2$CO$_3$ aq., dioxane Scheme 11

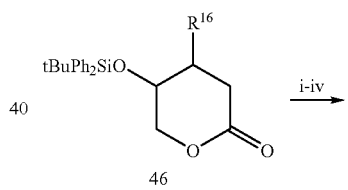

Scheme 10

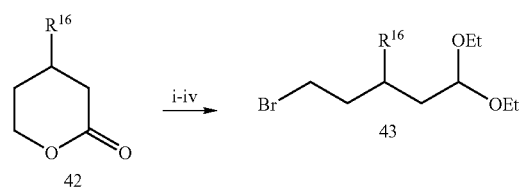

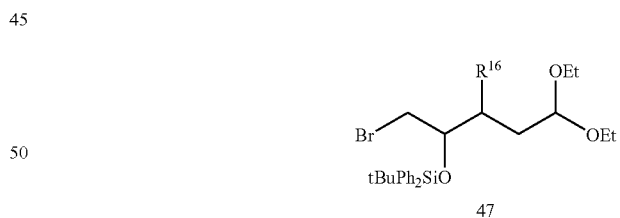

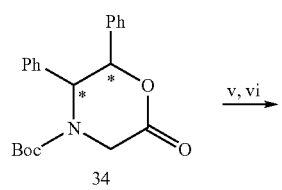

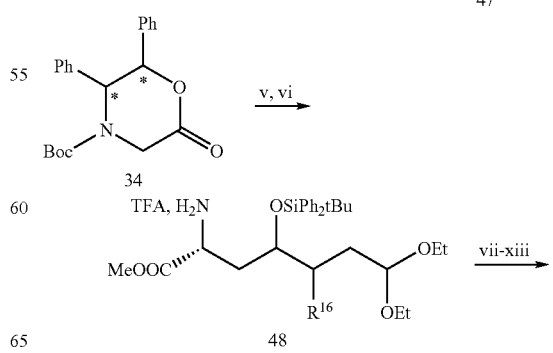

69
-continued

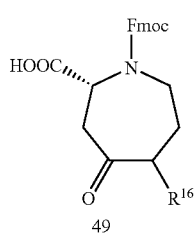
49 i: HBr;
ii: DBU, MeI, DMF;
iii: DIBAL-H, THF;
iv: EtOH, pyridinium p-toluenesulfonate, mol. sieves 4A;
v: lithium hexamethyldisilazide, THF, -78°, 47;
vi: Pd/C, H$_2$, EtOH; then DBU, MeI, DMF; then TFA, CH$_2$Cl$_2$;
vii: HCl aq., THF; then Na(OAc)$_3$BH, AcOH, dichloroethane;
viii: Boc$_2$O, Et$_3$N, CH$_2$Cl$_2$;
ix: Bu$_4$NFx10H$_2$O, THF;
x: pyridinium chlorochromate;
xi: LiOHx1H$_2$O, MeOH, H$_2$O;
xii: TFA, CH$_2$Cl$_2$;
xiii: FmocOSu, Na$_2$CO$_3$ aq., dioxane

Scheme 12

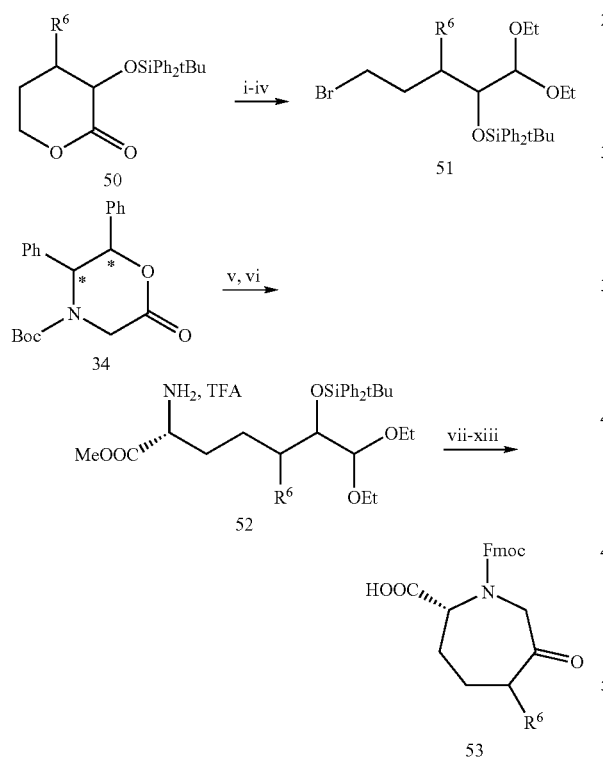

i: HBr;
ii: DBU, MeI, DMF;
iii: DIBAL-H, THF;
iv: EtOH, pyridinium p-toluenesulfonate, mol. sieves 4A;
v: lithium hexamethyldisilazide, THF, -78°, 51;
vi: Pd/C, H$_2$, EtOH; then DBU, MeI, DMF; then TFA, CH$_2$Cl$_2$;
vii: HCl aq., THF; then Na(OAc)$_3$BH, AcOH, dichloroethane;
viii: Boc$_2$O, Et$_3$N, CH$_2$Cl$_2$;
ix: Bu$_4$NFx10H$_2$O, THF;
x: pyridinium chlorochromate;
xi: LiOHx1H$_2$O, MeOH, H$_2$O;
xii: TFA, CH$_2$Cl$_2$;
xiii: FmocOSu, Na$_2$CO$_3$ aq., dioxane A47: See P. Barraclough, R. D. Farrant, D. Kettle, S. Smith, *J. Chem. Res. Miniprint* 1991, 11, 2876-2884 (R$^1$=R$^{11}$=H, Bn, (CH$_2$)$_2$PO(OEt)$_2$).

70

A48: See A. Nouvet, M. Binard, F. Lamaty, J. Martinez, R. Lazaro, *Tetrahedron* 1999, 55, 4685-4698 (R$^1$=R$^{12}$=H).

A49: See M. Y. Kolleganov, I. G. Kolleganova, M. D. Mitrofanova, L. I. Martynenko, P. P. Nazarov, V. I. Spitsyn, *Bull. Acad. Sci. USSR Div. Chem. Sci (Engl. Trans)* 1983, 32, 1293-1299; *Izv. Akad. Nauk SSSR Ser. Khim.* 1983, 6, 1293-1299; V. P. Vasilev, T. D. Orlova, S. F. Ledenkov, *J. Gen. Chem. USSR (Engl. Trans.* 1989, 59, 1629-1634; *Zh. Obshch. Khim.* 1989, 59, 1828-1833 (R$^1$=H; R$^{12}$=CH(COOH)CH$_2$COOH). Compounds of type A49 can also be prepared according to Scheme 13.

Scheme 13

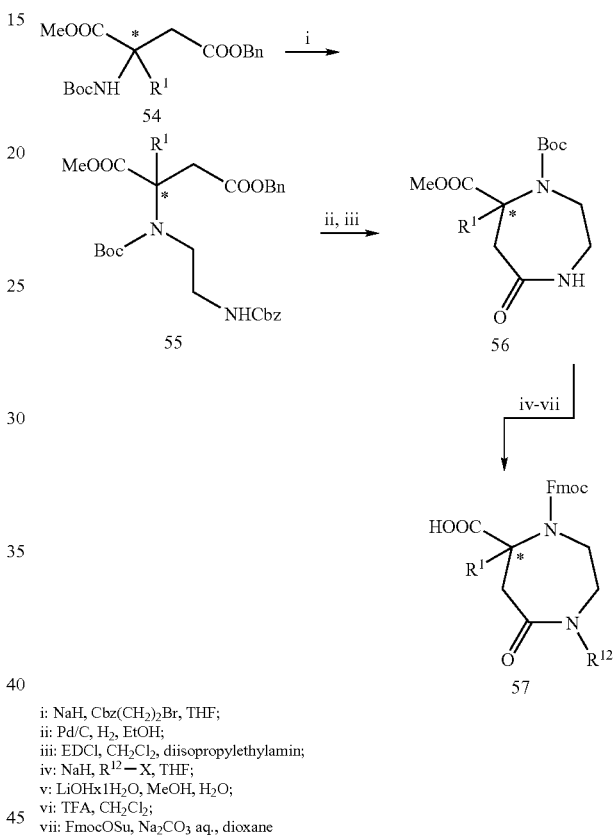

i: NaH, Cbz(CH$_2$)$_2$Br, THF;
ii: Pd/C, H$_2$, EtOH;
iii: EDCl, CH$_2$Cl$_2$, diisopropylethylamin;
iv: NaH, R$^{12}$—X, THF;
v: LiOHx1H$_2$O, MeOH, H$_2$O;
vi: TFA, CH$_2$Cl$_2$;
vii: FmocOSu, Na$_2$CO$_3$ aq., dioxane A50 and A51: Compounds of these types can be prepared according to Schemes 14 and 15.

Scheme 14

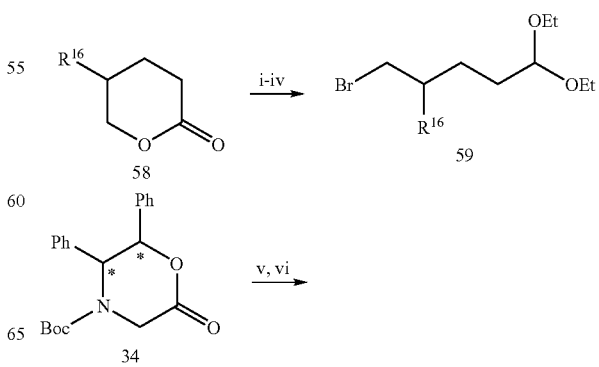

-continued

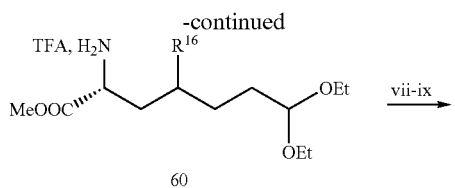

60 i: HBr;
ii: DBU, MeI, DMF;
iii: DIBAL-H, THF;
iv: EtOH, pyridinium p-toluenesulfonate, mol. sieves 4A;
v: lithium hexamethyldisilazide, THF, -78°, 59;
vi: Pd/C, H₂, EtOH; then DBU, MeI, DMF; then TFA, CH₂Cl₂;
vii: HCl aq., THF; then Na(OAc)₃BH, AcOH, dichloroethane;
viii: LiOH×1H₂O, MeOH, H₂O;
ix: FmocOSu, Na₂CO₃ aq., dioxane vii-ix →

61

-continued i: HBr;
ii: DBU, MeI, DMF;
iii: DIBAH, THF;
iv: EtOH, pyridinium p-toluenesulfonate, mol. sieves 4A;
v: lithium hexamethyldisilazide, THF, -78°, 63
vi: Pd/C, H₂, EtOH; then DBU, MeI, DMF; then TFA, CH₂Cl₂;
vii: HCl aq., THF; then Na(OAc)₃BH, AcOH, dichloroethane;
viii: Boc₂O, Et₃N, CH₂Cl₂;
ix: Bu₄NF×10H₂O, THF;
x: pyridinium chlorochromate;
xi: LiOH×1H₂O, MeOH, H₂O;
xii: TFA, CH₂Cl₂;
xiii: FmocOSu, Na₂CO₃ aq., dioxane A53: See P. Barraclough, R. D. Farrant, D. Kettle, S. Smith, *J. Chem. Res. Miniprint* 1991, 11, 2876-2884 ($R^1$=H; $R^{11}$=H; $R^1$=H; $R^{11}$=Bn, (CH₂)₃PO(OH)₂); (CH₂)₃PO(Et)₂); J. I. Levin, J. F. DiJoseph, L. M. Killar, A. Sung, T. Walter, *Bioorg. Med. Chem. Lett.* 1998, 8, 2657-2662 ($R^1$=H; $R^{11}$=4CF₃OC₆H₄CO).

A 52 and A54: Compounds of this type can be prepared according to Schemes 16 and 17.

Scheme 15

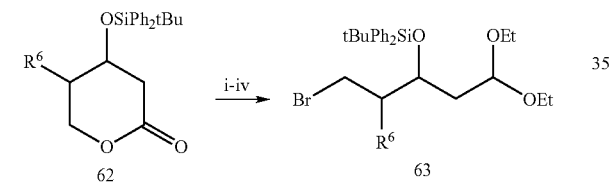

Scheme 16

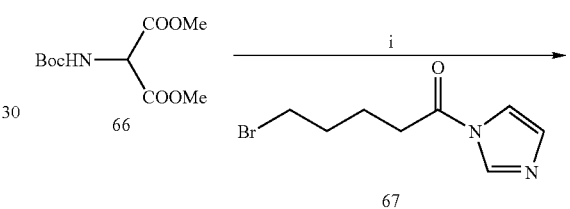

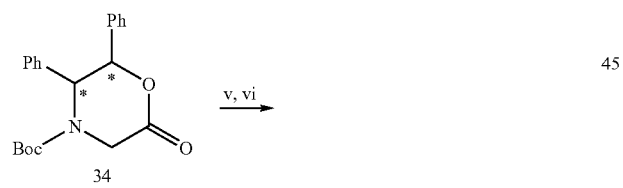

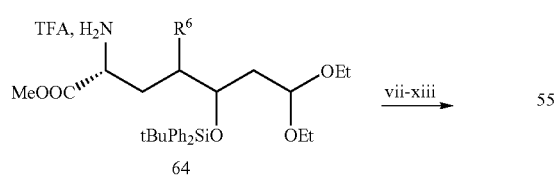

vii-xiii →

64

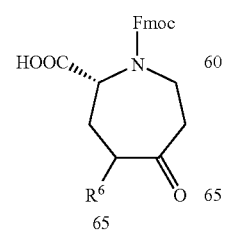

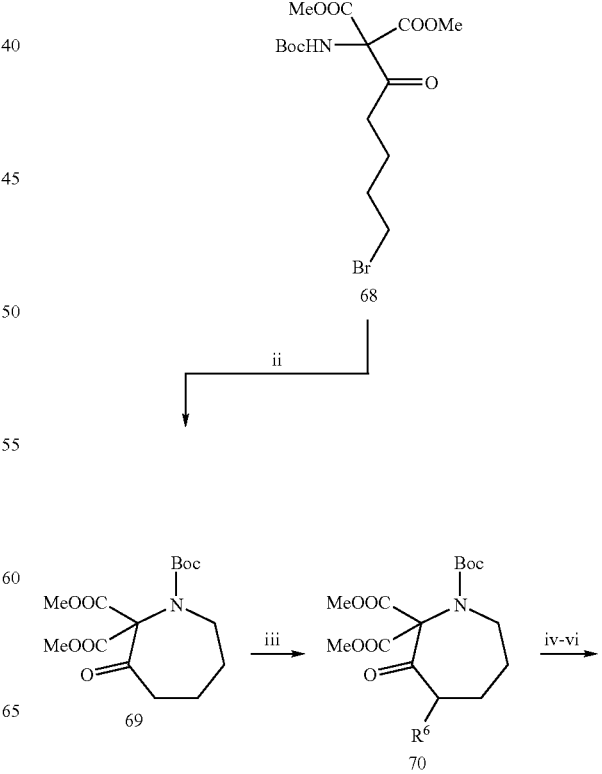

73

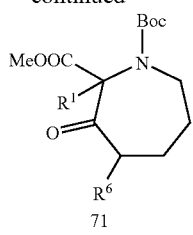

| vii

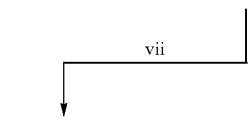

i: iBuMgCl, THF;
ii: NaH, THF;
iii: lithium hexamethyldisilazide, THF, chlorotrimetylsiane, -78°; then R⁶—X;
iv: NaOH aq., MeOH, 75°; then HCl aq.;
v: DBU, MeI, DMF;
vi: lithium hexamethyldisilazide, THF, chlorotrimetylsilane, -78°; then R¹—X;
vii: resolution (e.g. lipase); then DBU, MeI, DMF;
viii: LiOHx1H₂O, MeOH, H₂O;
ix: TFA, CH₂Cl₂;
x: FmocOSu, Na₂CO₃ aq., dioxane Scheme 17

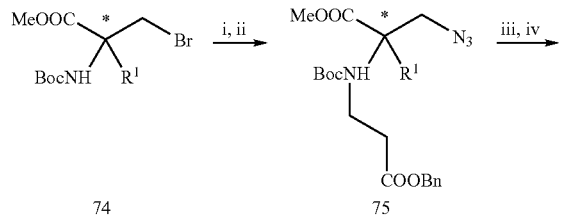

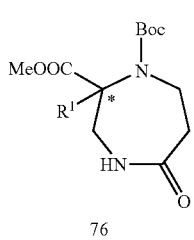

| v

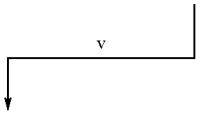

74

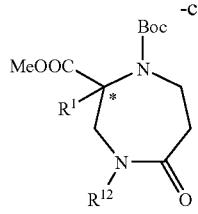 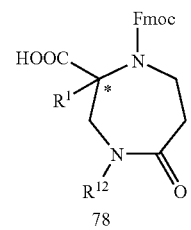

i: NaN₃, DMSO;
ii: NaH, THF, CH₂=CHCOOBn;
iii: Pd/C, H₂, EtOH;
iv: EDCl, CH₂Cl₂, diisopropylethylamine;
v: NaH, R¹²—X, THF;
vi: LiOHx1H₂O, MeOH, H₂O;
vii: TFA, CH₂Cl₂;
viii: FmocOSu, Na₂CO₃ aq., dioxane A55 and A56: Compounds of this type can be prepared according to Schemes 18 and 19.

Scheme 18

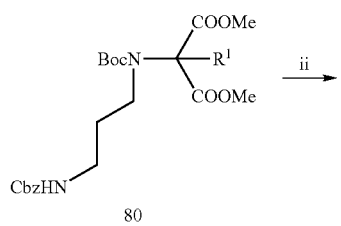

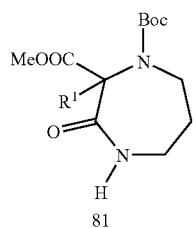

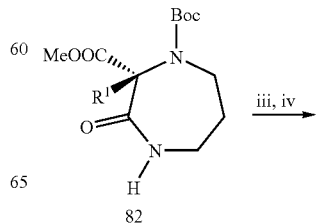

75

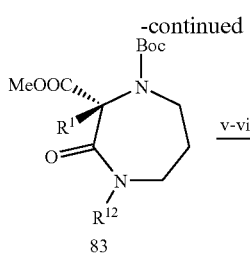 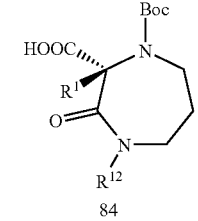

i: NaH, THF, CbzNH(CH$_2$)$_3$Br;
ii: Pd/C, H$_2$, EtOH; then toluene, heat;
iii: resolution (e.g. lipase);
iv: DBU, MeI, DMF;
v: NaH, R$^{12}$—X, THF;
vi: LiOH×1H$_2$O, MeOH, H$_2$O;
vii: TFA, CH$_2$Cl$_2$;
viii: FmocOSu, Na$_2$CO$_3$ aq., dioxane Scheme 19

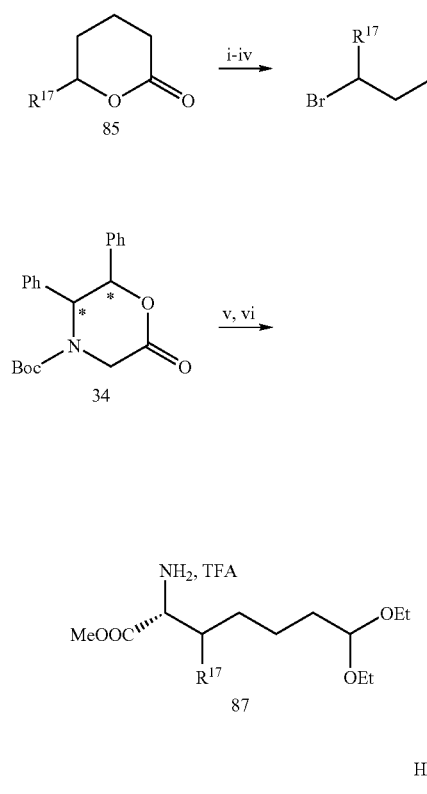

i: HBr;
ii: DBU, MeI, DMF;
iii: DIBAL-H, THF;
iv: EtOH, pyridinium p-toluenesulfonate, mol. sieves 4A;
v: lithium hexaamethyldisilazide, THF, -78°, 86
vi: Pd/C, H$_2$, EtOH; then DBU, MeI, DMF; then TFA, CH$_2$Cl$_2$;
vii: HCl aq., THF; then Na(OAc)$_3$BH, AcOH, dichloroethane;
viii: LiOH×1H$_2$O, MeOH, H$_2$O;
ix: FmocOSu, Na$_2$CO$_3$ aq., dioxane

76

A57: Compounds of this type can be prepared according to Scheme 20.

Scheme 20

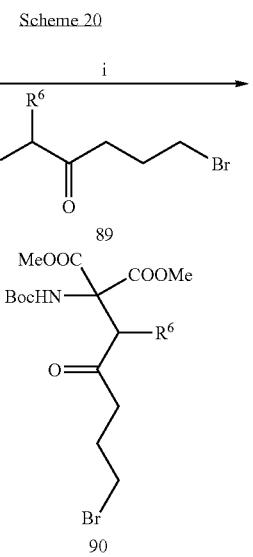

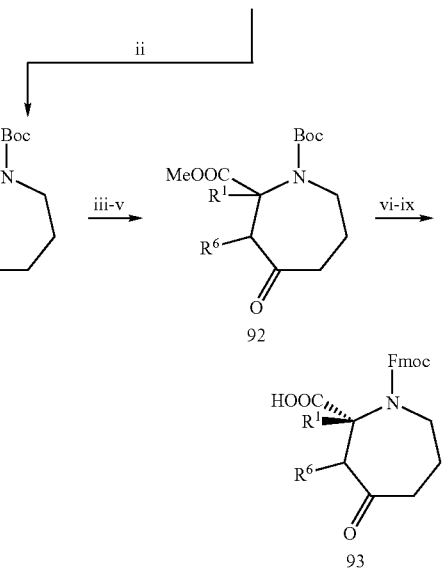

i: NaOMe, MeOH;
ii: NaH, THF;
iii: NaOH aq., MeOH, 75°; then HCl aq.;
iv: DBU, MeI, DMF;
v: lithium hexamethyldisilazide, THF, chlorotrimethylsilane, -78°; then R$^1$—X;
vi: resolution (e,.g. lipase); then isolation of methylester; DBU, MeI, DMF;
vii: Liohx1H$_2$O, MeOH, H$_2$O;
viii: TFA, CH$_2$Cl$_2$;
ix: FmocOSu, Na$_2$CO$_3$ aq., dioxane A58: See C. -H. Lee, H. Kohn, *J. Org. Chem.* 1990, 55, 6098-6104 (R$^1$=R$^8$=H).

A59: can be prepared according to Scheme 21.

Scheme 21

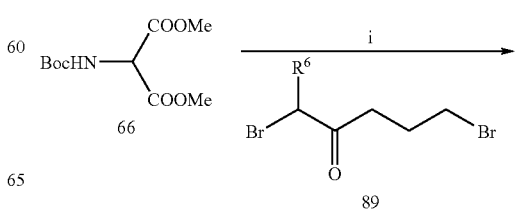

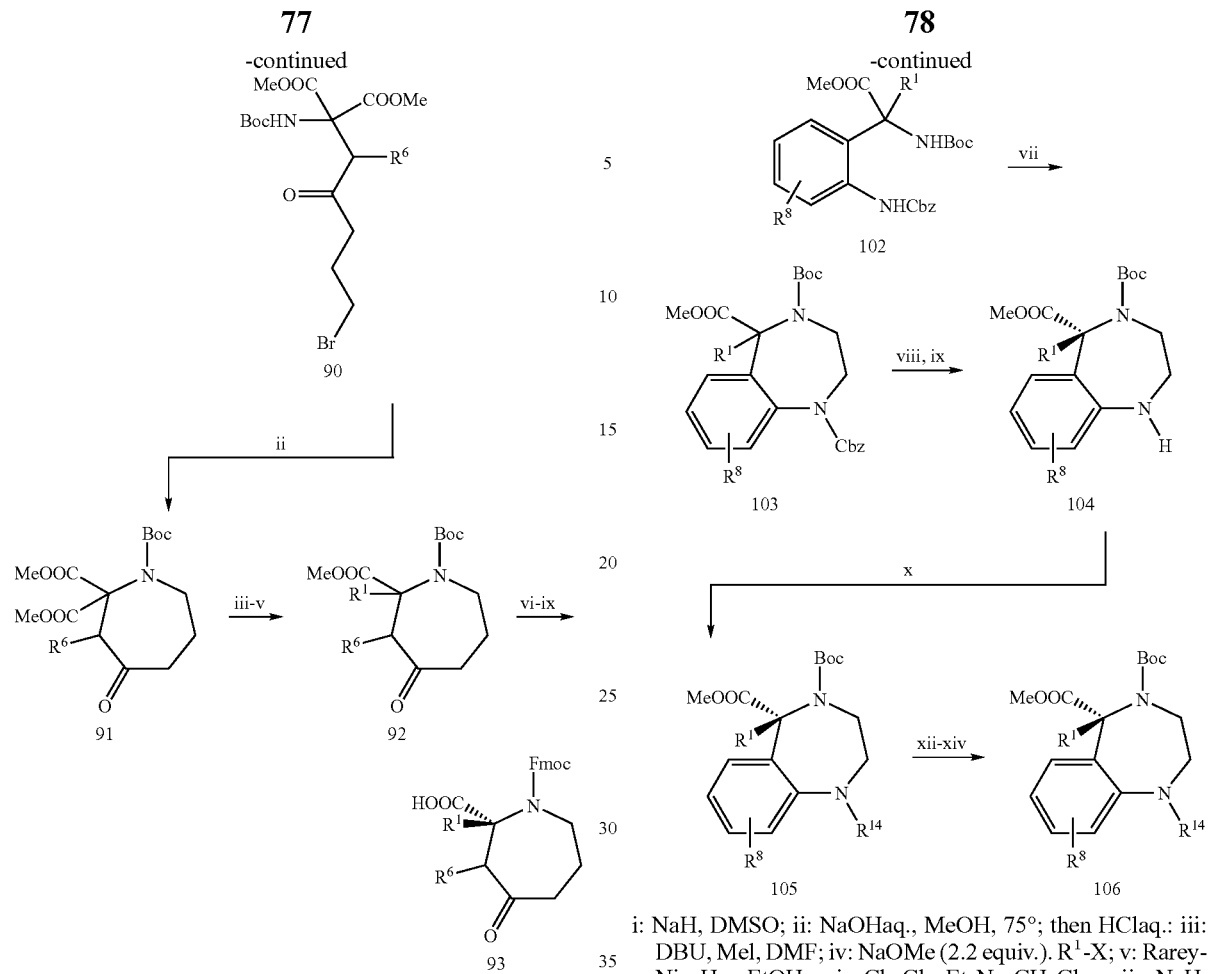

i: NaOMe, MeOH;
ii: NaH, THF;
iii: NaOH aq., MeOH, 75°; then HCl aq.;
iv: DBU, MeI, DMF;
v: lithium hexamethyldisilazide, THF, chlorotrimethylsilane, -78°; then R¹—X;
vi: resolution (e.g. lipase); then isolation of methylester; DBU, MeI, DMF;
vii: LiOHx1H₂O, MeOH, H₂O;
viii: TFA, CH₂Cl₂;
ix: FmocOSu, Na₂CO₃ aq., dioxane 0: Compounds of this type can be prepared according to Scheme 22.

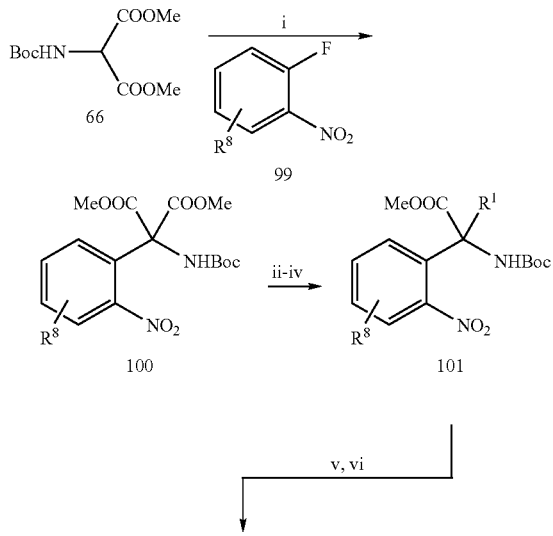

i: NaH, DMSO; ii: NaOHaq., MeOH, 75°; then HClaq.: iii: DBU, MeI, DMF; iv: NaOMe (2.2 equiv.). R¹-X; v: Rarey-Ni. H₂, EtOH; vi: CbzCl, Et₃N, CH₂Cl₂; vii: NaH, Br(CH₂)₂Br, THF; viii: resolution (e.g. lipase); then DBU, MeI, DMF; ix: Pd/C, H₂, EtOH; x: NaH, R¹⁴-X, THF: xi: LiOHx1H₂O, MeOH. H₂O: xii: TFA, CH₂Cl₂; xiii: FmocOSu, Na₂CO₃aq., dioxane A61: See D. R. Armour, K. M. Morriss, M. S. Congreve, A. B. Hawcock, *Bioorg. Med. Chem. Lett.* 1997, 7, 2037-2042 (R¹=R¹²=H).

A62: Compounds of this type can be prepared according to Scheme 23.

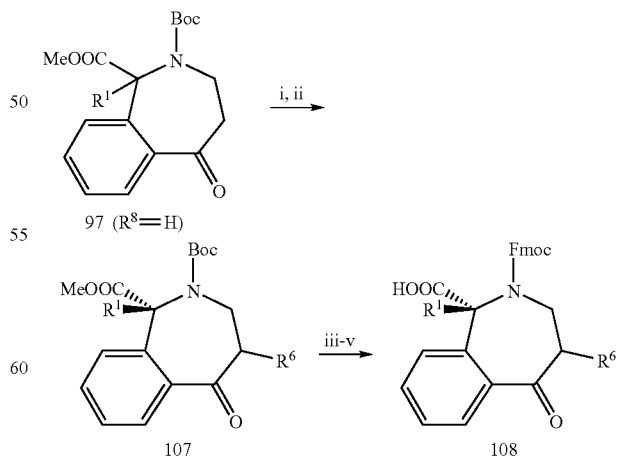

i: resolution (e.g. lipase); then DBU, MeI, DMF;
ii: lithium hexamethyldisilazide, THF, chlorotrimethylsilane, -78°; then R⁶—X;
iii: LiOHx1H₂O, MeOH, H₂O;
iv: TFA, CH₂Cl₂;
v: FmocOSu, Na₂CO₃ aq., dioxane A63: See S. E. Gibson, N. Guillo, R. J. Middleton, A. Thuilliez, M. J. Tozer, *J. Chem. Soc. Perkin Trans.* 1, 1997, 4, 447-456; S. E. Gibson, N. Guillo, S. B. Kalindjan, M. J. Tozer, *Bioorg. Med. Chem. Lett,.* 1997, 7, 1289-1292 ($R^1$=H; $R^8$=H); Beilstein Registry Number: 459155 ($R^1$=H; $R^8$=4, 5-$MeO_2$).

A64: Compounds of this type can be prepared according to Scheme 24.

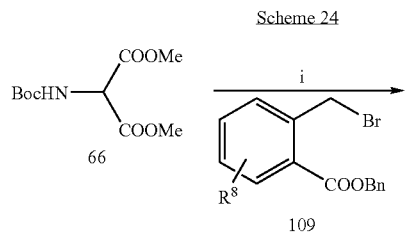

Scheme 24

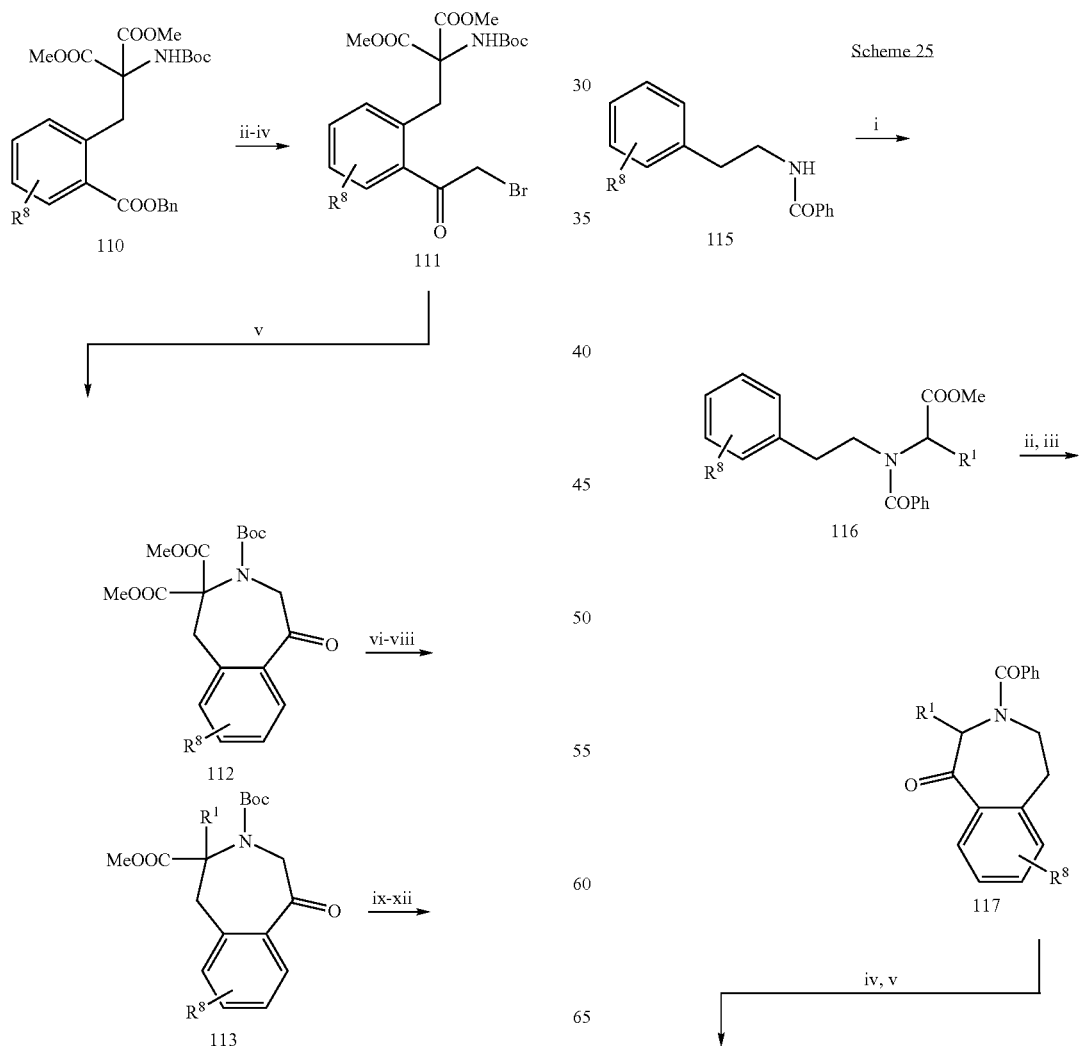

i: NaH, DMSO;
ii: Pd/C, $H_2$, EtOH;
iii: iBuOCOCl, diisopropylethylamine, $CH_2Cl_2$; then diazomethane;
iv: HBr, $CH_2Cl_2$;
v: NaH, THF;
vi: NaOH aq., MeOH, 75°; then HCl aq.;
vii: DBU, MeI, DMF;
viii: lithium diisopropylamide, THF, chlorotrimmethylsilane, -78°; then $R^1$—X;
ix: resolution (e.g. lipase); then isolation of methylester: DBU, MeI, DMF;
x: LiOHx1$H_2$O, MeOH, $H_2$O;
xi: TFA, $CH_2Cl_2$;
xii: FmocOSu, $Na_2CO_3$ aq.. dioxane A65 and A 67: Compounds of these types can be prepared according to Schemes 25 and 26.

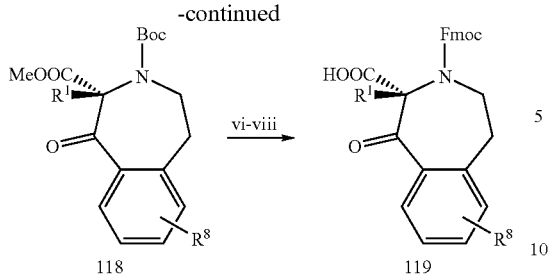

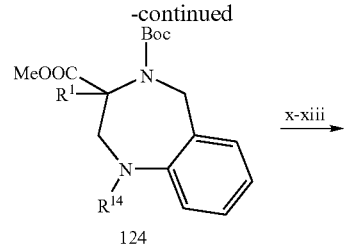

i: NaH, DMSO, BrCH(R¹)COOMe;
ii: LiOHx1H₂O, MeOH, H₂O;
iii: polyphosphoric acid;
iv: NaH, ClCOOMe, THF;
v: resolution (e.g. lipase); then isolation as methylester, DBU, MeI, DMF;
vi: LiOHx1H₂O, MeOH, H₂O;
vii: TFA, CH₂Cl₂;
viii: FmocOSu, Na₂CO₃ aq., dioxane Scheme 26

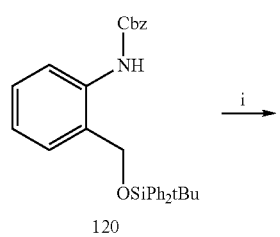

i: NaH, THF, CH₂I₂;
ii: NaH, DMSO;
iii: Bu₄NFx10H₂O, THF;
iv: methanesulfonylchloride, Et₃N, CH₂Cl₂; then NaH, THF;
v: NaOH aq., MeOH, 75°; then HCl aq.;
vi: DBU, MeI DMF;
vii: lithium hexamethyldisilazide, THF, chlorotrimethylsilane, -78°; then R¹—X;
viii: Pd/D, H₂, EtOH;
ix: NaH, THF, R¹⁴—X;
x: resolution (e.g. lipase); then isolation of methylester: DBU, MeI, DMF;
xi: LiOHx1H₂O, MeOH, H₂O;
xii: TFA, CH₂Cl₂;
xiii: FmocOSu, Na₂CO₃ aq., dioxane

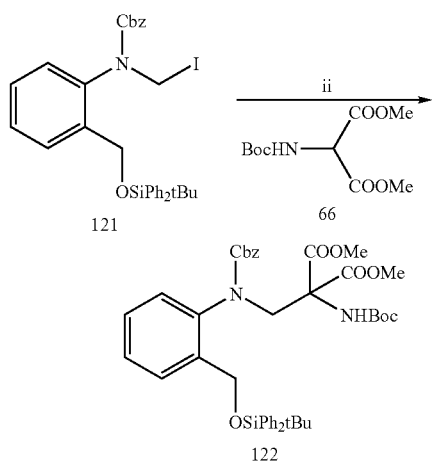

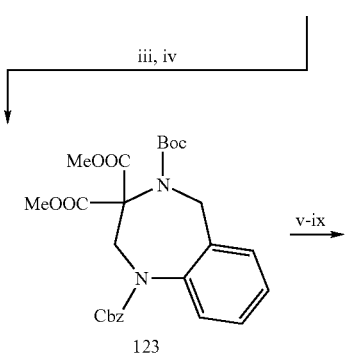

A66: See G. L. Grunewald, L. H. Dahanukar, *J. Heterocycl. Chem.* 1994, 31, 1609-1618 ($R^1$=H; $R^8$=K, 8-NO₂; C(1)=O).

A68: See Griesbeck, H. Mauder, I. Müller, *Chem. Ber.* 1992, 11, 2467-2476; ($R^1$=$R^8$=H; C(1)=O).

A69: R. Kreher, W. Gerhardt, *Liebigs Ann. Chem.* 1981, 240-247 ($R^1$=$R^8$=H).

As explained above, building blocks A70 belong to the class of open-chain α-substituted α-amino acids, A71 and A72 to the class of the the corresponding β-amino acid analogues and A73—A104 to the class of the cyclic analogues of A70.

Building blocks of types A70 and A73—A104 have been synthesized by several different general methods: by [2+2] cycloaddition of ketenes with imines (I. Ojima, H. J. C. Chen, X. Quin, *Tetrahedron Lett.* 1988, 44, 5307-5318); by asymmetric aldol reaction (Y. Ito, M. Sawamura, E. Shirakawa, K. Hayashikazi, T. Hayashi, *Tetrahedron Lett.* 1988, 29, 235-238; by the oxazolidinone method (J. S. Amato, L. M. Weinstock, S. Karady, U.S. Pat. No. 4,508,921 A; M. Gander-Coquoz, D. Seebach, *Helv. Chim. Acta* 1988, 71, 224-236; A. K. Beck, D. Seebach, *Chimia* 1988, 42, 142-144; D. Seebach, J. D. Aebi, M. Gander-Coquoz, R. Naef, *Helv. Chim. Acta* 1987, 70, 1194-1216; D. Seebach, A. Fadel, *Helv. Chim. Acta* 1995, 68, 1243-1250; J. D. Aebi, D. Seebach, *Helv. Chim. Acta* 1985, 68, 1507-1518; A. Fadel, J. Salaun, *Tetrahedron Lett.* 1987, 28, 2243-2246); by Schmidt-rearrangement of α,α-disubstituted α-ketoesters (G. L. Georg, X. Guan, J.

Kant, *Tetrahedron Lett.* 1988, 29, 403-406); asymmetric synthesis via chiral Ni(II)-derived Schiff-bases (Y. N. Belokon, V. L Bakhmutov, N. I. Chemoglazova, K. A Kochetov, S. V. Vitt, N. S. Garbalinskaya, V. M. Belikov, *J. Chem. Soc. Perkin Trans.* 1, 1988, 305-312; M. Korb, J. Barth, *Liebigs Ann. Chem.* 1983, 1668-1688); by the bis-lactim ether synthesis (U. Schöllkopf, R. Hinrichs, R. Lonsky, *Angew. Chem* 1987, 99, 137-138); by microbial resolution (K. Sakashita, I. Watanabe, JP 62/253397 A2) and by the hydantoin method combined with resolution of the racemic amino acids with chiral auxilliaries derived from L-phenylalanine amides (D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714; D. Obrecht, M. Altorfer, C. Lehmann, P. Schönholzer, K. Müller, *J. Org. Chem.* 1996, 61, 4080-4086; D. Obrecht, C. Abrecht, M. Altorfer, U. Bohdal, A. Grieder, P. Pfyffer, K. Müller, *Helv. Chim. Acta* 1996, 79, 1315-1337). The latter method has been especially useful in preparing both enantiomers of building blocks of type A70 (see Scheme 27) and A73—A104 (see Scheme 28) in pure form.

Scheme 27

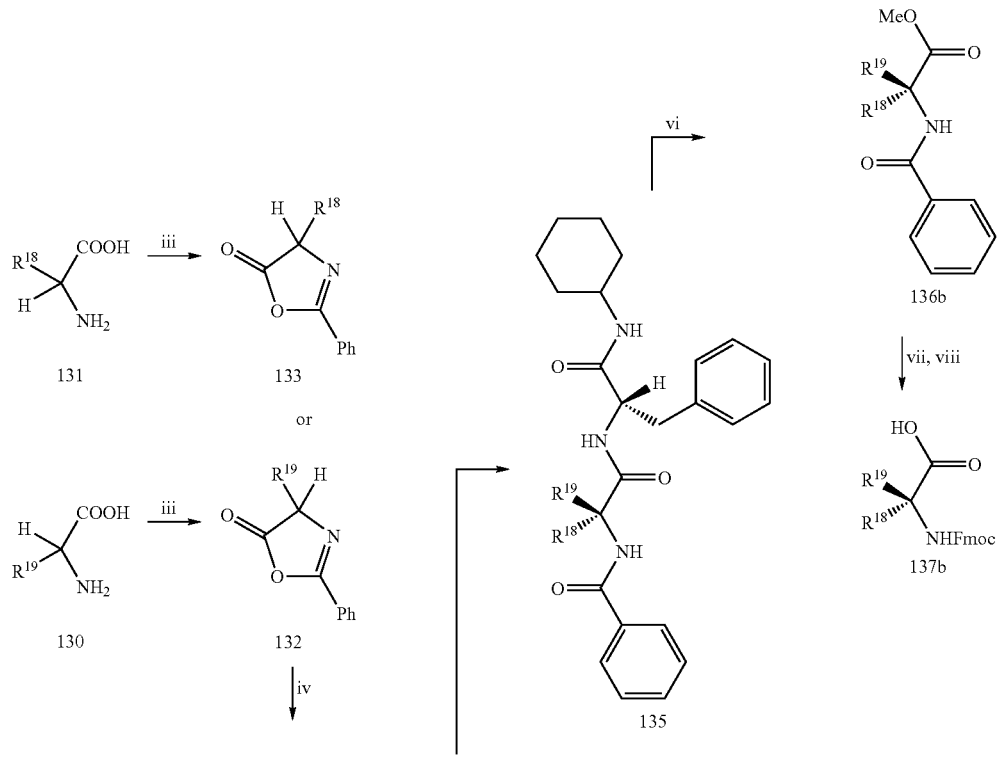

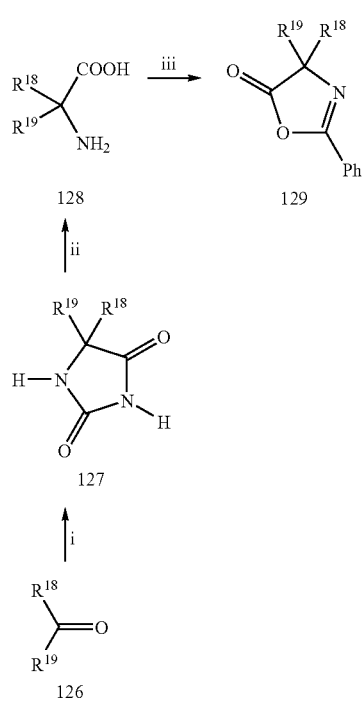
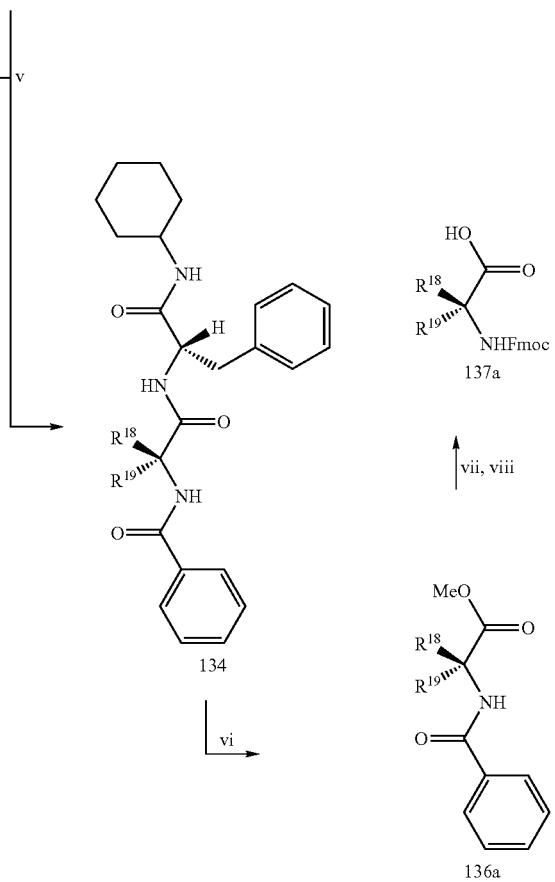

i: KCN, (NH$_4$)$_2$CO$_3$, EtOH/H$_2$O;
ii: Ba(OH)$_2$, H$_2$O;
iii: aq. NaOH, PhCOCl, dioxane; then DCC, CH$_2$Cl$_2$;
iv: NaH, DMF, R$^{18}$—X or R$^{19}$—X;
v: L-phenylalanine cyclohexylamide. N-methylpyrrolidone, 70°;
vi: CH$_3$SO$_3$H, MeOH, 80°;
vii: 6N HCl aq., dioxane, 100°;
viii: Me$_3$SiCl, DIEA, CH$_2$Cl$_2$; then FmocCl The method depicted in Scheme 27 consists in treatment of the appropriate ketones 126 with KCN, (NH$_4$)$_2$CO$_3$ in a mixture of ethanol/water (E. Ware, *J. Chem. Res.* 1950, 46, 403; L. H. Goodson, I. L. Honigberg, J. J. Lehmann, W. H. Burton, *J. Org. Chem.* 1960, 25, 1920; S. N. Rastogi, J. S. Bindra, N. Anand, *Ind. J. Chem.* 1971, 1175) to yield the corresponding hydantoins 127, which were hydrolyzed with Ba(OH)$_2$ in water at 120-140° (R. Sarges, R. C. Schur, J. L. Belletire, M. J. Paterson, *J. Med. Chem.* 1988, 31, 230) to give 128 in high yields. Schotten-Baumann acylation (Houben-Weyl, 'Methoden der Organischen Chemie', Volume XI/2, Stickstoff-Verbindungen II und III', Georg Tieme Verlag, Stuttgart, pp 339) followed by cyclization with N,N'-dicyclohexyl carbodiimide gave azlactones 129 (D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696). Alternatively, azlactones 129 could also be prepared staring from amino acids 130 and 131, Schotten-Baumann acylation and cyclization with N,N'-dicyclohexyl carbodiimide to azlactones 132 and 133 and alkylation to yield 129 (D. Obrecht, U. Bohdal, C. Broger, D. Bur, C. Lehmann, P Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696)(see Scheme 1). Treatment of 129 with L-phenylalanine cyclohexylamide (D. Obrecht, U. Bohdal, C. Broger, D. Bur, C. Lehmann, R. Ruffieux, P. Schönholzer, C. Spiegler, *Helv. Chim. Acta* 1995, 78, 563-580) gave diastereomeric peptides 134 and 135, which could be conveniently separated by flash-chromatography or crystallisation. Treatment of 134 and 135 with methanesulphonic acid in methanol at 80° gave esters 136a and 136b which were converted into the corresponding Fmoc-protected final building blocks 137a and 137b.

Scheme 28
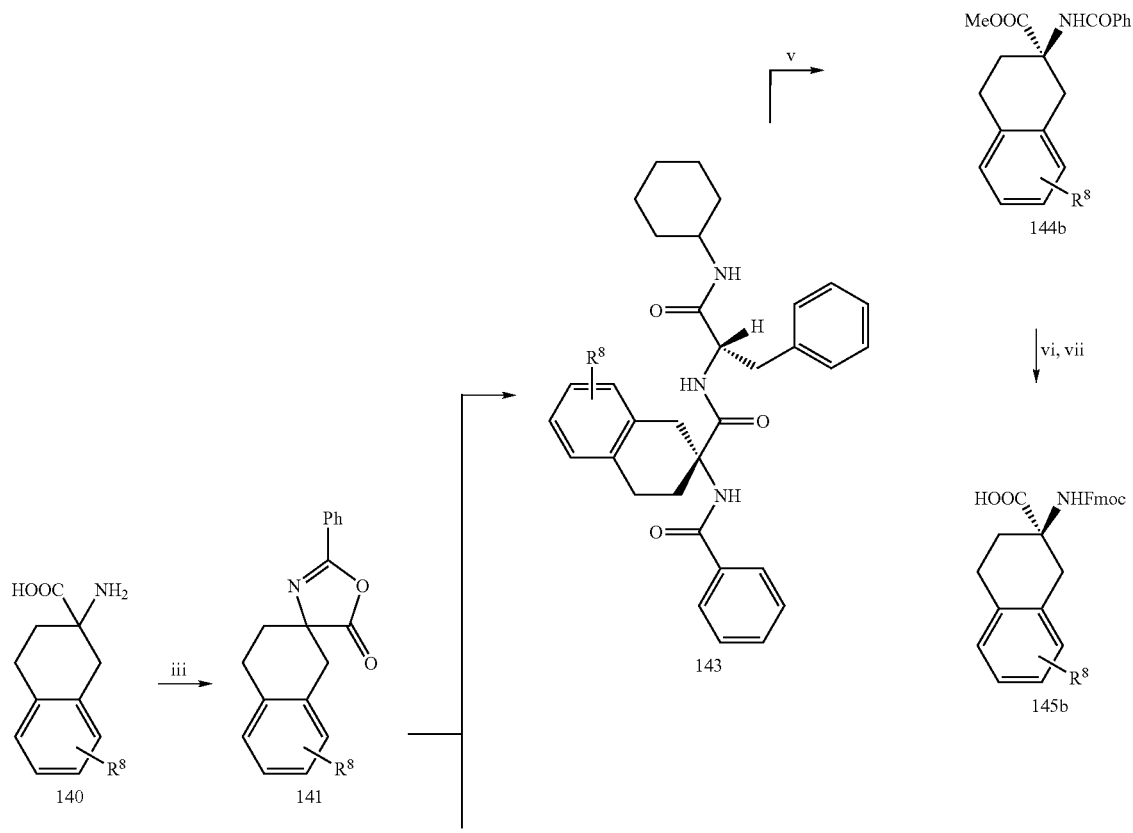

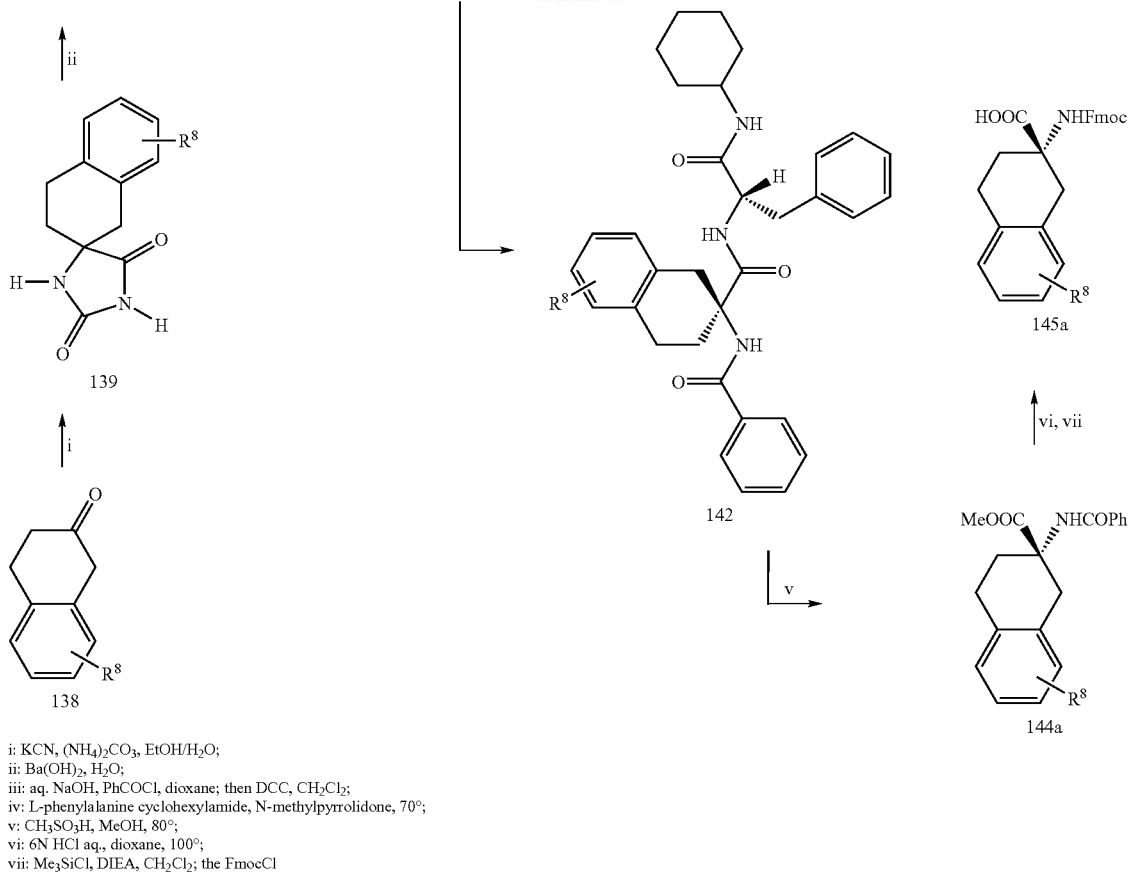

i: KCN, (NH₄)₂CO₃, EtOH/H₂O;
ii: Ba(OH)₂, H₂O;
iii: aq. NaOH, PhCOCl, dioxane; then DCC, CH₂Cl₂;
iv: L-phenylalanine cyclohexylamide, N-methylpyrrolidone, 70°;
v: CH₃SO₃H, MeOH, 80°;
vi: 6N HCl aq., dioxane, 100°;
vii: Me₃SiCl, DIEA, CH₂Cl₂; the FmocCl According to the general method described in Scheme 28 (D. Obrecht, U. Bohdal, C. Broger, D. Bur, C. Lehmann, R. Ruffieux, P. Schönholzer, C. Spiegler, *Helv. Chim. Acia* 1995, 78, 563-580; D. Obrecht, C. Spiegler, P. Schönholzer, K. Müller, H. Heimgartner, F. Stierli, *Helv. Chim. Acta* 1992, 75, 1666-1696) A73—A104 can be prepared starting from the corresponding ketones 138, hydantoin formation (139) (E. Ware, *J. Chem. Res.* 1950, 46, 403; L. H. Goodson, I. L. Honigberg, J. J. Lehmann, W. H. Burton, *J. Org. Chem.* 1960, 25, 1920; S. N. Rastogi, J. S. Bindra, N. Anand, *Ind J. Chem.* 1971, 1175; D. Obrecht, U. Bohdal, C. Broger, D. Bur, C. Lehmann, R. Ruffieux, P. Schönholzer, C. Spiegler, *Helv. Chim. Acta* 1995, 78, 563-580) and saponification (Ba(OH)₂) to yield the racemic amino acids 140, which upon Schotten-Baumann-acylation and cyclization with N,N'-dicyclohexyl-carbodiimide gave azlactones 141. Reaction with L-phenylalanine cyclohexylamide (D. Obrecht, U. Bohdal, C. Broger, D. Bur, C. Lehmann, R. Ruffieux, P. Schönholzer, C. Spiegler, *Helv. Chim. Acta* 1995, 78, 563-580) gave the diastereomeric peptides 142 and 143, which were separated by flash-chromatography or crystallization. Treatment of 142 and 143 with methanesulphonic acid in methanol at 80° gave esters 144a and 144b which were converted into the corresponding suitably protected amino acid precursors 145a and 145b, ready for peptide synthesis.

A71: Amino acid building blocks of this type (see formula 147) can be conveniently prepared from the corresponding disubstituted succinates 146 by Curtius-rearrangement as shown in Scheme 29.

Scheme 29

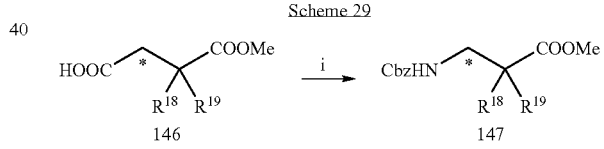

i: diphenylphosphoryl azide, toluene, 80°; then benzyl alcohol

A71: See D. Seebach, S. Abele. T. Sifferlen, M. Haenggi, S. Gruner, P. Seiler, *Helv. Chim. Acta* 1998, 81, 2218-2243 ($R^{18}$ and $R^{19}$ form: —(CH₂)₂—; —(CH₂)₃—; —(CH₂)₄—; —(CH₂)₅; $R^{20}$=H); L. Ducrie, S. Reinelt, P. Seiler, F. Diederich, D. R. Bolin, R. M. Campbell, G. L. Olson, *Helv. Chim. Acta* 1999, 82, 2432-2447; C. N. C. Drey, R. J. Ridge, *J. Chem. Soc. Perkin Trans.* 1, 1981, 2468-2471; U. P. Dhokte, V. V. Khau, D. R. Hutchinson, M. J. Martinelli, *Tetrahedron Lett.* 1998, 39, 8771-8774 ($R^{18}$=$R^{19}$=Me; $R^{20}$=H); D. L. Varie, D. A. Hay, S. L. Andis, T. H. Corbett, *Bioorg. Med. Chem. Lett.* 1999, 9, 369-374 ($R^{18}$=$R^{19}$=Et); Testa, *J. Org. Chem.* 1959, 24, 1928-1936 ($R^{18}$=Et; $R^{19}$=Ph); M. Haddad, C. Wakselman, *J. Fluorine Chem.* 1995, 73, 57-60 ($R^{18}$=Me; $R^{19}$=CF₃; $R^{20}$=H); T. Shono, K. Tsubata, N. Okinaga, *J. Org. Chem.* 1984, 49, 1056-1059 ($R^{18}$=$R^{19}$=$R^{20}$=Me); K. Ikeda, Y. Terao, M. Sekiya, *Chem. Pharm. Bull.* 1981, 29, 1747-1749 ($R^{18}$ and $R^{19}$ form: —(CH₂)₅—; $R^{20}$=Me).

Amino acid building blocks of type A72 can be conveniently prepared by Arndt-Eistert C1-homologation of compounds of type A70 according to Scheme 30.

Scheme 30

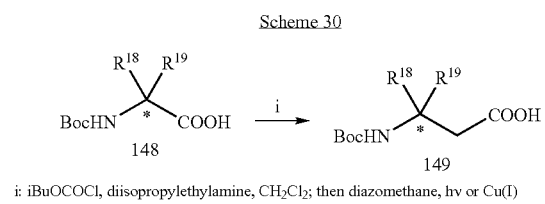

i: iBuOCOCl, diisopropylethylamine, CH$_2$Cl$_2$; then diazomethane, hv or Cu(I)

A72: See Y. V. Zeifman, *J. Gen. Chem. USSR* (Engl. Trans.) 1967, 37, 2355-2363 (R$^{18}$=R$^{19}$=CF$_3$); W. R. Schoen, J. M. Pisano, K. Pendergast, M. J. Wyvratt, M. H. Fisher, *J. Med. Chem.* 1994, 37, 897-906; S. Thaisrivongs, D. T. Pals, D. W. DuCharme, S. Turner, G. L. DeGraaf, *J. Med. Chem.* 1991, 34, 655-642; T. K. Hansen, H. Thoegersen, B. S. Hansen, *Bioorg. Med. Chem. Lett.* 1997, 7, 2951-2954; R. J. DeVita, R. Bochis, A. J. Frontier, A. Kotliar, M. H. Fisher, *J. Med. Chem.* 1998, 41, 1716-1728; D. Seebach, P. E. Ciceri, M. Overhand, B. Jaun, D. Rigo, *Helv. Chim. Acta* 1996, 79, 2043-2066; R. P. Nargund, K. H. Barakat, K. Cheng, W. Chan, B. R. Butler, A. A. Patchett, *Bioorg. Med. Chem. Lett.* 1996, 6, 1265-1270 (R$^{18}$=R$^{19}$=Me); F. Altmann, K. Nebel, M. Mutter, *Helv. Chim. Acta* 1991, 74, 800-806 (R$^{18}$=Me; R$^{19}$=COOMe).

A73: Compounds of this type can be prepared according to C. Mapelli, G. Tarocy, F. Schwitzer, C. H. Stammer, *J. Org. Chem.* 1989, 54, 145-149 (R$^{21}$=4-OHC$_6$H$_4$); F. Elrod, E. M. Holt, C. Mapelli, C. H. Stammer, *J. Chem. Soc Chem. Commun.* 1988, 252-253 (R$^{21}$=CH$_2$COOMe); R. E. Mitchell, M. C. Pirrung, G. M. McGeehan, *Phytochemistry* 1987, 26, 2695 (R$^{21}$=CH$_2$OH), J. Bland, A. Batolussi, C. H. Stammer, *J. Org. Chem.* 1988, 53, 992-995 (R$^{21}$=CH$_2$NH$_2$). Additional derivatives of A73 have been described by T. Wakamiya, Y. Oda, H. Fujita, T. Shiba, *Tetrahedron Lett.* 1986, 27, 2143-2134; U. Schöllkopf, B. Hupfeld, R. Gull, *Angew. Chem.* 1986, 98, 755-756; J. E. Baldwin, R. M. Adlington, B. J. Rawlings, *Tetrahedron Lett.* 1985, 26, 481-484; D. Kalvin, K. Ramalinggam, P. Woodard, *Synth. Comm.* 1985, 15, 267-272 and L. M. Izquierdo, I. Arenal, M. Bernabe, E. Alvarez, *Tetrahedron Lett.* 1985, 41, 215-220.

A74: Compounds of this type can be prepared according to general method described in Scheme 28 staring from the corresponding cyclobutanones.

A75 and A76: Compounds of this type can be prepared using the following methods: P. Hughes, J. Clardy, *J. Org. Chem.* 1988, 53, 4793-4796; E. A Bell, M. Y. Qureshi, R. J. Pryce, D. H. Janzen, P. Lemke, J. Clardy, *J. Am. Chem. Soc.* 1980, 102, 1409; Y. Gaoni, *Tetrahedron Lett.* 1988, 29, 1591-1594; R. D. Allan, J. R. Haurahan, T. W. Hambley, G. A. R. Johnston, K. N. Mewett, A. D. Mitrovic, *J. Med. Chem.* 1990, 33, 2905-2915 (R$^{23}$=COOH); G. W. Fleet, J. A. Seijas, M. Vasquez Tato, *Tetrahedron* 1988, 44, 2077-2080 (R$^{23}$=CH$_2$OH).

A77: Compounds of this type can be prepared according to J. H. Burckhalter, G. Schmied, *J. Pharm. Sci.* 1966, 55, 443-445 (R$^{23}$=aryl).

A78: Compounds of this type can be prepared according to J. C. Watkins, P. Kroosgard-Larsen, T. Honoré, *TIPS* 1990, 11, 25-33; F. Trigalo, D. Brisson, R. Azerad, *Tetrahedron Lett.* 1988, 29, 6109 (R$^{24}$=COOH).

A79: Compounds of this type can be prepared according to general method described in Scheme 28 starting from the corresponding pyrrolidine-3-ones.

A80—A82: Compounds of this type can be prepared according to D. M. Walker, E. W. Logusch, *Tetrahedron Lett.* 1989, 30, 1181-1184; Y. Morimoto, K. Achiwa, *Chem. Pharm. Bull.* 1989, 35, 3845-3849; J. Yoshimura, S. Kondo, M. Ihara, H. Hashimoto, *Carbohydrate Res.* 1982, 99, 129-142.

A83: Compounds of this type can be prepared according to general method described in Scheme 28 starting from the corresponding pyrazoline-4-ones.

A84: Compounds of this type can be prepared according to R. M. Pinder, B. H. Butcher, D. H. Buxton, D. J. Howells, *J. Med Chem.* 1971, 14, 892-893; D. Obrecht, U. Bohdal, C. Broger, D. Bur, C. Lehann, R. Ruffieux, P. Schönholzer, C. Spiegler, *Helv. Chim. Acta* 1995, 78,563-580.

A85: Compounds of this type can be prepared according to general method described in Scheme 28 starting from the corresponding indane-1,3-diones.

A86: Compounds of this type can be prepared according to general method described in Scheme 28 starting from the corresponding indane-2-ones.

A87: Compounds of this type and analogues thereof can be prepared according to C. Cativiela, M. D. Diaz de Villegas, A. Avenoza, J. M. Peregrina, *Tetrahedron* 1993, 47, 10987-10996; C. Cativiela, P. Lope, J. A. Mayoral, *Tetrahedron Assymmetry* 1990, 1, 379; C. Cativiela, J. A. Mayoral, A. Avenoza, M. Gonzalez, M. A Rey, *Synthesis* 1990, 1114.

A87 and A88: Compounds of this type can be prepared according to L. Munday, *J. Chem. Soc.* 1961, 4372; J. Ansell, D. Morgan, H. C. Price, *Tetrahedron Lett.* 1978, 47, 4615-4616.

A89: Compounds of this type can be prepared according to general method described in Scheme 28 starting from the corresponding piperidine-3-ones.

A90: Compounds of this type can be prepared according to general method described in Scheme 28 starting from the corresponding tetrahydrothiapyran-3-ones.

A91: Compounds of this type can be prepared according to general method described in Scheme 28 starting from the corresponding tetrahydropyran-3-ones.

A92: Compounds of this type can be prepared according to general method described in Scheme 28 starting from the corresponding piperidine-2,5-diones.

A93: Compounds of this type can be prepared according to general method described in Scheme 28 starting from the corresponding cyclohexanones.

A94: Compounds of this type can be prepared according to *J. Org. Chem.* 1990, 55, 4208.

A95: Compounds of this type can be prepared according to N. J. Lewis, R. L. Inloes, J. Hes, R. H. Matthews, G. Milo, *J. Med. Chem.* 1978, 21, 1070-1073.

A96: Compounds of this type can be prepared according to general method described in Scheme 28 starting from the corresponding tetrahydropyran-4-ones.

A97: Compounds of this type can be prepared according to general method described in Scheme 28 starting from the corresponding piperidine-2,4-diones.

A98: Compounds of this type can be prepared according to general method described in Scheme 28 starting from the corresponding 1-tetralones (D. Obrecht, C. Spiegler, P. Schönholzer, K. Müller, H. Heimgartner, F. Stierli, *Helv. Chim. Acta* 1992, 75, 1666-1696).

A99: Compounds of this type can be prepared according to general method described in Scheme 28 starting from the corresponding tetraline-1,4-dione monodiethylacetals.

A100: Compounds of this type can be prepared according to general method described in Scheme 28 starting from the corresponding tetrahydroquinolin-4-ones.

A101: Compounds of this type can be prepared according to general method described in Scheme 28 starting from the corresponding tetrahydroquinoline-2,4-diones.

A102: Compounds of this type can be prepared according to K. Ishizumi, N. Ohashi, N. Tanno, *J. Org. Chem.* 1987, 52, 4477-4485; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696; D. R. Raines, R. W. Fuller, S. Ahmad, D. T. Vistica, V. E. Marquez, *J. Med. Chem.* 1987, 30, 542-547; T. Decks, P. A. Crooks, R. D. Waigh, *J. Pharm. Sci* 1984, 73, 457-460; I. A. Blair, L. N. Mander, *Austr. J. Chem.* 1979, 32, 1055-1065.

Overviews dealing with building blocks of types (b)-(p) are: S. Hanessian, G. McNaughton-Smith, H. -G. Lombart, W. D. Lubell, *Tetrahedron* 1997, 38, 12789-12854; D. Obrecht, M. Altorfer, J. A. Robinson, "Novel Peptide Mimetic Building Blocks and Strategies for Efficient Lead Finding", *Adv. Med. Chem.* 1999, Vol. 4, 1-68.

Templates of type (b1) can be prepared according to Schemes 31 and 32.

Scheme 31

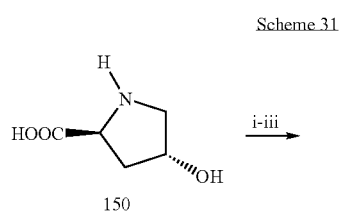

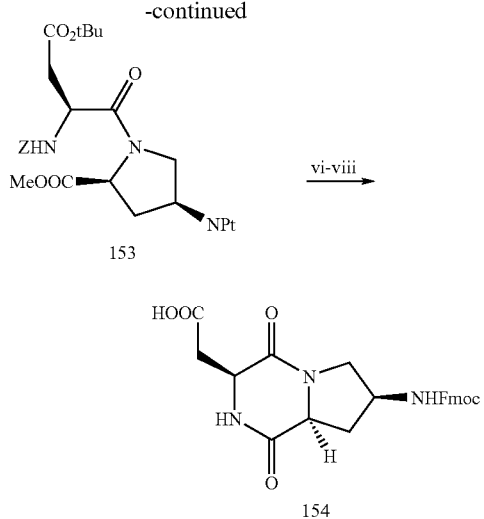

i: Treatment of 150 with a dehydrating reagent such as thionylchloride in methanol at an elevated temperature, conveniently at reflux.

ii: Introduction of Boc, e.g. using di-tert.-butyl dicarbonate and triethylamine in a suitable solvent such as dichloromethane; any other suitable N-protecting group (not shown in Reaction Scheme 31) can be introduced in an analogous manner.

iii: Reaction of formed product with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672) to conveniently yield 151.

iv: Treatment of 151 with trifluoracetic acid in dichloromethane.

v: 152 is coupled under standard peptide coupling conditions with Cbz-Asp(tBu)OH in DMF with reagents such as HBTU and 1-hydroxybenztriazole (HOBt) with a base such as diisopropylethylamine to yield 153.

vi: Removal of the Cbz-group, conveniently by hydrogenation using $H_2$ and a catalyst such as Palladium on charcoal, in solvents such as ethanol, DMF and ethyl acetate.

vii: The phthalimide group is cleaved off from the resulting product, conveniently by treatment with hydrazine in a suitable solvent such as ethanol at an elevated temperature, suitably at about 80° C. and cleavage of the formed product with trifluoracetic acid in $CH_2Cl_2$.

viii: The formed amino acid is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 154 as described by Bisang, C.; Weber, C.; Robinson, J. A. *Helv. Chim. Acta* 1996, 79, 1825-1842.

Scheme 32

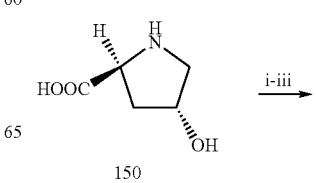

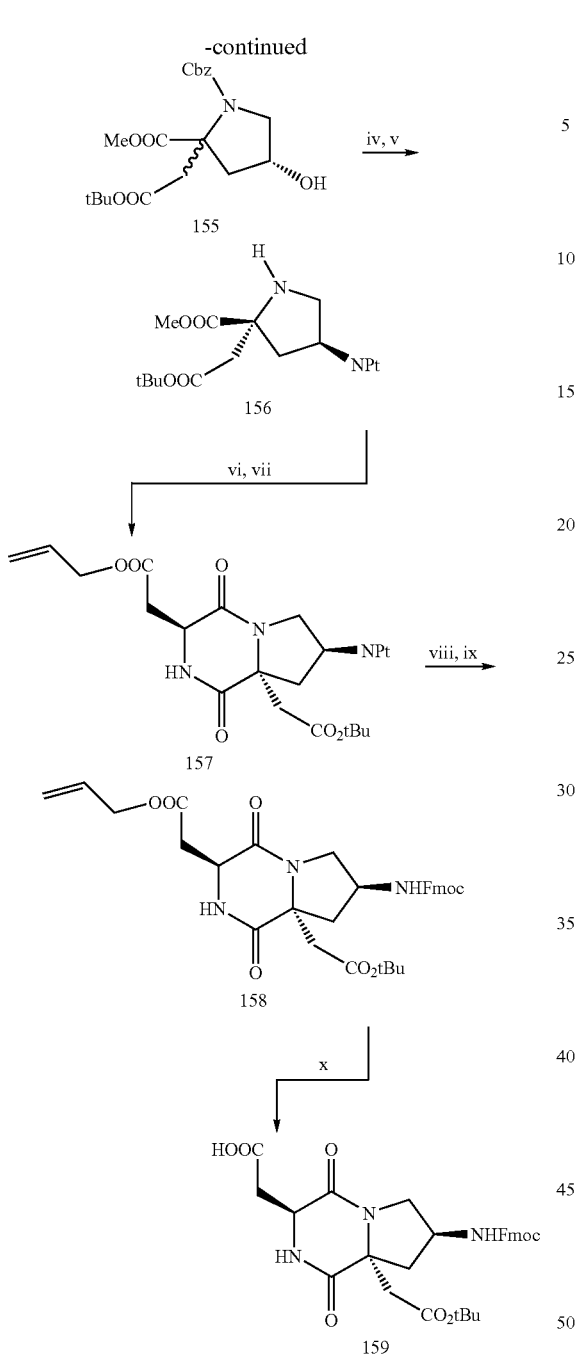

Freund, E.; Emery, F.; Bauch, C.; Matile, H,; Pluschke, G.; Robinson, J. A. *J. Am. Chem. Soc.* 1998, 120, 7439-7449; Emery, F.; Bisang, C.; Favre, M.; Jiang, L.; Robinson, J. A. *J. Chem. Soc. Chem. Commun.* 1996, 2155-2156.

iv: Reaction of 155 with phthalimide, diethyl diazodicarboxylate and triphenylphosphine under standard Mitsunobu conditions (Mitsunobu, O.; Wada, M.; Sano, T. J. *J. Am. Chem. Soc.* 1972, 94, 672).

v: The resulting product is hydrogenated using $H_2$ and a suitable catalyst such as palladium on charcoal in a solvent such as ethyl acetate, DMF or ethanol; subsequently separation of diastereomers takes place and yields 156.

vi: 156 is coupled with Fmoc-Asp(allyl)OH under standard peptide coupling conditions using reagents such as HATU, HOAt and a base such as diisopropylethylamine in a suitable solvent such as DMF.

vii: Cyclization, conveniently with DBU in DMF to yield 157.

viii: The phthalimide group is cleaved off from resulting product, conveniently by hydrazinolysis, e.g. treatment with methylhydrazine in a suitable solvent such as DMF.

ix: The formed product is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 158.

x: Standard removal of an allyl ester group using e.g. palladium(0) as catalyst gives 159.

Templates of type (b2) can be prepared according to Scheme 33.

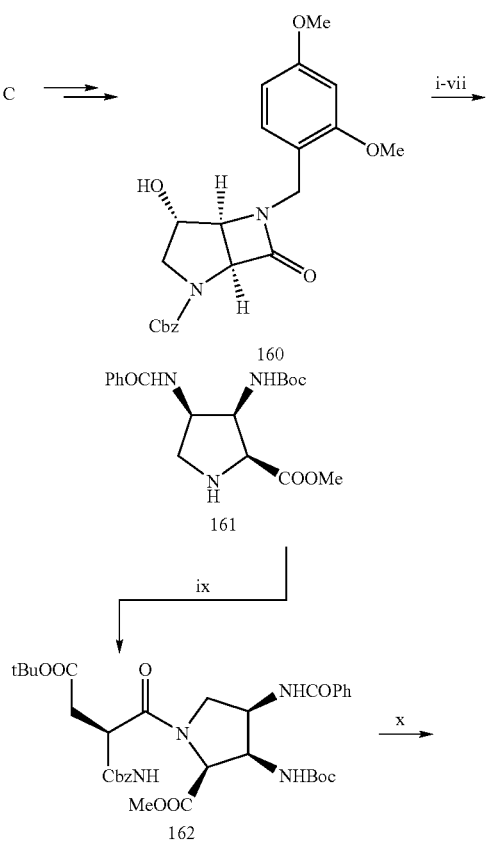

i: Treatment of 150 with a dehydrating reagent such as thionyl chloride in a suitable solvent such as methanol at an elevated temperature, conveniently at reflux.

ii: The resulting amino acid ester is N-protected under standard conditions for introducing the Cbz-group, e.g. using benzyloxycarbonyl chloride and triethylamine in a suitable solvent such as dichloromethane.

iii: The Cbz-protected amino acid methyl ester is treated with trimethylsilylchloride and a base such as triethylamine in a solvent such as tetrahydrofuran, cooled, conveniently to about −78° C., followed by reaction with a strong base such as lithium diisopropylamide or lithium hexamethyldisilylazide and tert.-butyl bromoacetate yielding 155 as a mixture of diastereomers as described by Bisang, C.; Jiang, L.;

-continued

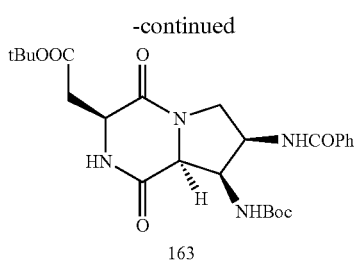

163 xi, xii

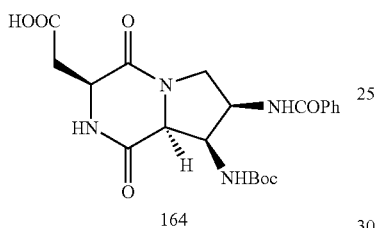

164 i: 160 (obtainable from Vitamin C as described by Hubschwerlen, C. (*Synthesis* 1986, 962) is treated with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672).

ii: The phthalimide group is cleaved off from the product, conveniently by hydrazinolysis, e.g. by treatment with methylhydrazine in a suitable solvent such as DMF.

iii: The amino group is protected by treatment with a benzoylating reagent such as benzoic acid anhydride or benzoylchloride and a base such as triethylamine or 4-dimethylaminopyridine in a suitable solvent such as dichloromethane or DMF.

iv: Removal of the 2,4-dimethoxybenzyl group, e.g. with $K_2S_2O_8$ and $Na_2HPO_4$ in aqueous acetonitrile at an elevated temperature, e.g. at about 80° C.

v: Introduction of a tert.-butoxycarbonyl group using e.g. di-tert-butyloxycarbonyl dicarbonate, triethylamine and a catalytic amount of 4-dimethylaminopyridine in a suitable solvent such as dichloromethane.

vi: Reaction with aqueous sodium carbonate in tetrahydrofuran followed by acidification.

vii: Esterification of the carboxylic acid group, conveniently with diazomethane in a suitable solvent such as diethylether yielding 161.

viii Removal of the Cbz-group, conveniently by hydrogenation with $H_2$ in the presence of a catalyst such as palladium on charcoal in a solvent such as DMF to yield 161 as described by Pfeifer, M.; Robinson, J. A. *J. Chem. Soc. Chem. Commun.* 1998, 1977.

ix: 161 is coupled under standard peptide coupling conditions with Cbz-Asp(tBu)OH in DMF with reagents such as HBTU and 1-hydroxybenztriazole with a base such as diisopropylethylamine to yield 162 as described by Pfeifer, M; Robinson, J. A. *J. Chem. Soc. Chem. Commun.* 1998, 1977.

x: Removal of the Cbz-group, e.g. by hydrogenation using $H_2$ and a catalyst such as palladium on charcoal under standard conditions, yields 163 as described by Pfeifer, M.; Robinson, J. A. *J. Chem. Soc. Chem. Commun.* 1998, 1977.

xi: Cleavage of the tert.-butyl ester and tert-butyloxycarbonyl groups, conveniently using trifluoracetic acid in dichloromethane or 4N hydrochloric acid in dioxane.

xii: The intermediate free amino acid formed is conveniently protected with reagents such as 9-fluorenylmethoxcarbonyl chloride or 9-fluorenylmethoxycarbonyl succinimide using a base such as sodium carbonate or triethylamine in a suitable solvent or mixture of solvents such as dioxane and water, or dichloromethane to yield 164 as described by Pfeifer, M.; Robinson, J. A. *J. Chem. Soc. Chem. Commun.* 1998, 1977.

Templates of type (c1) can be prepared according to Schemes 34 to 37.

Scheme 34

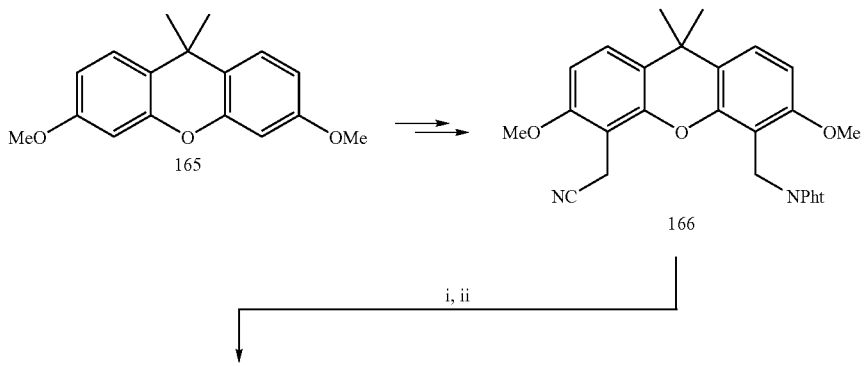

i, ii

-continued

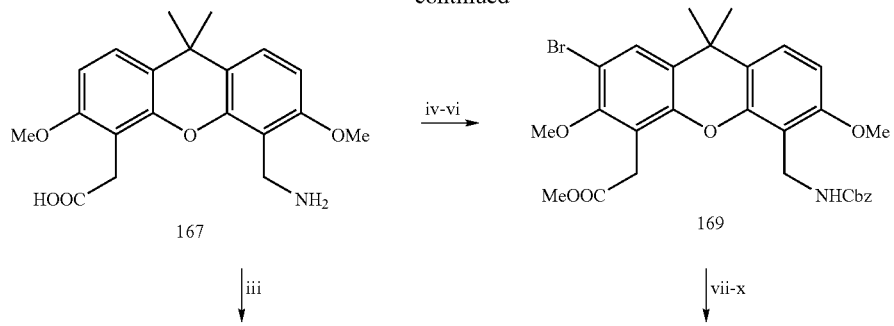

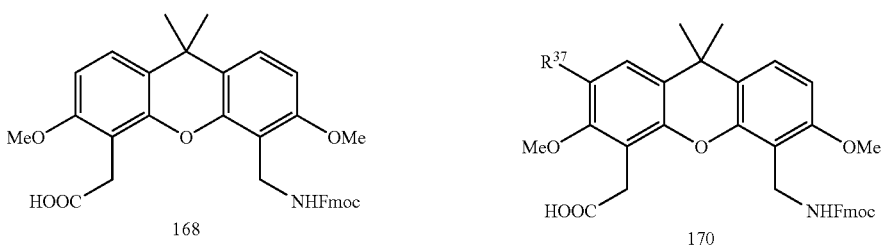

i: 166 can be synthesized from 165 according to P. Waldmeier, "Solid-supported synthesis of highly substituted xanthene-derived templates for the synthesis of β-turn stabilized cyclic peptide libraries", PhD-thesis, University of Zurich, 1996. For cleaving the phthalimide group 166 is conveniently submitted to hydrazinolysis, e.g. by treatment with hydrazine hydrate in a suitable solvent such as ethanol at an elevated temperature, e.g. at about 80° C.

ii: The intermediate aminonitrile is saponified, conveniently under basic conditions, e.g. with aqueous sodium hydroxide in a suitable solvent such as ethanol at an elevated temperature, conveniently under reflux, to yield 167.

iii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 168 as described by P. Waldmeier, "Solid-supported synthesis of highly substituted xanthene-derived templates for the synthesis of β-turn stabilized cyclic peptide libraries", PhD-thesis, University of Zurich, 1996.

iv: Regioselective bromination of 167 is performed preferably with bromine in acetic acid and dichloromethane. In a similar fashion $R^{37}=NO_2$ can be introduced by treatment with $HNO_3$ in acetic acid and $R^{37}=CH_2—NPht$ by treatment with hydroxymethyl phthalimide in $H_2SO_4$.

v: The amino group is conveniently Cbz-protected with reagents such as benzyloxycarbonyl chloride or succinimide in a suitable solvent such as dioxane in presence of a base such as aqueous sodium hydroxide.

vi: The carboxylic acid group is esterified, preferably with DBU and methyl iodide in DMF to yield 169.

vii: Introduction of lower all, substituted lower alkyl and aryl substituents ($R^{37}$), conveniently by palladium(0)-catalyzed Stille-(Stille, J. K. *Angew. Chem.* 1986, 68, 504) and Suzuki-couplings (Oh-e T.; Mijaura, N.; Suzuki, A. *J. Org. Chem.* 1993, 58, 2201). Any other functionalization known for aryl bromides can be employed for introduction of substituents $R^{37}$.

viii: Removal of the Cbz-group, e.g. by hydrogenation using $H_2$ and a catalyst such as palladium on charcoal in a suitable solvent such as ethanol, DMF and ethyl acetate.

ix: Hydrolysis of the ester group, conveniently under acidic conditions, e.g. with 25% aqueous hydrochloric acid in a suitable solvent such as dioxane at an elevated temperature, preferably at about 100° C.

x: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 170.

Scheme 35

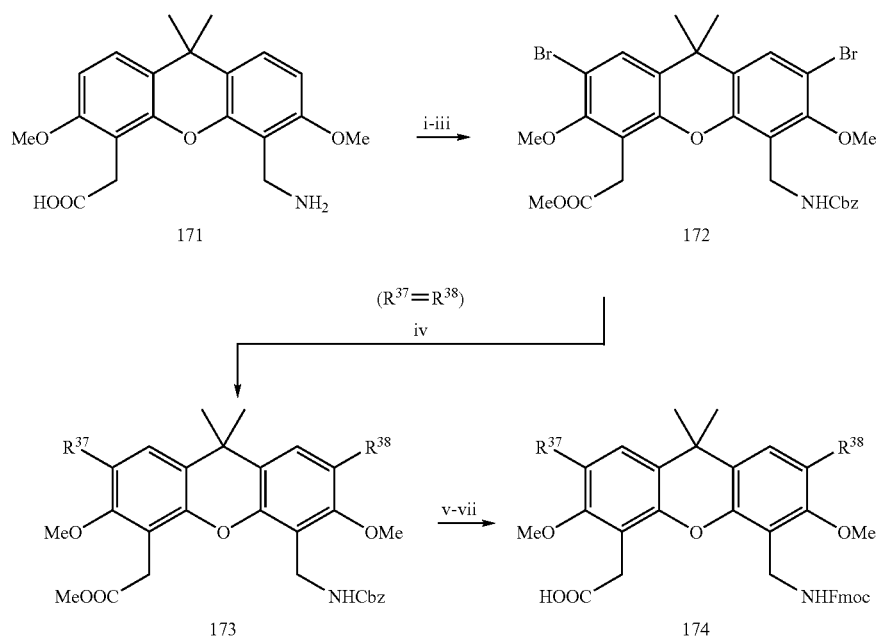

i: Double ortho-bromination of 171 is performed preferably with excess bromine in acetic acid and dichloromethane. In a similar fashion $R^{37}=R^{38}=NO_2$ can be introduced by treatment with $HNO_3$ in acetic acid and $R^{37}=R^{38}=CH_2-NPht$ by treatment with hydroxymethyl phthalimide in $H_2SO_4$.

ii: The amino group is protected, conveniently Cbz-protected, with reagents such as benzyloxycarbonyl chloride or succinimide in a suitable solvent such as dioxane in the presence of a base such as aqueous sodium hydroxide.

iii: The carboxylic acid group is esterified, preferably with DBU and methyl iodide in DMF to yield 172.

iv: Introduction of lower alkyl, substituted lower alkyl and aryl substituents ($R^{37}=R^{38}$), e.g. by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{37}$ and $R^{38}$.

v: Removal of the Cbz-group of 173, e.g. by hydrogenation using $H_2$ and a catalyst such as palladium on charcoal in a suitable solvent such as ethanol, DMF or ethyl acetate.

vi: Hydrolysis of the ester group, conveniently under acidic conditions, e.g. with 25% aqueous hydrochloric acid in a suitable solvent such as dioxane at an elevated temperature, conveniently at about 100° C.

vii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 174.

Scheme 36

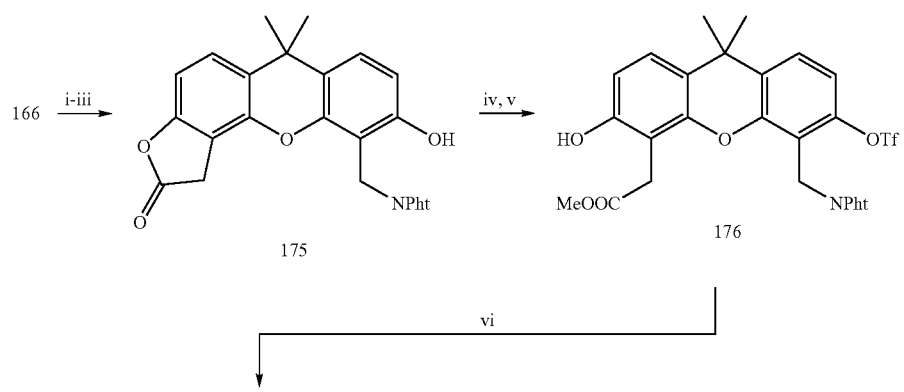

-continued

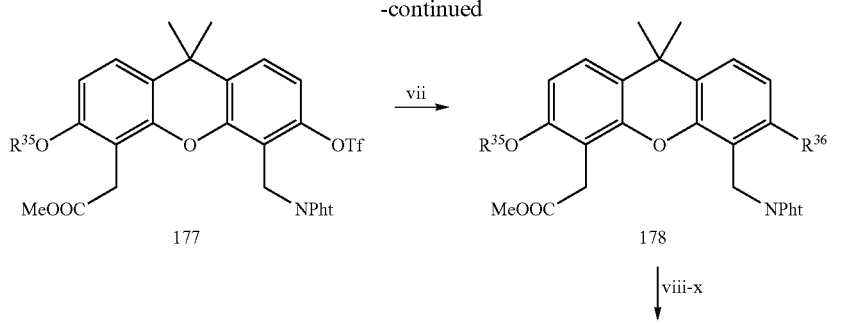

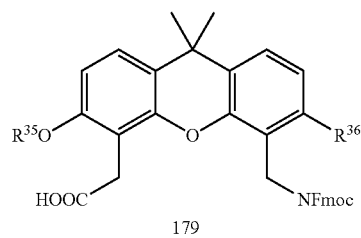

i: Cleavage of the methoxy groups of 166, preferably by treatment with an excess of boron tribromide in a suitable solvent such as dichloromethane.
ii: Hydrolysis of the cyano group under acidic conditions, preferably with 25% aqueous hydrochloric acid in a suitable solvent such as dioxane at an elevated temperature, conveniently at about 100° C.
iii: The resulting acid is treated with a dehydrating agent such as thionyl chloride in a suitable solvent such as dioxane to yield 175.
iv: Treatment of 175 with an appropriate triflating reagent, preferably trifluoromethanesulfonic acid anhydride in the presence of a base such as 2,6-di-tert.-butyl-pyridine in a suitable solvent such as dichloromethane.
v: Heating of the intermediate, conveniently in a suitable solvent such as methanol.
vi: Introduction of lower allyl or aryl-lower alkyl ($R^{35}$) by alkylation to yield 177. Any other functionalization known for phenol groups can be employed for introduction of substituents $R^{35}$.
vii: Introduction of lower alkyl or aryl ($R^{36}$), conveniently by palladium(0)-catalyzed Suzuki-coupling (Oh-e, T.; Mijaura, N.; Suzuki, A. *J. Org. Chem.* 1993, 58, 2201) to yield 178. Any other functionalization known for aryl bromides can be employed for introduction of substituents $R^{36}$.
viii: Hydrolysis of the ester group under acidic conditions, conveniently with 25% aqueous hydrochloric acid in a suitable solvent such as dioxane at an elevated temperature, e.g. at about 100° C.
ix: Cleavage of the phthalimido group, conveniently by hydrazinolysis, e.g. with hydrazine hydrate in a suitable solvent such as ethanol.
x: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 179.

Scheme 37

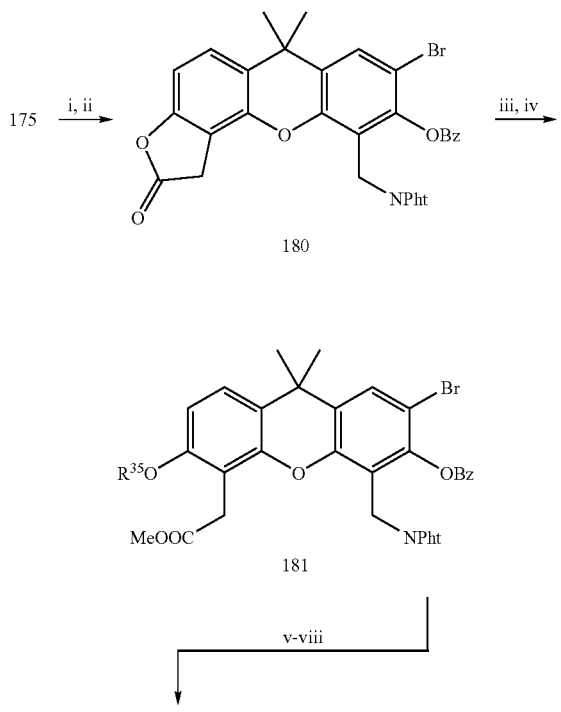

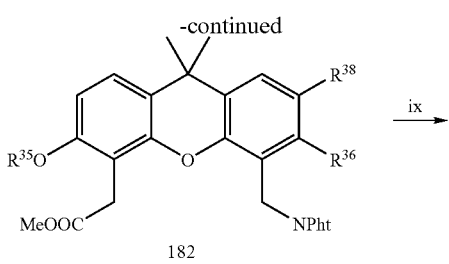

182

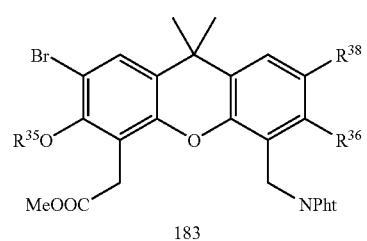

183

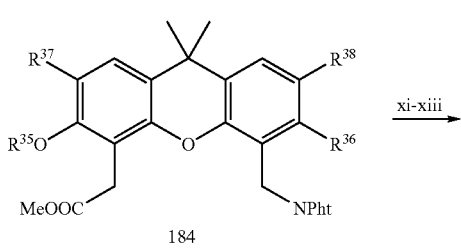

184

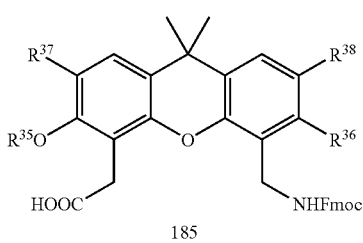

185 i: Bromination of 175 using reagents such as bromine in a mixture of acetic acid and dichloromethane at temperatures ranging from about 0° C. to about room temperature.

ii: Benzoylation of the hydroxy group using an appropriate acylating agent such as benzoyl chloride or benzoic acid anhydride, a base such as pyridine or triethylamine and a suitable solvent such as dichloromethane to yield 180.

iii: 180 is treated with methanol and a catalytic amount of an acidic catalyst such as camphor sulfonic acid under heating.

iv: Introduction of lower alkyl or aryl-lower alkyl ($R^{35}$) by alkylation using a base such as sodium hydride or potassium tert.-butoxide in a solvent such as tetrahydrofuran, dimethoxyethane or DMF gives 181.

v: Lower alkyl, substituted lower alkyl and aryl substituents ($R^{38}$) are introduced, e.g. by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{38}$.

vi: For cleaving the benzyloxy group the intermediate is conveniently heated with sodium cyanide adsorbed on aluminum oxide and methanol.

vii: Treatment with an appropriate triflating reagent, preferably trifluoromethanesulfonic acid anhydride, in the presence of a base such as 2,6di-tert.-butyl-pyridine in a suitable solvent such as dichloromethane.

viii: Introduction of lower alkyl and aryl substituents ($R^{36}$), e.g. by palladium(0)-catalyzed Stille-(Stille, J. K. Agnew. Chem. 1986, 68, 504) and Suzuki-couplings (Oh-e, T.; Mijaura, N.; Suzuki, A. J. Org. Chem. 1993, 58, 2201) yields 182. Any other functionalization known for aryl bromides can be employed for introduction of substituents $R^{36}$.

ix: Bromination under standard conditions such as using bromine in acetic acid and dichloromethane at temperatures ranging from about 0° C. to about room temperature.

x: Lower alkyl, substituted lower alkyl and aryl substituents ($R^{37}$) are introduced, e.g. by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201) to yield 184. Any other functionalization known for aryl bromides can be employed for introduction of substituents $R^{37}$.

xi: The ester group is hydrolyzed under acidic conditions, conveniently with 25% aqueous hydrochloric acid in a suitable solvent such as dioxane at an elevated temperature, e.g. at about 100° C.

xii: The phthalimido group is cleaved, e.g. by hydrazinolysis, conveniently with hydrazine hydrate in a suitable solvent such as ethanol.

xiii: The intermediate free amino acid formed is conveniently protected with reagents such as 9-fluorenylmethoxcarbonyl chloride or 9-fluorenylmethoxycarbonyl succinimide using a base such as sodium carbonate or triethylamine in a suitable solvent or mixture of solvents such as dioxane and water, or dichloromethane to yield 185.

Templates of type (c2) can be prepared as shown in Schemes 38 and 39.

Scheme 38

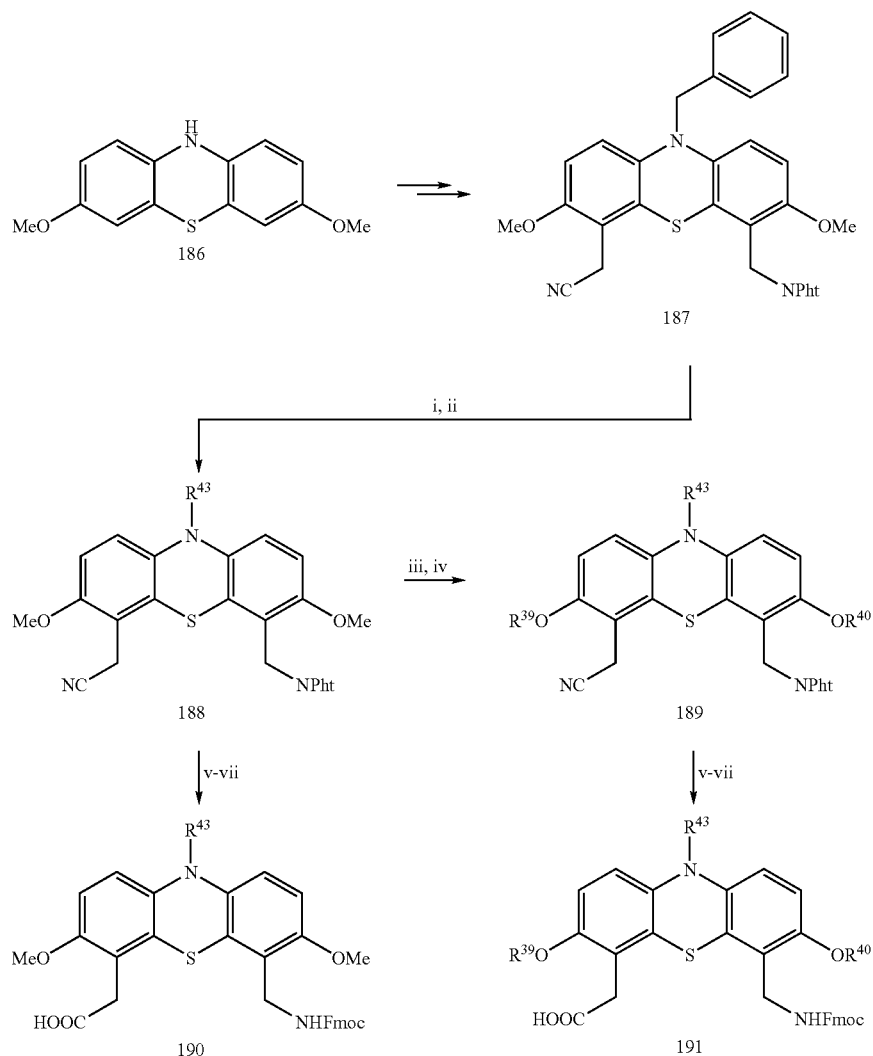

i: 3,7-Dimethoxyphenothiazine 186 is prepared and converted into 187 according to Müller, K.; Obrecht, D.; Knierzinger, A.; Spiegler, C.; Bannwarth, W.; Trzeciak, A.; Englert, G.; Labhardt, A; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513-531; Bannwarth, W.; Gerber, F.; Grieder, A; Knierzinger, A.; Müller, K.; Obrecht. D.; Trzeciak, A. Can. Pat. Appl. CA2101599 (131 pages). The benzyl group is cleaved off from 187 conveniently by hydrogenation, e.g. with $H_2$ and a catalyst such as palladium on charcoal in a suitable solvent such as ethanol, DMF or ethyl acetate.

ii: Introduction of lower alkyl ($R^{43}$) by alkylation using an appropriate alkylating agent ($R^{43}$—X'; X'=OTf, Br, I) and strong bases such as sodium amide in liquid ammonia or sodium hydride in tetrahydrofuran, dioxan or DM in the presence of a phase transfer catalyst such as TDA-I. In a similar manner substituted lower alkyl (43) can be introduced; thus, for example $R^{43}$=$CH_2COOR^{55}$ and CH=$CH_2COOR^{55}$ can be introduced by treatment with the appropriate 2-halo acetic and, respectively, 3-halo propionic acid derivatives. Any other functionalization known for diarylamines can be employed for introduction of substituents $R^{43}$.

iii: Cleavage of the methoxy groups of 188, conveniently by treatment with an excess of boron tribromide in a suitable solvent such as dichloromethane at temperatures ranging from about −20° C. to about room temperature.

iv: For the introduction of lower alkyl, substituted lower alkyl or aryl-lower alkyl substituents ($R^{39}$ and $R^{40}$) the intermediate bis-phenol derivative is conveniently reacted with a reagent of the formula $R^{39}$-and $R^{40}$—X' (X'=OTf, Br, I) in the presence of strong bases such as sodium hydride in tetrahydrofuran, dioxan or DMF in the presence of a phase transfer catalyst such as TDA-I. Any other functionalization known for phenol groups can be employed for introduction of substituents $R^{39}$ and $R^{40}$.

v: The cyano group of 188 and, respectively, 189 is hydrolyzed, conveniently under acidic conditions, e.g. with 25% aqueous hydrochloric acid in a suitable solvent such as dioxane at an elevated temperature, e.g. at about 100° C.

vi: The phthalimide group of the intermediate is cleaved, conveniently by hydrazinolysis, e.g. with hydrazine hydrate in a suitable solvent such as ethanol.

vii: The free amino group is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 190 and, respectively, 191.

$R^{41}=R^{42}=CH_2$—NPht by treatment with hydroxymethyl phthalimide in $H_2SO_4$. Any other functionalization by electrophilic aromatic substitution known can be employed for introduction of substituents $R^{41}$ and $R^{42}$.

iv: The amino group is protected, conveniently Cbz-protected, with reagents such as benzyloxycarbonyl chloride or succinimide in a suitable solvent such as dioxane in the presence of a base such as aqueous sodium hydroxide.

v: The carboxylic acid group is esterified, preferably with DBU and methyl iodide in DMF to yield 193.

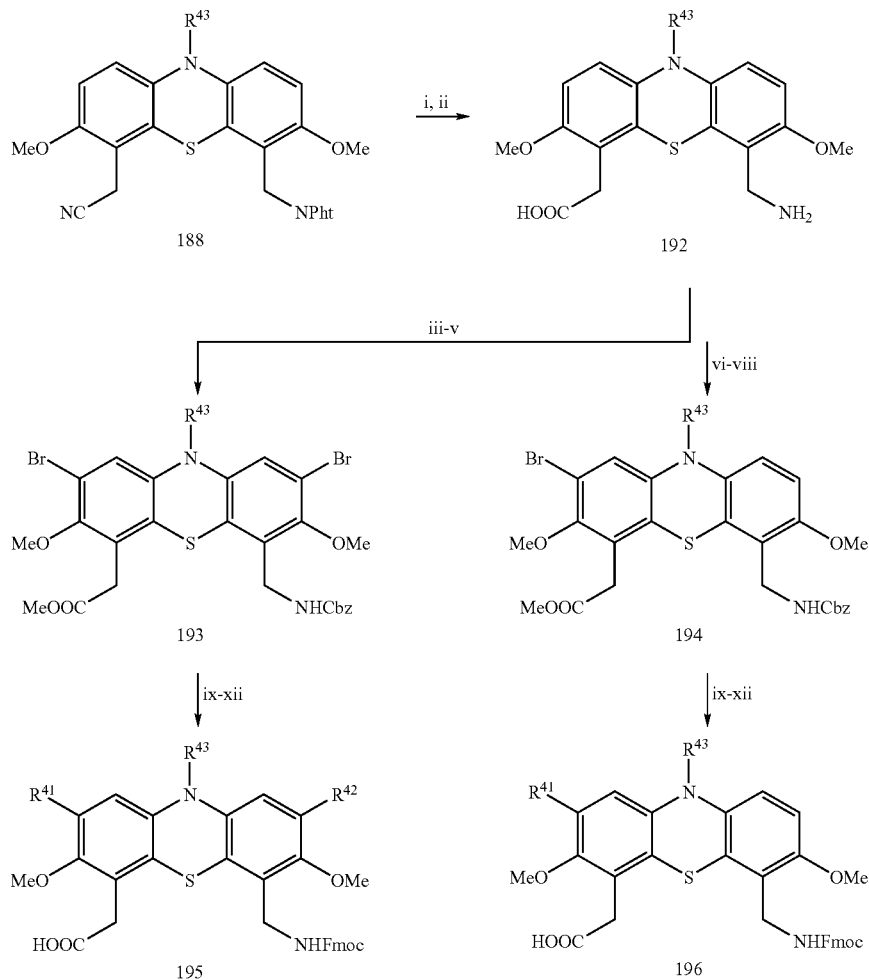

i: The cyano group of 188 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 192.

iii: Double ortho-bromination of 192 is performed preferably with excess bromine in acetic acid and dichloromethane. In a similar fashion $R^{41}=R^{42}=NO_2$ can be introduced by treatment with $HNO_3$ in acetic acid and vi: Regioselective bromination of 192 is performed preferably with bromine in acetic acid and dichloromethane. In a similar fashion $R^{41}=NO_2$ can be introduced by treatment with $HNO_3$ in acetic acid and $R^{41}=CH_2$—NPt by treatment with hydroxymethyl phthalimide in $H_2SO_4$. Any other functionalization by electrophilic aromatic substitution known can be employed for introduction of substituents $R^{41}$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 194.

ix: Introduction of lower alkyl, substituted lower alkyl and aryl substituents ($R^{41}$) for 194 and ($R^{41}$ and $R^{42}$) for 193, conveniently by palladium(0)-catalyzed Stille-(Stille, J. K. *Angew. Chem.* 1986, 68, 504) and Suzuki-couplings (Oh-e, T.; Mjaura, N.; Suzuki, A. *J. Org. Chem.* 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenyl-methoxcarbonyl chloride or 9-fluorenylmethoxcarbonyl succinimide using a base such as sodium carbonate or triethylamine in a suitable solvent or mixture of solvents such as dioxane and water, or dichloromethane to yield 195 and 196.

Templates of type (c3) can be prepared as shown in Schemes 40 and 41.

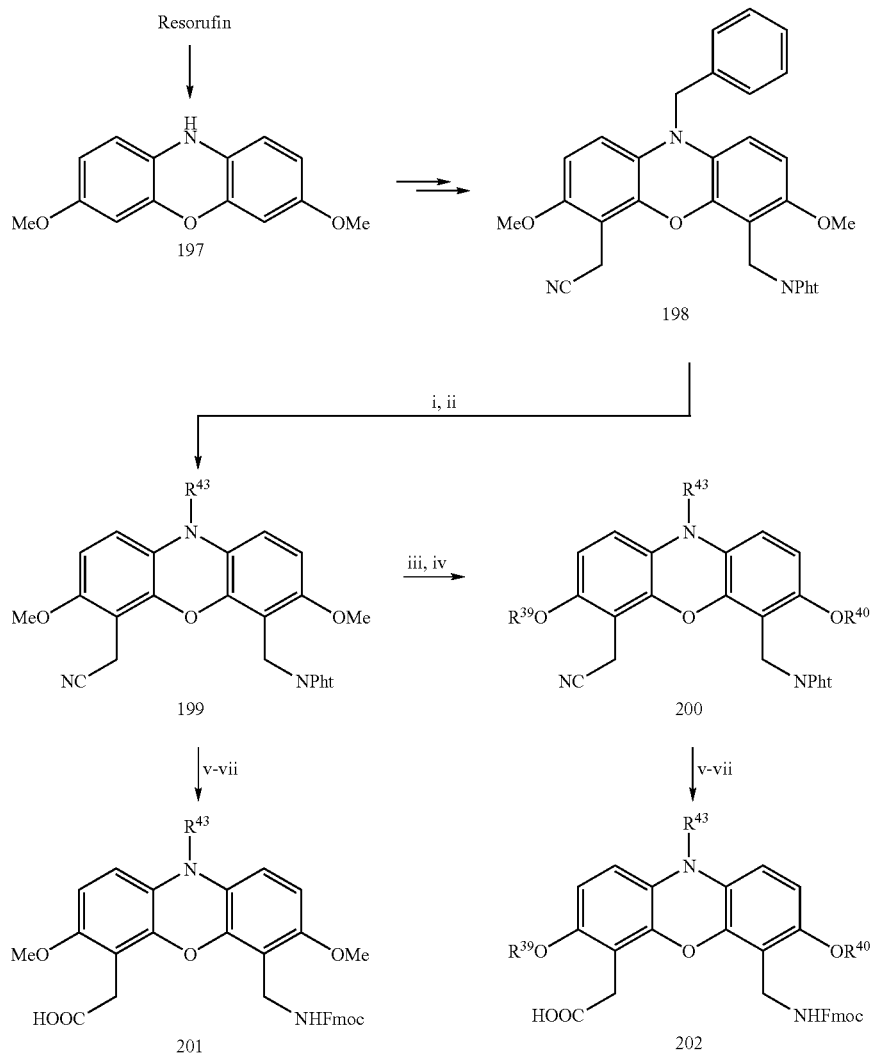

Scheme 40 i: 197 can be prepared from commercial resorufin and coverted into 198 according to Müller, K.; Obrecht, D.; Knierzinger, A.; Spiegler, C.; Bannwarth, W.; Trzeciak, A.; Englert, G.; Labhardt, A; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513-531; Bannwarth, W.; Gerber, F.; Grieder, A.; Knierzinger, A.; Miller, K.; Obrecht. D.; Trzeciak, A. Can. Pat. Appl. CA2101599 (131 pages). For splitting off the benzyl group 198 is conveniently hydrogenated e.g. with $H_2$ and a catalyst such as palladium on charcoal in a suitable solvent such as ethanol, DMF or ethyl acetate.

ii: Introduction of lower alkyl ($R^{43}$) by alkylation with $R^{43}$—X' (X'=OTf, Br, I) using strong bases such as sodium amide in liquid ammonia or sodium hydride in tetrahydrofuran, dioxan or DMF in the presence of a phase transfer catalyst such as TDA-I to yield 199. In a similar manner substituted lower alkyl ($R^{43}$) can be introduced; thus, for example, $R^{43}$=$CH_2COOR^{55}$ and $CH^2CH_2COOR^{55}$ can be introduced by treatment with the appropriate 2-halo acetic and, respectively, 3-halo propionic acid derivatives. Any other functionalization of diarylamino groups known can be employed for introduction of substituents $R^{13}$.

v: The cyano group of 199 and, respectively, 200 is hydrolyzed under acidic conditions, e.g. with 25% aqueous hydrochloric acid in a suitable solvent such as dioxane at an elevated temperature, conveniently at about 100° C.

vi: The phthalimide group is cleaved, conveniently by hydrazinolysis, e.g. with hydrazine hydrate in suitable solvent such as ethanol.

vii: The free amino group is conveniently protected with reagents such as 9-fluorenylmethoxcarbonyl chloride or 9-fluorenylmethoxcarbonyl succinimide using a base such as sodium carbonate or triethylamine in suitable solvent or mixture of solvents such as dioxane and water, or dichloromethane to yield 201 and, respectively, 202.

Scheme 41

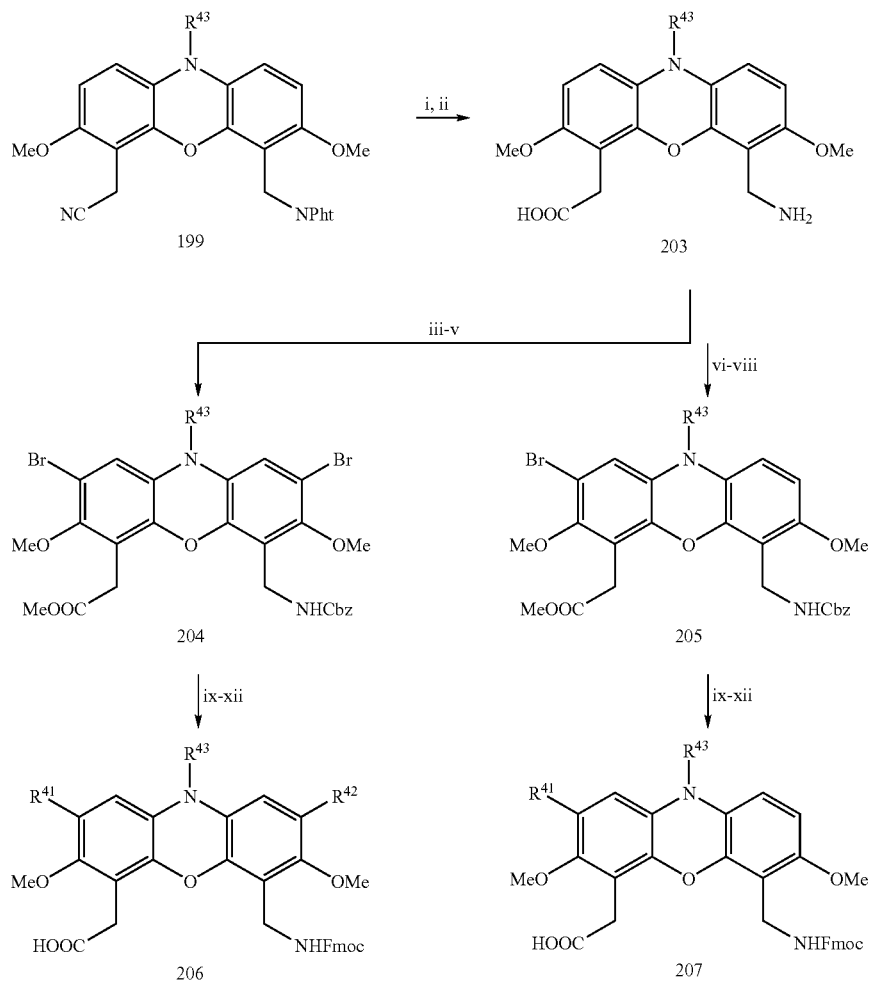

iii: Cleavage of the methoxy groups of 199, conveniently by treatment with excess boron tribromide in dichloromethane at temperatures ranging from about −20° to about room temperature.

iv: The intermediate bis-phenol derivative is preferably reacted with $R^{39}$ and $R^{40}$—X' (X'=OTf, Br, I) in the presence of strong bases such as sodium hydride in tetrahydrofuran, dioxan or DMF in the presence of a phase transfer catalyst such as TDA-I. Any other functionalization for phenol groups can be employed for introduction of substituents $R^{39}$ and $R^{40}$.

i: The cyano group of 199 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 203.

iii: Double ortho-bromination of 203 is performed preferably with excess bromine in acetic acid and dichloromethane. In a similar fashion $R^{41}$=$R^{42}$=$NO_2$ can be introduced by treatment with $HNO_3$ in acetic acid and $R^{41}=R^{42}=CH_2-NPht$ by treatment with hydroxymethyl phthalimide in $H_2SO_4$. Any other functionalization by electrophilic aromatic substitution can be employed for introduction of substituents $R^{41}$ and $^{42}$.

iv: The amino group is protected, conveniently Cbz-protected, with reagents such as benzyloxycarbonyl chloride or succinimide in a suitable solvent such as dioxane in the presence of a base such as aqueous sodium hydroxide.

v: The carboxylic acid group is esterified, preferably with DBU and methyl iodide in DMF to yield 204.

vi: Regioselective bromination of 203 is performed preferably with bromine in acetic acid and dichloromethane. In a similar fashion $R^{41}=NO_2$ can be introduced by treatment with $HNO_3$ in acetic acid and $R^{41}=CH_2-NPht$ by treatment with hydroxymethyl phthalimide in $H_2SO_4$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 205.

ix: Introduction of lower alkyl substituted lower alkyl and aryl substituents ($R^{41}$) for 205 and ($R^{41}$ and $R^{42}$) for 204, conveniently by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield 206 and 207.

Templates(d) can be prepared according to D. Obrecht, U. Bohdal, C. Lehmann, P. Schönholzer, K. Müller, Tetrahedron 1995, 51, 10883; D. Obrecht, C. Abrecht, M. Altorfer, U. Bohdal, A. Grieder, M. Kleber, P. Pfyffer, K. Müller, Helv. Chim. Acta 1996, 79, 1315-1337.

Templates (e1) and (e2): See R. Mueller, L. Revesz, Tetrahedron Lett. 1994, 35, 4091; H. -G. Lubell, W. D. Lubell, J. Org. Chem. 1996, 61, 9437; L. Colombo, M. DiGiacomo, G. Papeo, O. Carugo, C. Scolastico, L. Manzoni, Tetrahedron Lett. 1994, 35, 4031.

Templates (e3): See S. Hanessian, B. Ronan, A. Laoui, Bioorg. Med. Chem. Lett. 1994, 4, 1397.

Templates (e4): See S. Hanessian, G. McNaughton-Smith, Bioorg. Med. Chem. Lett. 1996, 6, 1567.

Templates (f): See T. P. Curran, P. M. McEnay, Tetrahedron Lett. 1995, 36, 191-194.

Templates (g): See D. Gramberg, C. Weber, R. Beeli, J. Inglis, C. Bruns, J. A. Robinson, Helv. Chem. Acta 1995, 78, 1588-1606; K. H. Kim, J. P. Dumas, J. P. Germanas, J. Org. Chem. 1996, 61, 3138-3144.

Templates (h): See S. de Lombart, L. Blanchard, L. B. Stamford, D. M. Sperbeck, M. D. Grim, T. M. Jenson, H. R. Rodriguez, Tetrahedron Lett. 1994, 35, 7513-7516.

Templates (i1): See J. A. Robl, D. S. Karanewski, M. M. Asaad, Tetrahedron Lett. 1995, 5, 773-758.

Templates (i2): See T. P. Burkholder, T. -B. Le, E. L. Giroux, G. A. Flynn, Bioorg. Med. Chem. Lett. 1992, 2, 579.

Templates (i3) and (i4): See L. M. Simplins, J. A. Robl, M. P. Cimarusti, D. E. Ryono, J. Stevenson, C. -Q. Sun, E. W. Petrillo, D. S. Karanewski, M. M. Asaad, J. E. Bird, T. R. Schaeffer, N. C. Trippodo, Abstracts of papers, $210^{th}$ Am. Chem. Soc Meeting, Chicago, Ill, MEDI 064 (1995).

Templates (k): See D. BenIshai, A. R. McMurray, Tetrahedron 1993, 49, 6399.

Templates (l): See E. G. von Roedem, H. Kessler, Angew. Chem. Int. Ed. Engl. 1994, 33, 687-689.

Templates (m): See R. Gonzalez-Muniz, M. J. Dominguez, M. T. Garcia-Lopez, Tetrahedron 1992, 48, 5191-5198.

Templates (n): See F. Esser, A. Carpy, H. Briem, H. Koppen, K. -H. Pook, Int. J. Pept. Res. 1995, 45, 540-546.

Templates (o): See N. De la Figuera, I. Alkorta, T. Garcia-Lopez, R. Herranz, R. Gonzalez-Muniz, Tetrahedron 1995, 51, 7841.

Templates (p): See U. Slomcynska, D. K. Chalmers, F. Cornille, M. L. Smythe, D. D. Benson, K. D. Moeller, G. R. Marshall, J. Org. Chem. 1996, 61, 1198-1204.

Medicaments containing a β-hairpin mimetis of general formula I, a solvate or a salt thereof are likewise objects of the present invention, as is a process for the manufacture of such medicaments which comprises bringing one or more of said compounds and, where desired, one or more additional therapeutically valuable substances into a galenical dosage form.

For the control or prevention of a given illness amenable to treatment with protease inhibitors, the β-hairpin mimetics of the invention can be administered singly, as mixtures of several β-hairpin mimetics, in combination with other inhibitors of protease enzymes or in combination with other pharmaceutically active agents. The β-hairpin mimetics of the invention can be administered per se or as pharmaceutical compositions. The dosage of the active substance, that is, a compound of formula I, can vary within wide limits and will, of course, be fitted to the individual requirements in each particular case. In general, in the case of oral or parenteral, for example, intravenous or subcutaneous, administration a dosage of about 0.1-29 mg/kg, preferably of about 0.5-5 mg/kg, per day should be appropriate for adults, although the upper limit just given can also be increased or lowered, when this is shown to be indicated.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in aqueous solutions, preferably in physiologically compatible buffers such as Rink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the lie may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulation described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as free bases or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For use to treat or prevent diseases amenable to treatment with protease inhibitors, the β-hairpin pepidomimetics of the invention, or compositions thereof, are administered or applied in a therapeutically effective amount. By therapeutically effective amount is meant an amount effective in ameliorating the symptoms of, or ameliorate, treat or prevent diseases related to protease activity. Determination of a therapeutically effective amount is well within the capacities of those skilled in the art, especially in view of the detailed disclosure provided herein.

Initial dosages can also be determined from in vivo data, e.g. animal models, using techniques that are well known in the art. One having ordinary skills in the art could readily optimize administration to humans based on animal data.

Dosage amount and interval may be adjusted individually to provide plasma levels of the β-hairpin peptidomimetics of the invention which are sufficient to maintain the therapeutic effect. Usual patient dosages for administration by injection range from about 0.1-5 mg/kg/day, preferably from about 0.5 to 1 mg/kg/day. Therapeutically effective serum levels may be achieved by administering multiple doses each day.

The amount of β-hairpin peptidomimetics administered will, of course, be dependent on the subject being treated, on the subject's weight, the severity of the affliction, the manner of administration and the judgement of the prescribing physician.

Normally, a therapeutically effective dose of the β-hairpin peptidomimetics described herein will provide therapeutic benefit without causing substantial toxicity.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans.

The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

Compounds of formula I containing a free thiol group, i.e. compounds containing as $R^2$-$R^6$, $R^8$-$R^{10}$, $R^{12}$, $R^{13}$, $R^{15}$-$R^{19}$, $R^{21}$-$R^{29}$, $R^{33}$ or $R^{64}$ a residue of the formula —$(CH_2)_m$ (CHR⁶¹)ₓSR⁵⁶ in which R⁵⁶ is H, can be immobilized on gold-coated wawers, and interactions with ligands can be determined by means of the so-called surface plasmon resonance (SPR) biosensor analysis (cf. M. Fivash, E. M. Towler and R. J. Fisher, Curr. Opin. in Biotechnol. 1998, 9, 97-101; and R. L. Rich and D. G. Myszca, Curr. Opin. in Biotechnol. 2000, 11, 54-61).

The following Examples illustrate the invention m more detail but are not intended to limit its scope in any way. The following abbreviations are used in these Examples:

HBTU: 1-benzotriazol-1-yl-tetramethylurouniumhexafluorophosphate
(Knorr et al. *Tetrahedron Lett.* 1989, 30, 1927-1930)
HOBt: 1-hydroxybenzotriazole
DIEA: diisopropylethylamine
HOAT: 7-aza-1-hydroxybenzotriazole
HATU: O-(7-aza-benzotriazole-1-yl)-N,N,N',N'-tetramethyluronoium hexafluorophosphate
Carpino et al. *Tetrahedron Lett.* 1994, 35, 2279-2281)

EXAMPLES

1. Peptide Synthesis

Coupling of the First Protected Amino Acid Residue 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2Cl_2$ (2.5 ml) and allowed to swell at room temperature under constant stirring. The resin was treated with 0.415 mmol (1eq) of the first suitably protected amino acid residue (see below) and 284 µl (4eq) of diisopropylethylamine (DIEA) in $CH_2Cl_2$ (2.5 ml), the mixture was shaken at 25° C. for 15 minutes, poured onto the pre-swollen resin and stirred at 25° C. for 18 hours. The resin colour changed to purple and the solution remained yellowish. The resin was washed extensively ($CH_2Cl_2$/MeOH/DIEA 17/2/1; $CH_2Cl_2$, DMF; $CH_2Cl_2$; $Et_2O$, 3 times each) and dried under vacuum for 6 hours.

Loading was typically 0.6-0.7 mMol/g.

The following preloaded resins were prepared: Fmoc-Ser(tBu)O-chlorotritylresin and Fmoc-AlaO-chlorotritylresin.

1.1. Procedure 1

The synthesis was carried out using a Syro-peptide synthesizer (Multisyntech) using 24 to 96 reaction vessels. In each vessel was placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |
| 5 | 5 equiv. Fmoc amino acid/DMF +5 eq. HBTU +5 eq. HOBt +5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino acid

Cleavage of the Fully Protected Peptide Fragment

After completion of the synthesis, the resin was suspended in 1 ml (0.39 mmol) of 1% TFA in $CH_2Cl_2$ (v/v) for 3 minutes, filtered and the filtrate was neutralized with 1 ml (1.17 mMol, 3eq.) of 20% DIEA in $CH_2Cl_2$ (v/v). This procedure was repeated twice to ensure completion of the cleavage. The filtrate was evaporated to dryness and the product was fully deprotected to be analyzed by reverse phase-HPLC (column $C_{18}$) to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 Mol, 3 eq.) of HATU, 14.9 mg (0.110 mMol, 3 eq) of HOAt and 1 ml (0.584 mMol) of 10% DIEA in DMF (v/v) were added and the mixture vortexed at 20° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic peptide.

Deprotection and Purification of the Cyclic Peptide

The cyclic peptide obtained was dissolved in 1 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The residue was dissolved in a solution of $H_2O$/acetic acid (75/25: v/v) and the mixture extracted with di-isopropylether.

The water phase was dried under vacuum and then the product purified by preparative reverse phase HPLC.

After lyophilisation products were obtained as a white powder and analysed by ESI-MS. The analytical data comprising HPLC retension times and ESI-MS are shown in table 1.

Examples ex.1-11 (n=7) are shown in table 1. The peptides were synthesized staring with the amino acid at position P3 which was coupled to the resin. Starting resins were Fmoc-Ser(tBu)O-chlorotritylresin and Fmoc-AlaO-chlorotrityl resin, which were prepared as described above. The linear peptides were synthesized on solid support according to procedure 1 in the following sequence: P4-P6-P7-$^D$Pro-Pro-P1-P2-P3-resin, cleaved, cyclized, deprotected and purified as indicated.

Examples ex.12 and 13 (n=7) are also shown in table 1. The peptides were synthesized starting with the amino acid at position P3 which was grafted to the resin. Starting resin was Fmoc-Ser(tBu)O-chlorotritylresin, which was prepared as described above. The linear peptides were synthesized on solid support according to procedure 1 in the following sequence: P4-P5-P6-P7-$^D$Pro-(A8'-1)-P1-P2-P3-resin (ex 12) and, respectively, P4-P5-P6-P7-$^D$Pro-(A8"-1)-P1-P2-P3-resin (ex. 13), cleaved, cyclized, deprotected and purified as indicated.

Example ex.14 (n=7) is shown in table 1, too. The peptide was synthesized starting with the amino acid at position P3 which was grafted to the resin. Starting resin was Fmoc-Ser(tBu)O-chlorotritylresin, which was prepared as described above. The linear peptide was synthesized on solid support according to procedure 1 in the following sequence: P4-P5-P6-P7-(c1-1)-P1-P2-P3-resin, cleaved, cyclized, deprotected and purified as indicated.

Building block (c1-1) is described below.

Example ex.15 (n=11) is likewise shown in table 1. The peptide was synthesized starting with the amino acid at position P5 which was coupled to the resin. Staring resin was Fmoc-Ser(tBu)O-chlorotritylresin, which was prepared as described above. The linear peptide was synthesized on solid support according to procedure 3 (see below)in the following sequence: P6-P7-P8-P9-P10-P11-$^D$Pro-Pro-P1-P2-P3-P4-P5-resin, cleaved, cyclized, oxidized, deprotected and purified as indicated.

TABLE 1

Examples ex. 1-15

| Ex. | Seq. ID | Sequence P1 to P7 (ex. 1-14) P1 to P11 (ex. 15) | Template | RT (min.) | Obtained mass [M + H]$^+$ |
|---|---|---|---|---|---|
| 1 | SEQ ID NO:1 | TKSIPPI | $^D$Pro-$^L$Pro | 13.39$^{a)}$ | 931.63 |
| 2 | SEQ ID NO:2 | AKSIPPI | $^D$Pro-$^L$Pro | 14.57$^{a)}$ | 901.8 |
| 3 | SEQ ID NO:3 | TASIPPI | $^D$Pro-$^L$Pro | 14.28$^{a)}$ | 874.06 |
| 4 | SEQ ID NO:4 | TKAIPPI | $^D$Pro-$^L$Pro | 13.97$^{a)}$ | 915.79 |
| 5 | SEQ ID NO:5 | TKSAPPI | $^D$Pro-$^L$Pro | 12.71$^{a)}$ | 889.64 |
| 6 | SEQ ID NO:6 | TKSIAPI | $^D$Pro-$^L$Pro | 14.40$^{a)}$ | 905.8 |
| 7 | SEQ ID NO:7 | TKSIPAI | $^D$Pro-$^L$Pro | 13.44$^{a)}$ | 905.72 |
| 8 | SEQ ID NO:8 | TKSIPPA | $^D$Pro-$^L$Pro | 11.83$^{a)}$ | 889.7 |
| 9 | SEQ ID NO:9 | TYSIPPI | $^D$Pro-$^L$Pro | 15.99$^{a)}$ | 966.7 |
| 10 | SEQ ID NO:10 | TWSIPPI | $^D$Pro-$^L$Pro | 17.32$^{a)}$ | 989.7 |
| 11 | SEQ ID NO:11 | TFSIPPI | $^D$Pro-$^L$Pro | 17.02$^{a)}$ | 950.7 |
| 12 | SEQ ID NO:12 | TKSIPPI | $^D$Pro-A8'-1 | 11.28$^{a)}$ | 1030.2 |
| 13 | SEQ ID NO:13 | TKSIPPI | $^D$Pro-A8''-1 | 12.55$^{a)}$ | 1044.3 |
| 14 | SEQ ID NO:14 | TKSIPPI | (c1-1) | 13.15$^{b)}$ | 1076.5 |
| 15 | SEQ ID NO:15 | RCTKSIPPICF | $^D$Pro-$^L$Pro | 16.07$^{a)}$ | 1439.7 |

$^{a)}$Vydac C-18-column; gradient: 5% MeCN/H$_2$O + 0.1% CF$_3$COOH for 2 min.; then 50% MeCN/H$_2$O + 0.1% CF$_3$COOH over 15 min. and 50-100% MeCN/H$_2$O + 0.1% CF$_3$COOH over 4 min.
$^{b)}$Vydac C-18-column; gradient: 5-60% MeCN/H$_2$O + 0.1% CF$_3$COOH over 20 min.
$^{c)}$Nd: not determined 1.2. Procedure 2

Example ex.13 was also synthesized using procedure 2.

The peptide synthesis is carried out by solid phase method using standard Fmoc chemistry on a peptide synthesizer-ABI 433A.

The first amino acid, Fmoc-Ser(tBu)-OH (0.68g, 1.2 equiv.) is coupled to the 2-chlorotritylchloride resin (Barlos et al. *Tetrahedron Lett.* 1989, 30, 3943-3946) (2g, 0.83 mmol/g) in presence of DIEA (1.12 mL, 4 equiv.) in CH$_2$Cl$_2$ (20 mL), with swirling for 3 hr at room temperature. The resin is then washed with 3×CH$_2$Cl$_2$/MeOH/DIEA(17:2:1), 3×CH$_2$Cl$_2$, 2×DMF, 2×CH$_2$Cl$_2$, 2×MeOH. Finally, the resin is dried under vacuum and the substitution level was measured by weight increase (~0.6 mmol/g).

In case it is desired to use different acylating agents, the resin with the synthesized linear peptide, Ile-Lys(Boc)-Pro-Pro-Ile-$^D$Pro-212-Thr(tBu)-Lys(Boc)-Ser(tBu)-resin, is preferably divided into equal parts and placed in different reaction vessels in order to carry out the acylation reaction in parallel format. The coupling and deprotection reactions in the following steps are monitored by Kaiser's test (Kaiser et al. *Anal. Biochemistry* 1970, 43, 595).

Removal of Alloc Protecting Group

To the linear peptide resin (100 mg per reaction vessel) is added Pd(PPh$_3$)$_4$ (15 mg, 0.5 equiv.) under argon followed by dry CH$_2$Cl$_2$ (10 mL) and phenylsilane (17 μL, 30 equiv.). The reaction mixture is left for 1 hour in the dark, filtered, and the resin is washed twice with CH$_2$Cl$_2$, DMF, and CH$_2$Cl$_2$.

Acylation of 4—Amino-Proline Group

To the resin is added the corresponding acylating agent (usually a carboxyxlic acid (R$^{64'}$COOH, 3 equiv.), HBTU (22.3 mg, 4 equiv.), HOBt (8 mg, 4 equiv.) and DIEA (125 μL, 6 equiv.) in DMF (2 mL) for 1.5-2 hrs at room temperature. The resin is filtered, washed with 2×DMF, 3×CH$_2$Cl$_2$, 2×DMF.

Deprotection of N$^\alpha$-Fmoc Group

Deprotection of the Fmoc-group is achieved by treating the resin with 20% piperidine in DMF for 20 min. The resin is subsequently filtered and washed three times with DMF, and CH$_2$Cl$_2$, and twice with DMF, and CH$_2$Cl$_2$.

Cleavage of Peptide From the Resin

The linear side-chain protected peptide is cleaved from the resin using AcOH:TFE:CH$_2$Cl$_2$ (2:2:6, v/v/v) for 2 hrs at room temperature. The resin is filtered off and washed twice with a mixture of AcOH:TFE:DCM and once with CH$_2$Cl$_2$. The filtrate is subsequently diluted with hexane (14 times by vol.) and concentrated. Evaporation is repeated twice with hexane to remove traces of AcOH. The residue is dried under vacuum. Yield of the linear protected peptide is generally about 40-50 mg.

Cyclization of the Linear Protected Peptide

Cyclization is carried out in DMF at a concentration of 5 mg/mL using HATU (13.12 mg, 3 equiv.), HOAT (4.7 mg, 3 equiv.), DIEA (153 μL, 6 equiv.). The reaction mixture is stirred for 16 hrs at room temperature and the completion of reaction is monitored by HPLC. After the evaporation of DMF, CH$_3$CN/H$_2$O (90/10, v/v) is added to the residue and extracted with DCM. The organic layer is washed once with water and evaporated to dryness. Dried under vacuum.

Cleavage of Side Chain Protecting Groups

The final deprotection of the side-chain protecting groups is carried out by treating the peptide with TFA:triisopropyl-silane:H$_2$O (95:2.5:2.5, v/v/v) at room temperature for 3 hrs. TFA is then evaporated and the residue triturated with cold ether.

Purification

The crude peptides thus obtained are analyzed and purified by HPLC on a VYDAC C18 preparative column using 5-60% CH$_3$CN/H$_2$O+0.1% TFA in 30 min as gradient and a flow rate of 10 ml/min. The purity of the final peptide is checked by analytical HPLC and by ESI-MS.

1.3. Procedure 3

Procedure 3 describes the synthesis of β-hairpin mimetics having disulfide β-strand linkages.

n=11: The peptides are synthesized according to procedure 1 starting with the amino acid at position P5, coupled to the resin. The linear peptides are synthesized on solid support according to procedure 1 in the following sequence: P6-P7-P8-P9-P10-P11-$^D$Pro-Pro-P1-P2-P3-P4-P5-resin, where at positions P2 and P10 Fmoc-Cys(Acm)OH or Fmoc-Cys(Tr)OH are incorporated. The linear peptides are cleaved and cyclized as described in procedure 1.

When Cys(Acm) was incorporated as protected building block, the cyclized side chain protected β-hairpin mimetics are dissolved in methanol (0.5 ml) to which is added dropwise a solution of iodine in methanol (1N, 1.5 equiv.) at room temperature. The reaction mixture is stirred for 4 hours at room temperature and the solvent evaporated. The crude product is subsequently deprotected and purified as described in procedure 1.

When Cys(Tr) was incorporated as protected cysteine building block, the cyclic fully protected protected β-hairpin mimetics are treated with a mixture containing trifluoro acetic acid/thioanisol/phenol/H$_2$O/ethane-dithiol/triisopropylsilane (82.5:5:5:2.5:2.5:2.5) at room temperature for 2 hours. The reduced peptide is subjected to air oxidation by stirring for 30 minutes in ammonium acetate buffer and purified as in procedure 1.

2. Synthesis of the Templates 2.1. The syntheses of (2S,4S)-4-[(allyloxy)carbonylamino]-1-[(9H-fluoren-9-yl)methoxycarbonyl]-proline (212) and (2S,4R)-4-[(allyloxy)carbonylamino]-1-[(9H-fluoren-9-yl)methoxy-carbonyl]proline (217) are shown in Schemes 42 and 43.

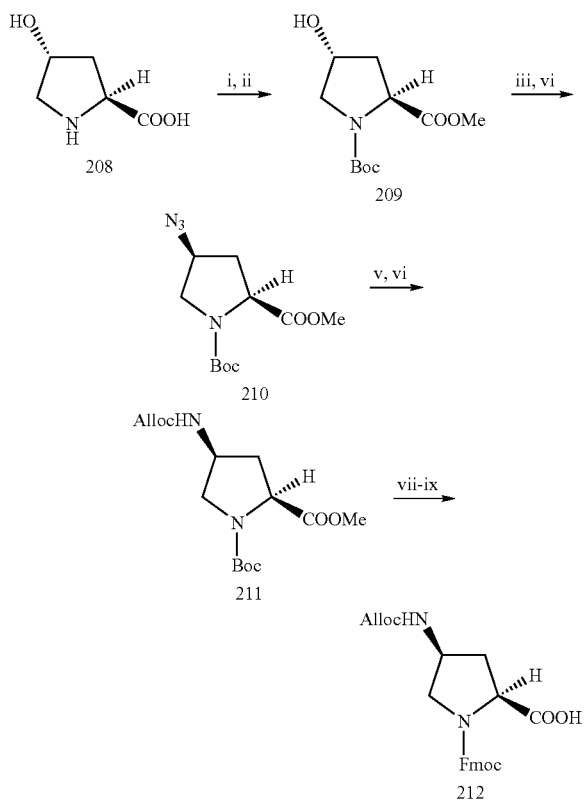

Scheme 42 i: SOCl$_2$, MeOH;
ii: Boc$_2$O, DMAP, Et$_3$N;
iii: pNO$_2$C$_6$H$_4$SO$_2$Cl, Et$_3$N;
iv: NaN$_3$, DMF;
v: SnCl$_2$, dioxane/H$_2$O;
vi: ClCOOCH$_2$CH=CH$_2$, aq. NaHCO$_3$, dioxane;
vii: LiOH, MeOH, H$_2$O;
viii: TFA, CH$_2$Cl$_2$;
ix: Fmoc-OSu, DIEA (2S,4S)-4-[(Allyloxy)carbonylamino]-1-[(9H-fluoren-9-yl)methoxycarbonyl]-proline (212)

i,ii: To a solution of (2S,4R)$_4$-hydroxyproline (30 g, 0.18 mol) in abs. methanol (300 ml) at 0° C. thionyl chloride (38 ml, 25 eq, 0.45 mol) was added dropwise. The solution was heated to reflux and stirred for 3 h under nitrogen. Then the solution was concentrated by rotary evaporation and the ester precipitated by adding diethylether. After filtration the white solid was washed with diethylether, then dried at HV: (2S, 4R)-4-hydroxyproline-methylester.hydrochloride as a white solid (29.9 g, 90%).%). TLC (CH$_2$Cl$_2$MeOH/water 70:28:2): R$_f$ 0.82. [α]$_D^{20}$=−24.5 (c=1.01, MeOH). IR (KBr): 3378s br.), 2950m, 2863w, 1745s, 1700s, 1590m, 1450s, 1415s, 1360s, 1215s, 1185s, 1080 m, 700m. $^1$H-NMR (300 MHz, MeOH-d$_4$) 4.66-4.55 (m, 2H, H—C(4), H—C(2)); 3.85 (s, 3H, H$_3$C—O); 3.45 (dd, J=12.2, 3.8, 1H, H—C(5)); 3.37-3.25 (m, 1H, H—C(5)); 2.44-2.34 (m, 1H, H—C(3)), 2.27-2.12 (m, 1H, H—C(3)). $^{13}$C-NMR (75 MHz, MeOH-d$_4$): 170.8 (s, COOMe); 70.8 (d, C(4)); 59.6 (d, C(2)); 55.2 (t, C(5)); 54.2 (q, Me); 38.7 (t, C(3)). CI-MS (NH$_3$): 146.1 ([M-Cl]$^+$).

(30 g, 0.17 mmol) of the above intermediate was dissolved in CH$_2$Cl$_2$ (300 ml), cooled to 0° C. and triethylamine (45 ml, 1.5 eq, 0.25 mol) was added dropwise. Then di-tert.-butyldicarbonate (54.0 g, 1.5 eq, 0.25 mmol) in CH$_2$Cl$_2$ (15 ml) and 4-N,N-dimethylaminopyridine (2.50 g, 0.1 eq, 17 mmol) was added and the solution stirred at room temperature overnight. Then the solution was washed with 1N aq. citric acid solution, sat. aq. NaHCO$_3$ solution, dried (Na$_2$SO$_4$), evaporated and the residue dried at high vaccum: (2S,4R)-4-Hydroxy-1-[(tert-butoxy)carbonyl]proline-methylester (209) as a white solid (39.6 g, 78%). TLC (CH$_2$Cl$_2$/MeOH 9:1): R$_f$ 0.55. [α]$_D^{24}$=−55.9 (c=0.983, CHCl$_3$). IR (KBr): 3615w, 3440w (br.), 2980m, 2950m, 2880m, 1750s, 1705s, 1680s, 1480m, 1410s, 1370s, 1340m, 1200s, 1160s, 1130m, 1090m, 1055w, 960w, 915w, 895w, 855m, 715m. $^1$H-NMR (300 MHz, CDCl$_3$): 4.47-4.37 (m, 2H, H—C(4), H—C(2)); 3.73 (s, 3H, H$_3$C—O)); 3.62 (dd, J=11.8, 4.1, 1H, H—C(S)); 3.54-3.44 (m, 1H, H—C(S)); 2.32-2.25 (m, 1H, H—C(3)); 2.10-2.03 (m, 1H, H—C(3)); 1.46+1.41 (2s, 9H, tBu). $^{13}$C-NMR (75 MHz, CDCl$_3$): 173.6 (s, COOMe); 154.3+153.9 (2s, COOtBu); 80.3 (s, C-tBu); 70.0+69.3 (2d, C(4)); 57.9+57.4 (2d, C(2)); 54.6 (t, C(5)); 51.9 (q, Me); 39.0+38.4 (2t, C(3)); 28.1+27.6 (2g, tBu). CI-MS: 246.2 ([M+H]$^+$); 190.1 ([M-tBu+H]$^+$); 146.1 ([M-BOC+H]$^+$).

iii,iv: (39 g, 0.16 mol) of 209 was dissolved in CH$_2$Cl$_2$ (300 ml) followed by addition of 4-nitrobenzenesulfonyl chloride (46 g, 1.3 eq, 0.21 mol) and Et$_3$N (33 ml, 1.5 eq, 0.24 mol) at 0° C. Then the solution was stirred overnight and brought gradually to room temperature, washed with 1N hydrochloric acid, sat. aq. NaHCO$_3$ solution and dried (Na$_2$SO$_4$). The solvents were evaporated and the crude product was purified by filtration on silica gel with (2:1) hexane/AcOEt The product was crystallized from hexane/AcOEt: (2S,4S)-4-[(p-nitrobenzyl)sulfonyloxy]-1-[(tert-butoxy)carbonyl]proline methylester as white crystals (46.4 g, 65%). TLC (hexane/AcOEt 1:1): R$_f$ 0.78. M.p.: 93-95° C. [α]$_D^{20}$=−32.3° (c=0.907, CHCl$_3$). IR (KBr): 3110w, 3071w, 2971w, 1745s, 1696s, 1609s, 1532s, 1414s, 1365s, 1348s, 1289m, 1190m, 1173m, 1122w, 1097w, 1043w, 954w, 912w, 755w, 578w. $^1$H-NMR (600 MHz, CDCl$_3$): 8.42-8.34 (m, 2H, H—C (Nos)); 8.11-8.04 (m, 2H, H—C(Nos)); 5.14 (s, 1H, H—C (4)); 4.39-4.28 (m, 1H, H—C(2)); 3.70-3.56 (m, 5H, H$_2$—C (5), H$_3$C—O); 2.58-2.38 (m, 1H, H—C(3)); 2.25-2.11 (m, 1H, H—C(3)); 1.37+1.33 (2s, 9H, tBu). $^{13}$C-NMR (150 M CDCl$_3$): 172.4+172.2 (2s, COOMe); 153.6+153.0 (2s, COOtBu); 150.8+142.0 (2s, C(Nos)); 129.0+124.6 (2d, C(Nos)); 80.4 (3, C-tBu); 80.8+79.9 (2d, C(4)); 57.1+56.9 (2d, C(2)); 52.2+51.7 (2t, C(S)); 52.3 (q, Me); 37.1+35.9 (2t, C(3)); 28.0 (q, tBu). ESI-MS (MeOH+NaI): 453.0 ([M+Na]$^+$).

(38 g, 88 mmol) of the above intermediate was dissolved in DMF (450 ml) then heated to 40° C. when sodium azide (34 g, 6 eq, 0.53 mol) was added and the solution stirred overnight. DMF was evaporated and the solid suspended in diethylether. The suspension was washed with water and dried (Na$_2$SO$_4$). The solvent was evaporated and the product dried at high vacuum: (2S,4S)-4-Azido-1-[(tert-butoxy)carbonyl] proline methylester (210) yellow oil (21.1 g, 88%). [α]$_D^{20}$=−36.9 (c=0.965, CHCl$_3$). $^1$H-NMR (600 MHz, CDCl$_3$): 4.46-4.25 (2m, 1H, H—C(2)); 4.20-4.10 (n, 1H, H—C(4)); 3.80-3.65 (m, 4H, H—C(5), H$_3$C—O); 3.53-3.41 (m, 1H, H—C (5)); 2.54-2.39 (m, 1H, H—C(3)); 2.21-2.12 (m, 1H, H—C (3)); 1.47+1.41 (2s, 9H, tBu). $^{13}$C-NMR (150 MHz, CDCl$_3$): 172.2+171.9 (2s, COOMe); 153.9+153.4 (2s, COOtBu); 80.5

(s, C-tBu); 59.2+58.2 (2d, C(4)); 57.7+57.3 (2d, C(2)); 52.4+ 52.2 (2q, Me); 51.2+50.7 (2t, C(5)); 36.0+35.0 (2t, C(3)); 28.3+28.2 (2q, tBu). EI-MS (70ev): 270.1 ([M]$^+$); 227.1 ([M—CO$_2$+H]$^+$); 169.1 ([M-BOC+H]$^+$).

v, vi: (21.1 g, 78 mmol) of the above intermediate was dissolved in a (3:1)-mixture of dioxane/water (500 ml) and SnCl$_2$ (59.2 g, 4 eq, 0.31 mol) was added at 0 and the solution stirred for 30 min. and graduallly brought to room temperature and stirred for another 5 h. After adjusting the pH to 8 with solid NaHCO$_3$, allyl chloroformate (41.5 ml, 5 eq, 0.39 mol) was added and the solution stirred at room temperature overnight. The reaction mixture was evaporated and extracted with AcOEt. The organic phase was washed with brine, dried (Na$_2$SO$_4$), the solvent evaporated and the product was dried at high vacuum: (2S,4S) [(Allyloxy)carbonylamino]-1-[(tert-butoxy)carbonyl]proline methylester (211) as a clear thick oil (22.3 g, 87%). [α]$_D^{20}$=-30.2° (c=1.25, CHCl$_3$). $^1$H-NMR (300 MHz, CDCl$_3$): 5.98-5.77 (m, 1H, H—C(β)(Alloc)); 5.32-5.12 (m, 2H, H$_2$—C(γ)(Alloc); 4.59-4.46 (m, 2H, H$_2$—C(α)(Alloc)); 4.40-4.16 (m, 2H, H—C(4), HC(2)); 3.80-3.53 (m, 4H, H—C(5), H$_3$C—O); 3.53-3.31 (m, 1H, H—C(5)); 2.54-2.17 (m, 1H, H—C(3)); 1.98-1.84 (m, 1H, H—C(3)); 1.41+1.37 (2s, 9H, tBu). ESI-MS (MeOH+ CH$_2$Cl$_2$): 351.2 ([M+Na]$^+$); 229.0 ([M-BOC+H]$^+$).

vii-ix: 22 g, 67 mmol) of 211 was dissolved in a (4:1)-mixture of methanol/water (100 ml) and LiOH (5 g, 2 eq, 134 mmol) was added at room temperature and the solution stirred for 3.5 h. The reaction mixture was evaporated and extracted with 1N hydrochloric acid (100 ml) and AcOEt. The solvent was removed and the resulting solid dissolved in 1:1 TFA/ CH$_2$Cl$_2$ (200 ml) and stirred for 2 h. The solvents were evaporated and the product dried at high vacuum: (2S,4S)-4-[(Allyloxy)carbonylamino]proline as a clear oil (21 g, 96%) $^1$H-NMR (600 MHz, MeOH-d$_4$): 5.98-5.85 (m, 1H, H—C(γ) (Alloc)); 5.30 (dd, J=17.1, 1.5 Hz, 1H, H—C(γ)(Alloc)); 5.12 (d, J=10.7 Hz, 1H, H—C(γ)(Alloc)); 4.54 (d, J=4.4 Hz, 2H, H$_2$—C(α)(Alloc)); 4.44 (t, J=8.9 Hz, 1H, H—C(2)); 4.36-4.27 (m, 1H, H—C(4)); 3.58 (dd, J=12.2, 7.3 Hz, 1H, H—C (5)); 3.34-3.32 (m, 1H, H—C(5)); 2.73 (ddd, J=13.6, 8.7, 7.2 Hz, 1H, H—C(3)); 2.23-2.15 (m, 1H, HC(3)). $^{13}$C-NMR (150 MHz, MeOH-d$_4$): 171.3 (s, COOMe); 158.3 (s, COOAllyl); 134.1 (d, C(β)(Alloc)); 118.0 (t, C(γ)(Alloc)); 66.8 (t, C(α) (Alloc)); 59.7 (d, C(2)); 51.3 (d, C(4)); 51.1 (t, C(5)); 34.9 (t, C(3)). ESI-MS (DCM+MeOH): 237.0 ([M+Na]$^+$); 215.0 ([M+H]$^+$).

(15 g, 70 mmol) of the above intermediate and 9-fluorenylmethoxycarbonylsuccinimid (28 g, 1.2 eq, 84 mmol) were dissolved in DCM (700 ml) and DIEA (48 ml, 6 eq, 0.42 mol) was added and the solution stirred overnight at room temperature. The solvent was removed and the residue dissolved in AcOEt and washed with 1N hydrochloric acid and dried (Na$_2$SO$_4$). After evaporation, the crude product was purified by filtration on silica gel with a gradient of (3:1) hexane/ AcOEt to AcOEt. The solvent was evaporated and the residue crystallized from hexane at −20° C. The product was dried at high vacuum: (2S,4)-4-[(Allyloxy)carbonylamino]-1-[(9H-fluoren-9-yl)methoxycarbonyl]-proline (212) as a white solid (23.8 mg, 78%) [α]$_D^{20}$=−27.0 (c=1.1, CHCl$_3$). IR (KBr): 3321w (br.), 3066w, 2953w, 1707s, 1530m, 1451s, 1422s, 1354m, 1250m, 1205m, 1173m, 1118m, 1033m, 977m, 936m, 759m, 739s, 621m, 597w, 571w, 545s. $^1$H-NMR (300 MHz, MeOHA-d$_4$): 7.88-7.78 (m, 2H, H—C(4')(Fmoc)); 7.71-7.61 (m, 2H, H—C(1')(Fmoc)); 7.49-7.29 (m, 4H, H—C(3')(Fmoc), H—C(2')(Fmoc)); 6.08-5.68 (m, 1H, H—C(β)(Alloc)); 5.41-5.17 (m, 2H, H$_2$C(γ)(Alloc); 4.58 (s, 2H, H$_2$—C(α)(Alloc)); 4.74-4.17 (m, 5H, H$_2$—C(10') (Fmoc), H—C(9')(Fmoc), H—C(4), H—C(2)); 3.94-3.73 (m, 1H, H—C(5)); 3.41-3.26 (m, 1H, H—C(5)); 2.74-2.54 (m, 1H, H—C(3)); 2.12-1.92 (m, 1H, H—C(3)). ESI-MS (DCM+MeOH): 459.3 ([M+Na]); 437.3 ([M+H]$^+$).

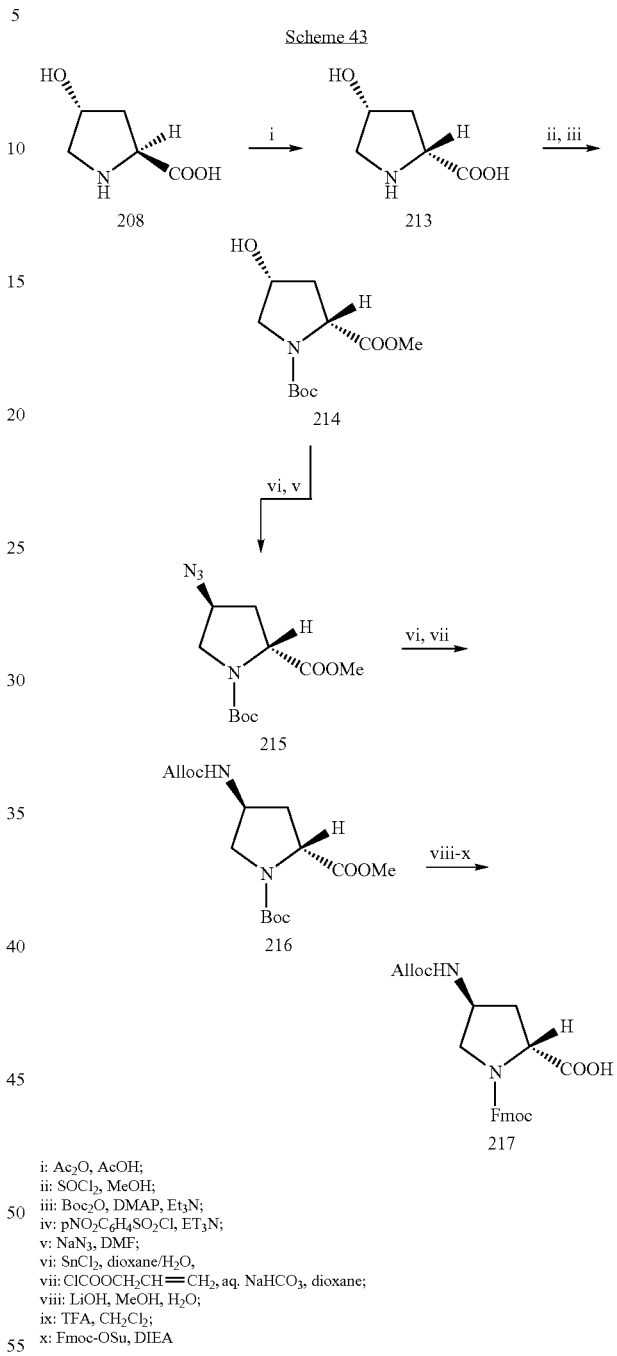

i: Ac$_2$O, AcOH;
ii: SOCl$_2$, MeOH;
iii: Boc$_2$O, DMAP, Et$_3$N;
iv: pNO$_2$C$_6$H$_4$SO$_2$Cl, ET$_3$N;
v: NaN$_3$, DMF;
vi: SnCl$_2$, dioxane/H$_2$O,
vii: ClCOOCH$_2$CH=CH$_2$, aq. NaHCO$_3$, dioxane;
viii: LiOH, MeOH, H$_2$O;
ix: TFA, CH$_2$Cl$_2$;
x: Fmoc-OSu, DIEA 2.2. (2R,4S)-4-[(Allyloxy)carbonylamino]-1-[(9H-fluoren-9-yl)methoxycarbonyl]-proline (217)

i: A solution of acetic anhydride (1.02 kg, 53eq, 10 mol) in glacial acetic acid (3 l) was heated to 50° C. and (2S,4R)-4-hydroxyproline (208) (247 g, 1.88 mol) was added in one portion.

The solution was refluxed for 5.5 h., cooled to room temperature and the solvent was removed under reduced pressure giving a thick oil. The oil was then dissolved in 2N hydrochloric acid (3.5 l) and heated to reflux for 4 h and treated with charcoal and filtered through Celite. As the solution was evaporated, white needles formed, which were filtered. The product was dried at high vacuum: (2R,4R)-4-hydroxyproline-hydrochloride (213) white cryst. needles (220.9 g, 70%). M.p.: 117° C. $[\alpha]_D^{20}$=+19.3° (c=1.04, water). IR (KBr): 3238s 3017s, 2569m, 1712s, 1584m, 1376s, 1332m, 1255s, 1204m, 1181w, 1091w, 1066w, 994w, 725m, 499s. $^1$H-NMR (600 MHz, MeOH-d$_4$): 9.64 (s, 1H, H—N); 8.89 (s, 1H, H—N); 4.55-4.53 (m, 1H, H—C(4)); 4.51 (dd, J=10.4, 3.6 Hz, 1H, H—C(2)); 3.44-3.35 (m, 2H, H$_2$—C(5)); 2.54-2.48 (m, 1H, H—C(3)); 2.40-2.34 (m, 1H, H—C(3)). $^{13}$C-NMR (150 MHz, MeOH-d$_4$): 171.9 (s, COOH); 70.3 (d, C(4)); 59.6 (d, C(2)); 55.0 (t, C(5)); 38.5 (t, C(3)). EI-MS (NH$_3$): 132.1 ([M-Cl]$^+$). The filtrate was further concentrated to give an additional 59.5 g (19%).

ii,iii: To a solution of 213 (30 g, 0.18 mol) in abs. methanol (550 ml) was added dropwise at 0° C. thionyl chloride (38 ml, 2.5 eq, 0.45 mol). The solution refluxed for 3 h under nitrogen atmosphere. The solution was evaporated and the ester hydrochloride precipitated by adding diethylether. After filtration the white solid was washed with diethylether and dried at high vacuum: (2R,4R)-4-hydroxyproline methylester-hydrochloride white solid (29 g, 89%). $[\alpha]_D^{20}$=+8.6° (c=0.873, MeOH). IR (KBr): 3388s (br.), 2980s (br.), 1730s, 1634m, 1586s, 1384s, 1248s, 1095s, 1064s, 1030m, 877m. $^1$H-NMR (300 MHz, MeOH-d$_4$): 4.59-4.44 (m, 2H, H—C(4), H—C(2)); 3.81 (s, 3H, H$_3$C—O); 3.37-3.31 (m, 2H, H$_2$—C(5)); 2.50-2.37 (m, 1H, H—C(3)), 2.37-2.27 (m, 1H, H—C(3)). $^{13}$C-NMR (75 MHz, MeOH-d$_4$): 170.9 (s, COOMe); 70.2 (d, C(4)); 59.8 (d, C(2)); 55.1 (t, C(S));)); 54.1 (q, C(Me)); 38.4 (t, C(3)). EI-MS (NH$_3$): 146.1 ([M-Cl]$^+$).

(10 g, 55 mmol) of the above intermediate was dissolved in CH$_2$Cl$_2$ (100 ml), cooled to 0° C. and triethylamine (15.2 ml, 2 eq, 0.11 mol) was added dropwise. Then di-tert.-butyldicarbonate (18.0 g, 1.5 eq, 83 mmol) in CH$_2$Cl$_2$ (10 ml) and 4-N,N-dimethylaminopyridine (0.67 g, 0.1 eq, 5 mmol) were added and the solution was stirred at RT overnight. The solution was washed with 1M aq. citric acid solution and sat. aqueous NaHCO$_3$ solution, dried (Na$_2$SO$_4$), the solvents evaporated and dried at high vaccum: (2R,4R)-4-hydroxy-1-[(tert-butoxy)-carbonyl]prolinemethylester (214) as a white solid (13 g, 97%). $[\alpha]_D^{20}$=+13.0° (c=1.06, CHCl$_3$). IR (KBr): 3466s (br.), 2985s, 2930m, 1729s, 1679s, 1424s, 1283m, 1262m, 1122s, 1089s, 969 m, 770m. $^1$H-NMR (300 MHz, CDCl$_3$): 4.43-4.26 (m, 2H, H—C(4), H—C(2)); 3.80+3.79 (2s, 3H, H$_3$C—O)); 3.76-3.47 (m, 2H, H$_2$C(5)); 2.44-2.24 (m, 1H, HC(3)); 2.16-2.03 (m, 1H, H—C(3)); 1.47+1.43 (2s, 9H, tBu). ESI-MS: 268.1 ([M+Na]$^+$).

iv,v: 214 (12.2 g, 50 mmol) was dissolved in CH$_2$Cl$_2$ (130 ml), cooled to 0° C. and 4-nitrobenzenesulfonyl chloride (14.3 g, 1.3 eq, 65 mmol) and Et$_3$N (10.3 ml, 1.5 eq, 75 mmol) were added. The reaction mixture was stirred overnight and gradually brought to room temperature. The solution was washed with 1N-hydrochloric acid and saturated aqueous NaHCO$_3$ solution, dried (Na$_2$SO$_4$), the solvents were evaporated and the crude product was purified by filtration on silica gel with (2:1)-mixture of hexane/AcOEt: 18 g (84%). The product was then recrystallized from hexane/AcOEt: (2R,4R)-4-[(p-nitrobenzyl)sulfonyloxy]-1-[(tert-butoxy)carbonyl]proline-methylester as white crystals (13.7 g, 64%). TLC (hexane/AcOEt 1:1): R$_f$ 0.76. M.p.: 113-115° C. $[\alpha]_D^{20}$=+21.6° (c=0.924, CHCl$_3$). IR (KBr): 3112s (br.), 2981s, 2955s, 2882 m, 1755s, 1683s, 1532s, 1413s, 1375s, 1348s, 1192s, 928s, 911s, 759m, 745s, 610s. $^1$H-NMR (600 MHz, CDCl$_3$): 8.45-8.35 (m, 2H, H—C(Nos)); 8.15-8.06 (m, 2H, H—C(Nos)); 5.27-5.16 (m, 1H, H—C(4)); 4.53-4.32 (m, 1H, H—C(2)); 3.75-3.60 (m, 5H, H$_2$—C(5), H$_3$C—O); 2.59-2.35 (m, 2H, H$_2$—C(3)); 1.42+1.39 (2s, 9H, tBu). $^{13}$C-NMR (150 MHz, CDCl$_3$): 171.8+171.6 (s, COOMe); 153.8+153.4 (s, COOtBu); 151.0+142.6 (s, C(Nos)); 129.2+124.7 (d, C(Nos)); 81.0 (s, C-tBu); 80.8+79.7 (d, C(4)); 57.4+57.1 (d, C(2)); 52.6+52.5+52.3+51.8 (t, C(S), q, Me); 37.2+36.3 (t, C(3)); 28.5+28.3 (q, tBu). ESI-MS (DCM+MeOH+NaI): 453.2 ([M+Na]$^+$).

(13 g, 30 mmol) of the above intermediate was dissolved in DMF (200 ml), heated to 40° C. and sodium azide (14.3 g, 6 eq, 180 mmol) was added and the reaction mixture stirred over-night. The reaction mixture was evaporated and the residue suspended in diethylether. The suspension was filtered, the filtrate washed with water and the organic phase dried (Na$_2$SO$_4$). The solvent was evaporated and the product dried at high vacuum: (2R,4S)-4-azido-1-[(tert-butoxy)carbonyl]prolinemethylester (215) as a yellow oil (8.15 g, 99%). $[\alpha]_D^{20}$=+42.8° (c=1.05, CHCl$_3$). $^1$H-NMR (300 MHz, CDCl$_3$): 4.58-40.37 (m, 1H, H—C(2)); 4.34-4.23 (m, 1H, H—C(4)); 3.92-3.51 (m, 5H, H$_2$—C(5), H$_3$C—O); 2.52-2.33 (m, 1H, H—C(3)); 2.33-2.20 (m, 1H, H—C(3)); 1.56+1.51 (2s, 9H, tBu). CI-MS (NH$_3$): 288.2 ([M+NH$_4$]$^+$); 271.1 ([M+H]$^+$).

vi,vii: 215 (8 g, 30 mmol) was dissolved in a (3:1)-mixture of dioxane/water (400 ml), cooled to 0° C. and SnCl$_2$ (22.4 g, 4 eq, 120 mmol) was added and the reaction mixture stirred for 30 min. at 0°, gradually warmed to room temperature and stirred for another 5h. After adjusting the pH of the solution to 8 with solid NaHCO$_3$, allyl chloroformate (15.7 ml, 5 eq, 150 mmol) was added. The reaction mire was stirred overnight at room temperature, evaporated and extracted with AcOEt and the organic phase washed with brine. After drying the organic phase (Na$_2$SO$_4$), the solvent was evaporated and the product dried at high vacuum: (2R,4S)-4-[(Allyloxy)carbonylamino]-1-[(tert-butoxy)carbonyl]proline-methylester as a clear thick oil (216) (8.7 g, 89%). $[\alpha]_D^{20}$=+41.9° (c=0.928, CHCl$_3$). $^1$H-NMR (300 MHz, CDCl$_3$): 5.98-5.87 (m, 1H, H—C($\beta$)(Alloc)); 5.34-5.02 (m, 2H, H$_2$—C($\alpha$)(Alloc); 4.62-4.49 (m, 21, H$_2$C($\alpha$)(Alloc)); 4.41-4.23 (m, 2H, H—C(4), H—C(2)); 3.82-3.66 (m, 41, HC(5), H$_3$C—O); 3.43-3.20 (m, 1H, H—C(5)); 2.33-2.07 (m, 2H, H$_2$—C(3)); 1.43+1.39 (2s, 9H, tBu). CI-MS (NH$_3$): 329.1 ([M+H]$^+$).

vii-x: 216 (8.4 g, 25 mmol) was dissolved in (4:1)-mixture of methanol/water (100 ml) at room temperature, LiOH (2.2 g, 2 eq, 50 mmol) added and the solution stirred overnight. Methanol was evaporated and the residue poured onto 1N hydrochloric acid (100 ml) and extracted with AcOEt. The solvent was removed and the residue dissolved in (1:1)-mixture of TFA/CH$_2$Cl$_2$ (200 ml) and stirred for 2 h. The solvents were evaporated and the product dried at high vaccum: (2R, 4R)-4-[(Allyloxy)carbonylamino]proline as a clear oil (5.2 g, 96%) $^1$H-NMR (300 MHz, MeOH-d$_4$): 6.04-5.88 (m, 1H, H$_2$—C($\beta$)(Alloc)); 5.38-5.19 (m, 2H, H$_2$—C($\gamma$)(Alloc); 4.64-4.54 (m, 3H, H$_2$—C($\alpha$)(Alloc), H—C(4)); 4.39-4.22 (m, 1H, H—C(2)); 3.71-3.60 (m, 1H, H—C(5)); 3.45-3.32 (m, 1H, H—C(5)); 2.51-2.41 (m, 2H, H$_2$C(3)). CI-MS (NH$_3$): 215.1 ([M+H]$^+$).

(200 mg, 0.86 mmol) of the above intermediate and 9-fluorenylmethoxycarbonylsuccinimide (440 mg, 1.5 eq, 1.3 mmol) were dissolved in CH$_2$Cl$_2$ (10 ml) and DIEA (466 µl, 4 eq, 3.44 mmol) was added, and the solution stirred over-night at room temperature. The solvent was removed and the residue dissolved in AcOEt, washed with 1N hydrochloric acid dried (Na$_2$SO$_4$). After evaporation, the crude product was purified by filtration over silica gel with first a gradient of (3:1) hexane/AcOEt to AcOEt. The solvent was coevaporated with CH$_2$Cl$_2$ and the product dried at high vacuum: (2R,4S)-

4-[(Allyloxy)carbonylamino]-1-[(9H-fluoren-9-yl)methoxy-cabonyl]-proline (217) white solid (90 mg, 33%) $[\alpha]_D^{20}$=+29.3 (c=1.08, CHCl$_3$). IR (KBr): 3314s (br.), 3066s (br.), 2952s (br.), 1708s (br.), 1536m, 1424s, 1353s, 1126m, 1030m, 909m, 759m, 738s, 620m. $^1$H-NMR (300 MHz, CDCl$_3$): 8.74 (s, 1H, H—N); 7.79-7.66 (m, 2H, H—C(4') (fmoc)); 7.62-7.49 (m, 2H, H—C(1')(fmoc)); 7.44-7.22 (m, 4H, H—C(3')(fmoc), H—C(2')(fmoc)); 6.03-5.74 (m, 1H, H—C(β)(Alloc)); 5.41-5.07 (m, 2H, H$_2$—C(γ)(Alloc)); 4.74-4.17 (m, 7H, H$_2$—C(10')(fmoc), H—C(9')(fmoc), H—C(4), H—C(2), H$_2$—C(α)(Alloc)); 3.91-3.76 (m, 1H, H—C(5)); 3.48-3.25 (m, 1H, H—C(5)); 2.45-2.08 (m, 2H, H$_2$—C(3)). ESI-MS (MeOH): 437.3 ([M+H]$^+$; ESI-MS (MeOH+Na): 459.1 ([M+Na]$^+$).

2.3. Starting from derivatives 210 and 215 the key precursors 219a and 221a can be prepared according to Scheme 44.

R$^{64}$: N-Hexyl (219a, 221a)

Scheme 44

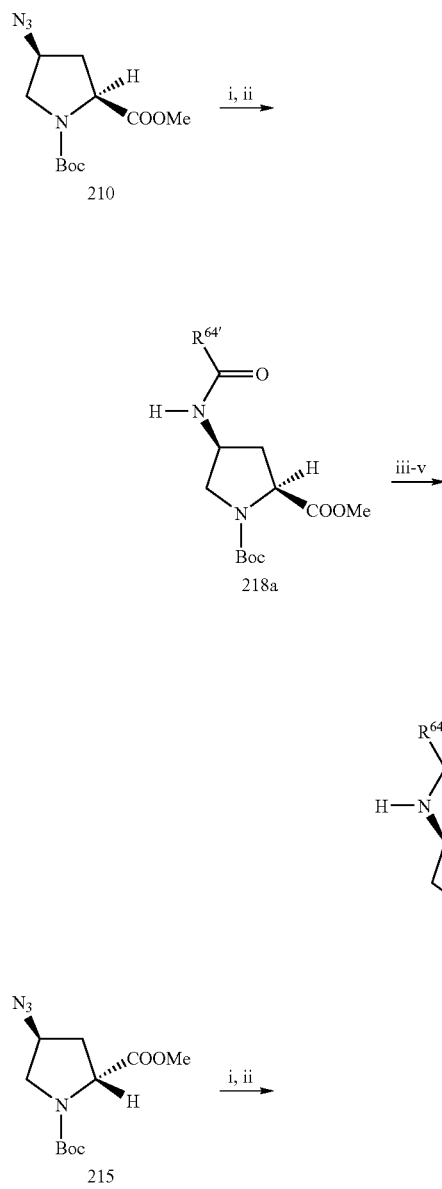

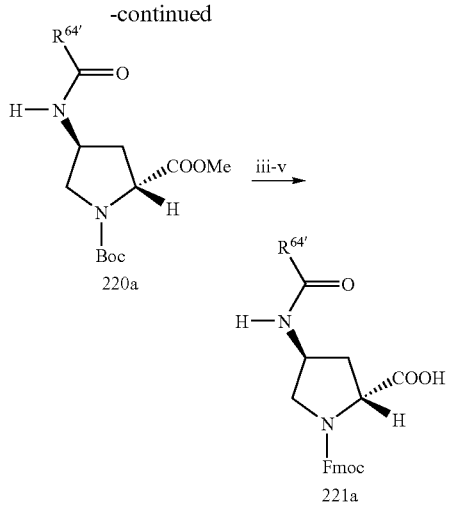

i: SnCl$_2$, dioxane/H$_2$O;
ii: R$^{64}$COCl, diisopropylethylamine, CH$_2$Cl$_2$;
iii: LiOHx1H$_2$O, MeOH, H$_2$O;
iv: TFA, CH$_2$Cl$_2$;
v: FmocOSu, Na$_2$CO$_3$ aq., dioxane i, ii: Typical Procedures To a solution of 78 mmol of azides 210 and 215 in a (3:1)-mixture of dioxane/water (500 ml) was added at 0° C. SnCl$_2$ (59.2 g, 4 eq, 0.31 mol) and the solution was stirred for 30 minutes. The reaction mixture was gradually warmed up to room temperature and stirred for another 5 hours. After adjusting the pH to 8 with solid NaHCO$_3$, the reaction mixture was extracted with CH$_2$Cl$_2$, the organic fraction dried (MgSO$_4$), evaporated and the residue dried under reduced pressure. The residue was dissolved in CH$_2$Cl$_2$ (300 ml), cooled to 4° with an ice bath, followed by addition of DIEA (20.0 ml, 117 mmol) and a solution of the appropriate acid chloride R$^{64'}$COCl (101.0 mmol) in CH$_2$Cl$_2$ (50 ml) at 4° C. The reaction mixture was stirred for 1 hour at 4° and for 18 hours at room temperature and extracted with HCl aq. (0.5N, 200 ml) and CH$_2$Cl$_2$. The organic fraction was dried (MgSO$_4$), evaporated and the residue chromatographed on SiO$_2$ with gradients of ethylacetate/hexane yielding 218a and 220a, which were converted into the final products 219a and 221a as described for the conversion of 216 into 217. The overall yields were 50-60%.

Templates (b1):

Synthesis of (2S,6S,8aR)-8a-{[(tert.-butyl)oxycarbonyl]methyl}perhydro-5,8-dioxo-{[(9H-fluoren-9-yl)methoxycarbonyl]amino}-pyrrolo[1,2-a]pyrazine-6-acetic Acid (222)

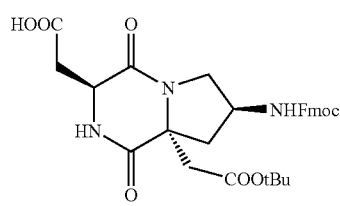

To a stirred solution of 250 mg (0.414 mmol) of allyl {(2S,6S,8aR)-8a-[(tert.-butyl)oxycarbonyl]

methyl}perhydro-5,8-dioxo-([(9H-fluoren-9-yl)methoxy-carbonyl]amino)-pyrrolo[1,2-a]pyrazin-6-acetate in a degassed mixture of dichloromethane/methanol (9:1, 3 ml) were added under argon 25 mg (0.0216 mmol) of tetrakis (triphenylphosphine)palladium, 0.05 ml of acetic acid and 0.025 ml of N-methylmorpholine. The reaction mixture was stirred for 48 hours at room temperature and poured onto water and dichloromethane. The organic phase was dried (MgSO$_4$), evaporated and the residue chromatographed on SiO$_2$ with dichloromethane/methanol (9:1) to yield 180 mg (77%) of (2S,6S,8aR)-8a-{[(tert.butyl)oxycarbonyl] methyl}perhydro-5,8-dioxo-{[(9H-fluoren-9-yl)-methoxy-carbonyl]amino}-pyrrolo[1,2-a]pyrazine-6-acetic acid (222) as a white powder.

$^1$H-NMR(300 MHz, DMSO-$_6$): 8.30 (s, 1H); 7.88 (d, J=7.2, 2H); 7.67 (d, J=7.4, 2H); 7.62 (br.s, 1H); 7.41 (t, J=7.2, 2H); 7.33 (t, J=7.4, 2H); 4.35-4.2 (m, 5H); 3.55 (br.d, J=6.3, 2H); 2.8-2.55 (m, 3H); 2.45-2.25 (m, 2H); 2.1-1.95 (m, 1H); 1.35 (s, 9H); MS(ESI): 586.1 (M+Na)$^+$, 564.1 (M+H)$^+$.

Templates (c1)

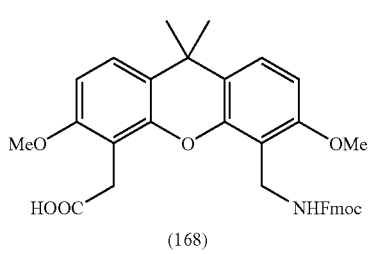

(c1-1)

(168)

Experimental procedure described in W. Bannwarth, A. Knierzinger, K. Müller, D. Obrecht, A. Trzeciak, EP 0 592 791 A2, 1993.

3. Biological Methods 3.1. Enzymatic Assays

The active enzyme concentrations were calculated using the equation described by Hendersen (P. J. F. Hendersen, Biochem. J. 1972, 127, 321-333). The inhibitor concentrations were determined by quantitative amino acid analysis. All assays were repeated in quadruplicate.

Determination of Antitrypsin Activity

As above, except the substrate was N-succinyl-L-alanyl-L-alanyl-L-prolyl-L-phenylalanin-4-nitroanilide (N-succinyl—SEQ ID NO:16—4-nitroanilide; 1.6 mM).

Apparent Ki values were calculated by fitting the initial rate data to the following equation, which assumes competitive tight-binding inhibition (J. F. Williams, J. F. Morrison, Methods Enzymol. 1979, 63, 437-467):

$$v = \frac{v_o}{2E_l}\left[E_l - I_l - K_i + \sqrt{(I_l + K_i - E_l)^2 + 4K_iI_l}\right]$$

Determination of Anti Cathepsin G Activity 10 ml of a solution of cathepsin G (0.2 U/mL, corresponding to around 2 µM, purchased from Calbiochem) were incubated for 15 minutes with increasing concentrations of inhibitor. The assays were carried out at 37° C. in a total volume of 700 µl of HEPES buffer (pH 7.5; 0.1 mol/L) containing 0.05 mol/L CaCl$_2$. Then, 70 µl of the following substrate at 20 mM in DMSO were added (—N-succinyl-L-alanyl-L-alanyl-L-prolyl-L-phenylalanin-4-nitroanilide, (N-succinyl—SEQ ID NO:16—4-nitroanilide). The release of of p-nitroanilide was monitored at 405 nm to determine the initial velocities of the reactions. Each measurement was reproduced three times (A. J. Barrett, Methods in Enzymology 1981, 80, 561-565).

3.2. Results

| Example | Ki (nM) Trypsin | Ki (nM) Chymotrypsin | Ki (nM) Cathepsin G |
|---|---|---|---|
| Ex. 1 | 100 | >10,000 | 100,000 |
| Ex. 2 | 1500 | Nd | Nd |
| Ex. 3 | >10,000 | Nd | Nd |
| Ex. 4 | 700 | Nd | Nd |
| Ex. 5 | 1900 | Nd | Nd |
| Ex. 6 | >25,000 | Nd | Nd |
| Ex. 7 | 110 | Nd | Nd |
| Ex. 8 | 710 | Nd | Nd |
| Ex. 9 | >25,000 | 4400 | Nd |
| Ex. 10 | >20,000 | 1400 | Nd |
| Ex. 11 | >20,000 | 4700 | Nd |
| Ex. 15 | 21 | 3800 | 10,000 |

Nd: not determined

What is claimed is:

1. Compounds of the general formula

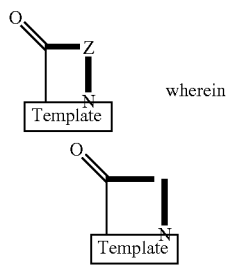

(I)

wherein is the group $^D$Pro-$^L$Pro;

Z is a chain of n α-amino acid residues, n being the integer 7 or 11, the positions of said amino acid residues in said chain being counted starting from the N-terminal amino acid; and either —n is 7; and the amino acid residues in positions 1-7 are:

—P1: Thr;
P2: Lys;
P3: Ser;
P4: Ile;
P5: Pro;
P6: Pro;
P7: Ile; or
—P1: Thr;
P2: Lys;
P3: Ala;
P4: Ile;
P5: Pro;
P6: Pro;
P7: Ile; or

—P1: Thr;
P2: Lys;
P3: Ser;
P4: Ile;
P5: Pro;
P6: Ala;
P7: Ile; or
—P1: Thr;
P2: Lys;
P3: Ser;
P4: Ile;
P5: Pro;
P6: Pro;
P7: Ala; or

—n is 11: and the amino acid residues in positions 1-11 are:

—P1: Arg;
P2: Cys;
P3: Thr;
P4: Lys;
P5: Ser;
P6: Ile;
P7: Pro;
P8: Pro;
P9: Ile;
P10: Cys;
P11: Phe;

the two Cys residues forming a disulfide bridge;
and pharmaceutically acceptable salts thereof.

2. A pharmaceutical composition comprising a compound or salt according to claim 1 and a pharmaceutically inert carrier.

3. A process for the manufacture of compounds or salts according to claim 1, which process comprises:

(a) coupling an appropriately functionalized solid support with an appropriately N-protected derivative of that amino acid which in the desired end product is in position n/2+½ or n/2–½, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating, if necessary, steps (c) and (d) until the N-terminal amino acid residue has been introduced;

(f) coupling the product thus obtained to a compound of the general formula

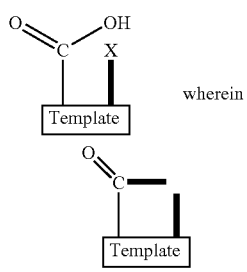

(II)

wherein is as defined above and X is an N-protecting group or, alternatively (fa) coupling the product obtained in step (d) or (e) with an appropriately N-protected derivative of $^D$Pro;

(fb) removing the N-protecting group from the product thus obtained; and (fc) coupling the product thus obtained with an appropriately N-protected derivative of $^L$Pro;

(g) removing the N-protecting group from the product obtained in step (f) or (fc);

(h) coupling the product thus obtained to an appropriately N-protected derivative of that amino acid which in the desired end-product is in position n, any functional group which may be present in said N-protected amino acid derivative being likewise appropriately protected;

(i) removing the N-protecting group from the product thus obtained;

(j) coupling the product thus obtained to an appropriately N-protected derivative of that amino acid which in the desired end-product is one position farther away from position n, any functional group which may be present in said N-protected amino acid derivative being likewise appropriately protected;

(k) removing the N-protecting group from the product thus obtained;

(l) repeating, if necessary, steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if desired, forming an interstrand linkage between sidechains of appropriate amino acid residues at opposite positions of the β-strand region;

(r) removing any protecting groups present on functional groups of any members of the chain of amino acid residues and, if desired, any protecting group(s) which may in addition be present in the molecule; and (s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

4. A method for inhibiting serine proteases which comprises administering to a patient in need of such inhibition an effective amount of a compound or salt according to claim 1.

* * * * *